US012076356B2

(12) United States Patent
Park et al.

(10) Patent No.: US 12,076,356 B2
(45) Date of Patent: Sep. 3, 2024

(54) COMPOSITION COMPRISING MOLOKHIA EXTRACT AS ACTIVE INGREDIENT FOR IMPROVING GUT MICROBIOME OR FOR ALLEVIATING, PREVENTING, OR TREATING INTESTINAL INFLAMMATION, LEAKY GUT SYNDROME, OBESITY, OR METABOLIC DISEASE

(71) Applicant: KOREA FOOD RESEARCH INSTITUTE, Jeollabuk-do (KR)

(72) Inventors: Ho-Young Park, Jeollabuk-do (KR); Yoon-sook Kim, Seoul (KR); Young-do Nam, Jeollabuk-do (KR); Moon Ho Do, Gyeonggi-do (KR); Mi-Jin Oh, Jeollabuk-do (KR); Sang-hoon Lee, Jeollabuk-do (KR); Eun Jung Lee, Seoul (KR); Hye-Bin Lee, Jeollabuk-do (KR); Hyun Jhung Jhun, Jeollabuk-do (KR)

(73) Assignee: KOREA FOOD RESEARCH INSTITUTE, Jeollabuk-do (KR)

( * ) Notice: Subject to any disclaimer, the term of this patent is extended or adjusted under 35 U.S.C. 154(b) by 748 days.

(21) Appl. No.: 17/282,820

(22) PCT Filed: Sep. 19, 2019

(86) PCT No.: PCT/KR2019/012175
§ 371 (c)(1),
(2) Date: Apr. 5, 2021

(87) PCT Pub. No.: WO2020/071667
PCT Pub. Date: Apr. 9, 2020

(65) Prior Publication Data
US 2021/0353697 A1 Nov. 18, 2021

(30) Foreign Application Priority Data

Oct. 5, 2018 (KR) .................. 10-2018-0118793
Apr. 3, 2019 (KR) .................. 10-2019-0038911
Apr. 26, 2019 (KR) .................. 10-2019-0048995

(51) Int. Cl.
*A61K 36/185* (2006.01)
*A61P 1/00* (2006.01)
*A61P 1/14* (2006.01)
*A61P 3/04* (2006.01)
*A61P 29/00* (2006.01)

(52) U.S. Cl.
CPC .............. *A61K 36/185* (2013.01); *A61P 1/00* (2018.01); *A61P 1/14* (2018.01); *A61P 3/04* (2018.01); *A61P 29/00* (2018.01)

(58) Field of Classification Search
None
See application file for complete search history.

(56) References Cited

FOREIGN PATENT DOCUMENTS

| KR | 1020080000428 | 1/2008 |
| KR | 1020090112954 | 10/2009 |
| KR | 1020180090198 | 8/2018 |
| KR | 101926263 | 12/2018 |

OTHER PUBLICATIONS

Gomaa, A.A., et al., "Amelioration of experimental metabolic syndrome induced in rats by orlistat and Corchorus olitorius leaf extract; role of adipo/cytokines," Journal of Pharmacy and Pharmacology, 71 (2019), pp. 281-291.
Li Wang et al: "Antiobesity effect of polyphenolic compounds from *Molokheiya* (L.) leaves in LDL receptor-deficient mice", European Journal of Nutrition, Steinkopff-Verlag, DA, vol. 50, No. 2. Jul. 9, 2010 (Jul. 9, 2010). pp. 127-133.
Adon Arsène M. et al: "Evaluation of the effects of *Corchorus olitorius* L. and Carapa procera in the treatment of obesity", International Journal of Research in Medical Sciences, vol. 6, No. 4, Mar. 28, 2018 (Mar. 28, 2018), pp. 1078, XP055923110, ISSN: 2320-6071.
Fazilah Nurul Farhana et al: "Influence of probiotics, prebiotics, synbiotics and bioactive phytochemicals on the formulation of functional yogurt", Journal of Functional Foods, Elsevier BV, NL, vol. 48, Jul. 20, 2018 (Jul. 20, 2018), pp. 387-399, XP085483134, ISSN: 1756-4646.
Hussein M. M.: "Utilization of some plant polysaccharides for improving yoghurt consistency | Elsevier Enhanced Reader", Dec. 27, 2011 (Dec. 27, 2011), XP055923272.
Giro Andrea: "Double Role of *Corchorus olitorius* (L.) Cultivated in Floating System:", Dec. 1, 2016 (Dec. 1, 2016), XP055923108.
Ben Yakoub Amira Racha et al: "Flavonoids, phenols, antioxidant, and antimicrobial activities in various extracts from Tossa jute leave (*Corchorus olitorus* L.)", Industrial Crops and Products, vol. 118, Aug. 1, 2018 (Aug. 1, 2018), NL, pp. 206-213, XP055923112, ISSN: 0926-6690.

(Continued)

Primary Examiner — Michael V Meller
(74) Attorney, Agent, or Firm — DUANE MORRIS LLP; Gregory M. Lefkowitz

(57) ABSTRACT

The present invention relates to a prebiotic composition, a composition for improving gut microorganisms, a composition for improving gut health or gut function, a composition for alleviating, preventing, or treating inflammatory bowel disease or leaky gut syndrome, or a composition for alleviating, preventing, or treating obesity or metabolic disease, which each comprise a molokhia extract or a molokhia polymer fraction as an active ingredient to induce the proliferation of beneficial intestinal bacteria and to improve, prevent, or treat gut heath or gut function. In addition, the composition comprising a molokhia extract or a molokhia polymer fraction as an active ingredient can alleviate, prevent, or treat bowel disease or leaky gut syndrome. Moreover, the composition of the present invention comprises a molokhia extract or a molokhia polymer fraction as an active ingredient that improves immunological activity as well as having anti-obesity activity, thereby not only treating obesity, but also alleviating, preventing, or treating obesity-induced metabolic diseases and as such, is very advantageous.

13 Claims, 18 Drawing Sheets

(56) References Cited

OTHER PUBLICATIONS

Kim, H., et al., "The Manufacturing and Biological Activity Evaluation of Wheat and Barley Mixture Bread prepared with Molokhia Powder," Korean J. Food Nutr. vol. 28. No. 4, 676~684 (2015).

Al Batran, R., et al., "Gastroprotective effects of Corchorus olitorius leaf extract against ethanol-induced gastric mucosal hemorrhagic lesions in rats," Journal of Gastroenterology and Hepatology 28 (2013) 1321-1329.

Bhawana, D., et al., "Molokhia—The Wealth for a Better Health," International Journal of Research, Feb. 2015, vol. 2, Issue 2, pp. 658-661.

Kim, M., et al., "Effects of *Corchorus olitorius* L. (Molokhia) Extracts as Functional Cosmetic Materials," Asian J Beauty Cosmetol 2017; 15(1): 23-31.

Jung, C., et al., "Effect of Molokhia (*Corchorus olitorius*) and Its Mucilage on Cholesterol Metabolism in High Cholesterol Fed Rats," Korean J. Food Sci. Technol., 2003, vol. 35, No. 33, pp. 379-385.

Lim, J.Y., "Leaky guy syndrome and semihealth," Cancerline, Oct. 11, 2016, Partial translation for relevant portion, 5th paragraph.

COMPOSITION COMPRISING MOLOKHIA EXTRACT AS ACTIVE INGREDIENT FOR IMPROVING GUT MICROBIOME OR FOR ALLEVIATING, PREVENTING, OR TREATING INTESTINAL INFLAMMATION, LEAKY GUT SYNDROME, OBESITY, OR METABOLIC DISEASE

CROSS-REFERENCE TO RELATED APPLICATIONS

This application is a § 371 national stage entry of International Application No. PCT/KR2019/012175, filed on Sep. 19, 2019, which claims priority to Korean Patent Application No. 10-2018-0118793, filed on Oct. 5, 2018, Korean Patent Application No. 10-2019-0038911, filed on Apr. 3, 2019, and Korean Patent Application No. 10-2019-0048995, filed on Apr. 26, 2019, the entire contents of which are incorporated herein by reference.

TECHNICAL FIELD

The present invention relates to a composition for improving intestinal health or intestinal function, comprising Molokhia extract as an active ingredient, a pharmaceutical composition for alleviating, preventing or treating inflammatory bowel disease, leaky gut syndrome, obesity or metabolic disease, comprising Molokhia extract as an active ingredient, and a food composition for alleviating and preventing inflammatory bowel disease, leaky gut syndrome, obesity or metabolic disease, comprising Molokhia extract as an active ingredient.

BACKGROUND ART

In addition to the basic functions of digestion, absorption, and excretion of food, the intestinal tract of the human body performs an immunological function as a defense wall in which the intestinal mucosa blocks inflow of microorganisms, their by-products, antigens, and toxins to the bloodstream of the track. In other words, the intestinal mucosa has a dual function of passing through and absorbing foreign substances simultaneously with blocking the same. Intestinal health is very important because if there is a problem with this intestinal function, not only does it cause problems in supply of nutrients to the human body, but also symptoms such as chronic constipation, diarrhea, and abdominal pain greatly interfere with daily life.

For intestinal health, an environment of an intestinal flora which is present in the intestinal track is very important. More than about 400 kinds of bacteria having a number of about 100 trillion per gram of the contents of a large intestine live in the intestine. The intestinal flora is classified into beneficial and harmful bacteria, and it is necessary to maintain the intestinal flora with many beneficial bacteria and few harmful bacteria for health. The flora may be changed according to a condition of the human body, such as a food introduced from the outside, stress, or hormone secretion. Therefore, there is a growing need for development of a method capable of promoting intestinal proliferation of the beneficial bacteria and suppressing the harmful bacteria.

Deterioration in intestinal health may lead to a variety of diseases. The cause and cure for inflammatory bowel disease, which causes chronic inflammation in the intestine, are still unknown. In general, inflammatory bowel disease refers to Crohn's disease and ulcerative colitis. Crohn's disease and ulcerative colitis may show symptoms such as diarrhea, abdominal pain, nausea, fever, loss of appetite, weight loss, and fatigue. Crohn's disease occurs mainly in the small intestine and the large intestine, but ulcerative colitis develops only in the large intestine. In addition to this, chronic Behcet's disease, which is relatively common in Korea, also belongs to ulcerative colitis.

Drugs used to treat such inflammatory bowel disease include steroidal immunosuppressants, 5-aminosalicylic acid (5-ASA) drugs (e.g., sulfasalazine) that block production of prostaglandins, mesalazine, and the like. Those drugs are limited in their use because they cause serious side effects such as abdominal fullness, headache, rash, liver disease, leukopenia, agranulocytosis, and male infertility, as well as have an insignificant therapeutic effect on inflammatory bowel disease.

Accordingly, if a therapeutic agent for inflammatory bowel disease is developed without causing the above side effects, it is expected that patients with inflammatory bowel disease may be treated more safely and effectively. However, any therapeutic agent that does not cause the side effects has not yet been developed.

Obesity can be defined as a type of disease that threatens a health due to excessive body fat accumulation. According to a report from the International Obesity Task Force (IOTF), about 1.7 billion people accounting for a quarter of the world's population need to lose weight, which has emerged as a serious social problem for both advanced and developing countries.

30~60% of the rapidly increasing lifestyle-related diseases (adult diseases) are caused by obesity. It is analyzed according to Japanese statistics that each 5 kg of excess weight causes 2 trillion yen in medical expenses. An incidence rate of overweight and obesity is one per four to five people, but it is expected to continue to increase in the future. This trend is a more serious national problem in the United States and Europe, and the incidence of childhood obesity increases rapidly due to the westernization of dietary habits in Korea. Further, the chances of eating high-fat and high-calorie meals have increased due to the rich life, so that the number of obese people is rapidly increasing because the energy consumed is significantly smaller than the energy consumed by lack of exercise. In addition, young women are striving for beauty benefits, and married women who are overweight or obese are also making great efforts to maintain the same body shape as when they were young.

Anti-obesity materials include dexflenfluramine, phenylalanine, tyrosine and methionine, orlistat as a fat binding agent (absorption inhibitor), chitosan, silbutramine as a fat burning agent, ephedrine, caffeine and fat, Garcinia cambogia fruit, L-carnitine, dietary fiber that regulates intestinal function: chacheonzapi, glucomannan, galactomannan, chromium picolinate that stabilizes a blood sugar, and the like. However, although these materials are recognized to have somewhat effectiveness, they have side effects on the heart, blood pressure, and a nervous system due to temporary weight loss, rapid weight loss and drugs.

Molokhia (scientific name: *Corchorus olitorius* L.) is a plant that grows wild in the Mediterranean coast as a green-yellow vegetable in the early 1st year of the family Phimaceae, which is native to Egypt and called as moroheiya or Jew's mallow in Japan. Fruits are opened in early April, and are harvested by cutting them about 10 cm from an end of a leaf stem that does not have flowers. Molokhia is known as a health food because it contains a good balance of calcium, dietary fiber, vitamins, and minerals. Molokhia has been loved by people as a "health" vegetable for thousands of years in Egypt to a degree that it was called king's soup or palace soup by curing a disease after the doctor fed the Molokhia soup to a sick king, and has been widely recognized and distributed as a vegetable with a variety of excellent efficacy.

Therefore, the present inventors had made careful efforts to develop prebiotics that can effectively improve total bacteria in the intestine from natural products, a composition for alleviating, preventing or treating inflammatory bowel disease or leaky gut syndrome, or a composition for alleviating, preventing or treating obesity or metabolic disease, and as a result, have completed the present invention by discovering a Molokhia extract or a Molokhia polymer fraction.

DISCLOSURE

Technical Problem

It is an object of the present invention to provide a prebiotic composition or a composition for enhancing intestinal health or intestinal function, both of which comprise a Molokhia extract as an active ingredient.

Further, it is another object of the present invention to provide a pharmaceutical composition for preventing or treating any one or more diseases selected from the group consisting of inflammatory bowel disease, leaky gut syndrome, obesity, and metabolic disease, comprising a Molokhia extract as an active ingredient.

Further, it is another object of the present invention to provide a food composition for improving or preventing any one or more diseases selected from the group consisting of inflammatory bowel disease, leaky gut syndrome, obesity and metabolic disease, comprising a Molokhia extract as an active ingredient.

Further, it is another object of the present invention to provide a novel use of a Molokhia extract for preparing a medicine for enhancing intestinal health or intestinal function by improving intestinal flora.

Further, it is another object of the present invention to provide a novel use of a Molokhia extract for preparing a medicine for treating any one or more diseases selected from the group consisting of inflammatory bowel disease, leaky gut syndrome, obesity, and metabolic disease.

Further, it is another object of the present invention to provide a method for enhancing intestinal health or intestinal function by improving intestinal flora, comprising administering an effective amount of a Molokhia extract to a patient whose growth of harmful bacteria in the intestine is relatively higher than that of beneficial bacteria in the intestine.

Furthermore, it is another object of the present invention to provide a method for treating inflammatory bowel disease or leaky gut syndrome, comprising administering an effective amount of a Molokhia extract to a patient suffering from inflammatory bowel disease or leaky gut syndrome.

Still furthermore, it is another object of the present invention to provide a method for treating obesity or metabolic disease, comprising administering an effective amount of a Molokhia extract to a patient with obesity or metabolic disease.

Technical Solution

In order to achieve the above objects, the present invention relates to a composition for enhancing intestinal health or intestinal function, comprising a Molokhia extract as an active ingredient.

Further, according to an embodiment of the present invention, the Molokhia extract may be extracted with water, an alcohol having 1 to 4 carbon atoms, or a mixed solvent thereof.

Further, according to an embodiment of the present invention, the Molokhia extract may have a prebiotic activity.

Further, according to an embodiment of the present invention, the prebiotic activity may be to promote proliferation of beneficial bacteria in the intestine.

Further, according to an embodiment of the present invention, the beneficial bacteria in the intestine may be strains of genus *Bifidobacterium*, genus *Lactobacillus*, genus *Lactococcus*, or genus *Bacteroides*.

The present invention relates to a pharmaceutical composition for preventing or treating any one or more diseases selected from the group consisting of inflammatory bowel disease, leaky gut syndrome, obesity, and metabolic disease, comprising a Molokhia extract as an active ingredient.

Further, according to an embodiment of the present invention, the Molokhia extract may be extracted with water, an alcohol having 1 to 4 carbon atoms, or a mixed solvent thereof.

Further, according to an embodiment of the present invention, the above composition may increase immune activity, suppress inflammatory response, and reduce activation of inflammatory cells.

Further, according to an embodiment of the present invention, the above composition may enhance expression of IgA and inhibit or reduce expression of IL-6 and LTB4.

Further, according to an embodiment of the present invention, the inflammatory bowel disease may be a disease selected from the group consisting of Crohn's disease, ulcerative colitis, chronic Behcet's disease, infectious enteritis, ischemic bowel disease, and radiation enteritis.

Further, according to an embodiment of the present invention, the leaky gut syndrome may be induced by a high-fat diet.

Further, according to an embodiment of the present invention, the above pharmaceutical composition may inhibit total fat cell differentiation and fat accumulation, reduce gain of body weight and body fat, lower a concentration of endotoxin, neutral fat and total cholesterol in serum, and inhibit expression of hormones related to fat differentiation in the serum.

The present invention relates to a food composition for improving or preventing any one or more diseases selected from the group consisting of inflammatory bowel disease, leaky gut syndrome, obesity, and metabolic disease, comprising a Molokhia extract as an active ingredient.

Further, according to an embodiment of the present invention, the Molokhia extract may be extracted with water, an alcohol having 1 to 4 carbon atoms, or a mixed solvent thereof.

Further, according to an embodiment of the present invention, the above food composition may increase an immune activity, suppress inflammatory response, and reduce activation of inflammatory cells.

Further, according to an embodiment of the present invention, the food composition may increase expression of IgA and inhibit or reduce expression of IL-6 and LTB4.

Further, according to an embodiment of the present invention, the inflammatory bowel disease may be a disease selected from the group consisting of Crohn's disease, ulcerative colitis, chronic Behcet's disease, infectious enteritis, ischemic bowel disease, and radiation enteritis.

Further, according to an embodiment of the present invention, the leaky gut syndrome may be induced by a high-fat diet.

Further, according to an embodiment of the present invention, the food composition may inhibit total fat cell differentiation and fat accumulation, reduce gain of body weight and body fat, lower a concentration of endotoxin, neutral fat and total cholesterol in serum, and inhibit expression of hormones related to fat differentiation in the serum.

The present invention relates to a novel use of a Molokhia extract for preparing a medicine for enhancing intestinal health or intestinal function by improving intestinal flora.

The present invention relates to a novel use of a Molokhia extract for preparing a medicine for treating any one or more diseases selected from the group consisting of inflammatory bowel disease, leaky gut syndrome, obesity, and metabolic disease.

The present invention relates to a method for enhancing intestinal health or intestinal function by improving intestinal flora, comprising administering an effective amount of a Molokhia extract to a patient whose growth of harmful bacteria in the intestine is relatively higher than that of beneficial bacteria in the intestine.

The present invention relates to a method for treating inflammatory bowel disease or leaky gut syndrome, comprising administering an effective amount of a Molokhia extract to a patient suffering from inflammatory bowel disease or leaky gut syndrome.

The present invention relates to a method for treating obesity or metabolic disease, comprising administering an effective amount of a Molokhia extract to a patient with obesity or metabolic disease.

Advantageous Effects

A prebiotic composition of the present invention for improving intestinal microflora has an effect of promoting proliferation of beneficial bacteria in the intestine, even though it does not contain dietary fiber in Molokhia. The intestinal infection caused by pathogenic bacteria can be alleviated, suppressed and prevented, and a balance of the intestinal flora can be maintained, through significant proliferation effect of the beneficial bacteria in the intestine. That is, the prebiotic composition of the present invention can be used to improve the intestinal microflora, the intestinal flora and the intestinal environment, and is not toxic so that it can be consumed in the form of a food.

Since the composition of the present invention comprises a Molokhia extract, it is possible to alleviate, prevent or treat inflammatory bowel disease by suppressing inflammation and activating immunity. In addition, the composition of the present invention has an effect of alleviating, preventing or treating leaky gut syndrome by enhancing intestinal permeability.

Since the composition of the present invention comprises a Molokhia extract, it has an effect of inhibiting total fat cell differentiation and fat accumulation, reducing gain in body weight and body fat, lowering a concentration of endotoxin, neutral fat and total cholesterol in serum, and inhibiting expression of hormones related to fat differentiation in the serum. In addition, the composition according to the present invention can be usefully used in a functional food, a drug, and the like, for alleviating, preventing and treating obesity or metabolic disease by enhancing immune activity.

DESCRIPTION OF DRAWINGS

FIG. 1A is for *Lactobacillus paracasei* ATCC 25302 (T) (*Lactobacillus paracasei* subsp. *tolerans*), FIG. 1B is for *Lactobacillus plantarum*, FIG. 1C is for *Lactococcus lactis* NCDO604(T) (*Lactococcus lactis* subsp. *lactis*), FIG. 1D is for *Bifidobacterium longum*, FIG. 1E is for *Bifidobacterium bifidum*, and FIG. 1F is for *Bifidobacterium breve*.

FIG. 2A is for *Lactobacillus paracasei* ATCC 25302(T) (*Lactobacillus paracasei* subsp. *tolerans*), FIG. 2B is for *Lactobacillus plantarum*, FIG. 2C is for *Lactococcus lactis* NCDO604(T) (*Lactococcus lactis* subsp. *lactis*), FIG. 2D is for *Bifidobacterium longum*, FIG. 2E is for *Bifidobacterium bifidum*, and FIG. 2F is for *Bifidobacterium breve*.

FIG. 4A shows an average of the beneficial bacteria activity (prebiotic activity score) in the intestine for the total bacteria of the hot water extract of Molokhia of Example 1, and FIG. 4B shows an average of the beneficial bacteria activity (prebiotic activity score) in the intestine for the total bacteria of the Molokhia polymer fraction of Example 2.

FIG. 5A shows a result of the hot water extract of Molokhia for *Bacteroides uniformis*, FIG. 5B shows a result of the Molokhia polymer fraction for *Bacteroides uniformis*, FIG. 5C shows a result of the hot water extract of Molokhia for *Bacteroides ovatus*, and FIG. 5D shows a result of the Molokhia polymer fraction for *Bacteroides ovatus*.

FIG. 6A shows a result of α-glucuronidase activity, FIG. 6B shows a result of β-glucosidase activity, and FIG. 6C shows a result of tryptophanase activity.

BEST MODE

Figure 1A:
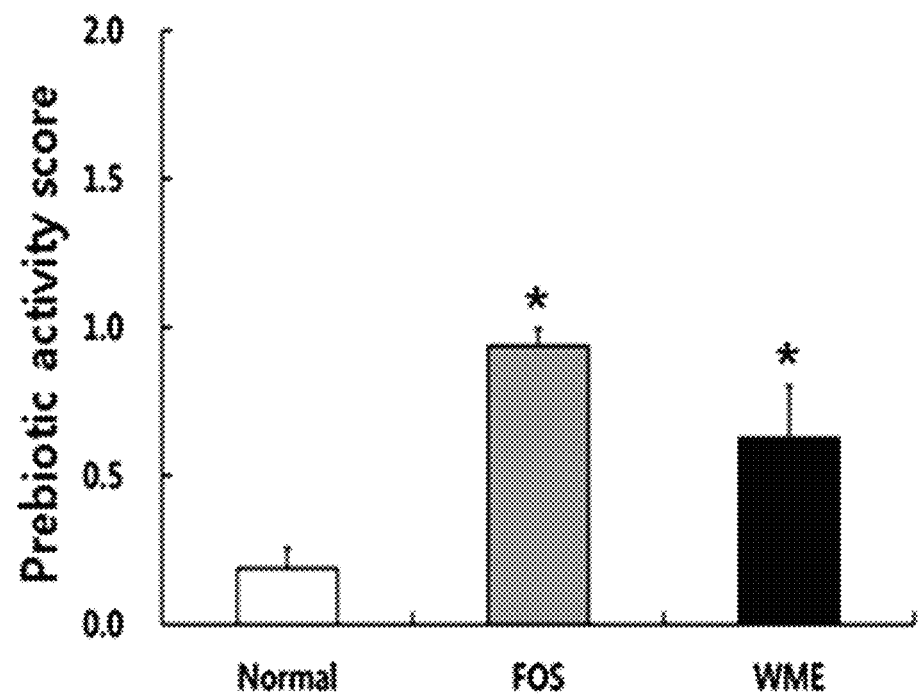
FIGS. 1A to 1F are graphs showing analyses of beneficial bacteria activity (prebiotic activity score) in the intestine when various bacteria were treated with the hot water extract of Molokhia of Example 1 and a FOS (fructo-oligosaccharide).

The present invention relates to a probiotic composition for activating a proliferation of beneficial bacteria in the intestine and a composition for enhancing intestinal health or intestinal function, both of which comprise a Molokhia extract or a Molokhia polymer fraction as an active ingredient.

Molokhia (Molokhia-*Corchorus olitorius* L.) is a green-yellow vegetable in the early 1st year of the family Phimaceae, and is rich in various nutrients so that it is called "king's vegetable". The Molokhia is recognized as an effective vegetable that has a high nutritional value and prevents adult disease in the Middle East and Africa. In Japan, Molokhia began to be cultivated in the 1980s, and in Korea, it has been cultivated on a small scale in some farms since around 1995. Molokhia is known to be rich in minerals such as dietary fiber, vitamins and calcium, as well as polyphenols, carotenoids, and the like.

In the present invention, the term 'prebiotic' is a food component that is not well digested in the body, and is a substance that induces intestinal flora in a direction beneficial to health of a host by stimulating growth or activity of limited specific symbiotic bacteria, while not being hydrolyzed or absorbed in an upper gastrointestinal tract. Specifically, it means a substance that enhances proliferation of beneficial bacteria in the intestine. More specifically, the prebiotic composition may be referred to as a composition for improving intestinal microflora or intestinal flora. It has an effect of increasing or decreasing efficacy of the probiotics, and enhancing intestinal health or intestinal function. Improvement of the intestinal microflora or the intestinal flora may refer to promoting growth of the beneficial bacteria in the intestine and inhibiting growth of harmful bacteria in the intestine, but maintaining a balance between the beneficial bacteria and the harmful bacteria in the intestine.

In the present invention, the 'extract' also includes a fraction obtained by further fractionating a crude extract. That is, the Molokhia extracts include not only those obtained by using an extraction solvent, but also those obtained by additionally applying a purification process thereto. For example, they may be purified through a variety of additional methods such as a polymer fraction obtained by passage through an ultrafiltration membrane having a certain molecular weight cut-off value, separation by various types of chromatography (separation according to size, charge, hydrophobicity or affinity), etc.

The polymer fraction may preferably be obtained by separating only a polymer material having a molecular weight of 10 kDa or more after obtaining the Molokhia extract using the extraction solvent.

Further, the 'Molokhia extract' in the present invention is obtained by extracting Molokhia leaf with water, an alcohol having 1 to 4 carbon atoms, or a mixed solvent thereof, and the extraction method does not need to be particularly limited. Preferably, the Molokhia extract may be a hot water extract of Molokhia or an ethanol aqueous solution of Molokhia, for example, an alcohol extract of Molokhia.

Further, the Molokhia extract may be obtained by processing the Molokhia extract, and then repeatedly extracting it one or more times with water, an alcohol having 1 to 4 carbon atoms or a mixed solvent thereof.

The Molokhia extract is characterized by improving proliferation of beneficial bacteria in the intestine, thereby enhancing intestinal health or intestinal function.

The Molokhia may be used as is or by cutting a Molokhia leaf into a certain size, drying the cut leaf under a shade or with a dryer, and then crushing the same. The drying period is not particularly limited as long as a moisture content in the Molokhia is less than 20%.

In the present invention, the term "as an active ingredient" or "comprising as an active ingredient" means comprising an amount of the Molokhia extract of the present invention sufficient to achieve an efficacy or activity of promoting proliferation of the beneficial bacteria in the intestine.

As used herein, the term "beneficial bacteria in the intestine" refers to beneficial bacteria existing in the intestine of a host, and strains that have beneficial activity under the intestinal environment when ingested to reach the intestine.

They mean strains that survive in the presence of gastric acid and bile to reach the small intestine, proliferate and settle in the intestine, show a useful effect in the intestine, are non-toxic, and satisfy a non-pathogenic condition. That is, they can be understood as probiotics.

It was confirmed by the present invention that a composition comprising a Molokhia extract as an active ingredient has an effect of improving intestinal flora.

The beneficial bacteria in the intestine may be strains of a genus *Bifidobacterium*, genus *Leuconostock*, genus *Pediococcus*, genus *Weissella*, genus *Streptococcus*, genus *Lactobacillus*, genus *Lactococcus*, and genus *Bacteroides*, but are not particularly limited thereto. The beneficial bacteria in the intestine may be preferably any one or more strains selected from the group consisting of *Lactobacillus paracasei* ATCC 25302(T) (*Lactobacillus paracasei* subsp. *tolerans*), *Lactobacillus plantarum*, *Lactococcus lactis* NCDO604(T) (*Lactococcus lactis* subsp. *lactis*), *Bifidobacterium longum*, *Bifidobacterium bifidum*, *Bifidobacterium breve*, *Bacteroides uniformis*, and *Bacteroides ovatus*, and may be more preferably *Lactobacillus plantarum* and/or *Bifidobacterium longum*.

*Lactobacillus* is a generic term for microorganisms that generate energy using a sugar as a nutrient source and produce a lactic acid as a final product. A reason why *Lactobacillus* is good for intestinal health is that the lactic acid produced by *Lactobacillus* creates an acidic environment that prevents harmful bacteria such as Welch bacteria from living.

If the *Lactobacillus* are active in the intestine and a lot of lactic acid is produced, the intestinal environment is acidified to suppress activities of the harmful bacteria.

Abnormality in the body occurs when certain harmful microorganisms become too influential in the body, causing the body to lose its balance. There are harmful bacteria and *Lactobacillus* in the intestine, and a ratio of *Lactobacillus* is important to keep the body healthy. It is said that if the stool of a healthy person is tested in reality, a ratio of *Lactobacillus* is high. This is called 'intestinal flora' which indicates a balance of bacteria in the intestine.

*Escherichia coli* (*E. coli*) is one of the bacteria present in the intestine of a human or an animal, especially in large intestine mainly. *Escherichia coli* does not usually show pathogenicity in the intestine, but if *Escherichia coli* enters sites other than the intestine, it causes cystitis, pyelitis, peritonitis, and sepsis.

Since *E. coli* is produced by manure discharged from humans and animals, it is used as an indicator of pathogenic bacteria in terms of environment and health.

A prebiotic composition of the present invention is the one where nutrients of beneficial bacteria in the intestine are mixed in a single formulation, and when ingested, provides an optimal environment for metabolism of the beneficial bacteria in the intestine, thereby enhancing proliferation of the beneficial bacteria in the intestine and on the contrary suppressing growth of the *E. coli* to easily exhibit a revitalizing effect.

The present invention relates to a prebiotic composition for activating proliferation of beneficial bacteria in the intestine and a composition for enhancing intestinal health or intestinal function, both of which are characterized by comprising a Molokhia polymer fraction as an active ingredient.

The prebiotic composition may refer to a composition for improving intestinal microflora or intestinal flora. The prebiotic composition has an effect of increasing or decreasing an efficacy of the probiotics, and enhancing intestinal health or intestinal function. Improvement of the intestinal microflora or the intestinal flora may refer to promoting growth of beneficial bacteria in the intestine and inhibiting growth of harmful bacteria in the intestine, but maintaining a balance between the beneficial bacteria and the harmful bacteria in the intestine.

In the present invention, the 'fraction' is obtained by further fractionating a Molokhia extract. That is, the Molokhia polymer fractions include not only those obtained by using an extraction solvent, but also those obtained by additionally applying a purification process thereto. For example, the Molokhia polymer fractions may be purified through a variety of additional methods such as a polymer fraction obtained by passage through an ultrafiltration membrane having a certain molecular weight cut-off value, separation by various types of chromatography (separation according to size, charge, hydrophobicity or affinity), etc.

The Molokhia polymer fraction is obtained by fractionating the Molokhia extract with a molecular weight of 10 kDa or more, and may contain 60 to 70% by weight of a neutral sugar and a residual amount of other polysaccharides, based on the total polymer fraction. In addition, it may further contain 1 to 10% by weight of a protein.

The neutral sugar may include rhamnose, fucose, arabinose, xylose, mannose, galactose, and glucose, but is not limited thereto.

The Molokhia polymer fraction of the present invention may be prepared by a method comprising the steps of:

(a) extracting Molokhia with water, $C_1$ to $C_4$ alcohol, or a mixed solvent thereof; and (b) recovering a polymer fraction having a molecular weight of 10 kDa or more from the extract by ultrafiltration or a gel filtration chromatography.

In the present invention, the Molokhia may be dried or undried, and be pulverized or powdered.

The Molokhia is extracted with water, an alcohol having 1 to 4 carbon atoms, or a mixed solvent thereof, and the extraction method does not need to be particularly limited.

Preferably, the Molokhia extract may be a hot water extract of Molokhia or an ethanol aqueous solution of Molokhia, for example, an alcohol extract of Molokhia.

Further, the Molokhia extract may be obtained by processing the Molokhia extract, and then repeatedly extracting it one or more times with water, an alcohol having 1 to 4 carbon atoms or a mixed solvent thereof.

After step (a), a process of heating the Molokhia extract at 90 to 110° C. for 10 to 60 minutes may be further performed. Heating increases elution of a soluble polysaccharide component, and enhances purity of the polymer fraction obtained by centrifugation by denaturing and precipitating a polymer protein contained as some impurities.

The Molokhia extract obtained through step (a) is characterized in that a ratio of the neutral sugar is remarkably high. That is, the Molokhia extract extracted according to the above step contains a large amount of a polysaccharide fraction.

Further, after step (a), a step of removing a solid from the Molokhia extract by centrifugation and filtration thereof may be further included, which may be omitted if necessary. Preferably, the above step may be carried out by centrifugation.

Next, step (b) is to recover a polymer fraction having a molecular weight of 10 kDa or more from the extract by ultrafiltration or gel filtration chromatography.

The method of recovering the fraction is not particularly limited as long as it is purified based on molecular weight, but is preferably ultrafiltration or gel filtration chromatography, more preferably gel filtration chromatography. In addition, the final polysaccharide fraction may be in the form of an extract, a concentrate, a powder, or the like.

The method of the present invention may further comprise a step of purifying polysaccharide by removing a low molecular weight substances and impurities by adding 50 to 100% of an alcohol having 1 to 4 carbon atoms to the final polymer fraction.

Specifically, according to the present invention, the Molokhia polymer fraction having a molecular weight of 10 kDa or more was obtained by treating the Molokhia extract obtained by extraction with water and an alcohol having 1 to 4 carbon atoms, with the method described above.

In the specification, the term 'fraction' includes not only a fraction obtained by treating the extraction solvent, but also a processed product of the Molokhia polymer fraction. For example, the Molokhia polymer fraction may be prepared in the form of a powder by additional processes such as distillation under reduced pressure and freeze-drying or spray-drying.

Further, the Molokhia polymer fraction of the present invention contains 60 to 70% by weight of a neutral sugar having a molecular weight of 10 kDa or more and a residual amount of other polysaccharides, and may exclude glycosides (low molecular weight substances) having a molecular weight of 10 kDa or less through a filtration process.

Figure 2A:
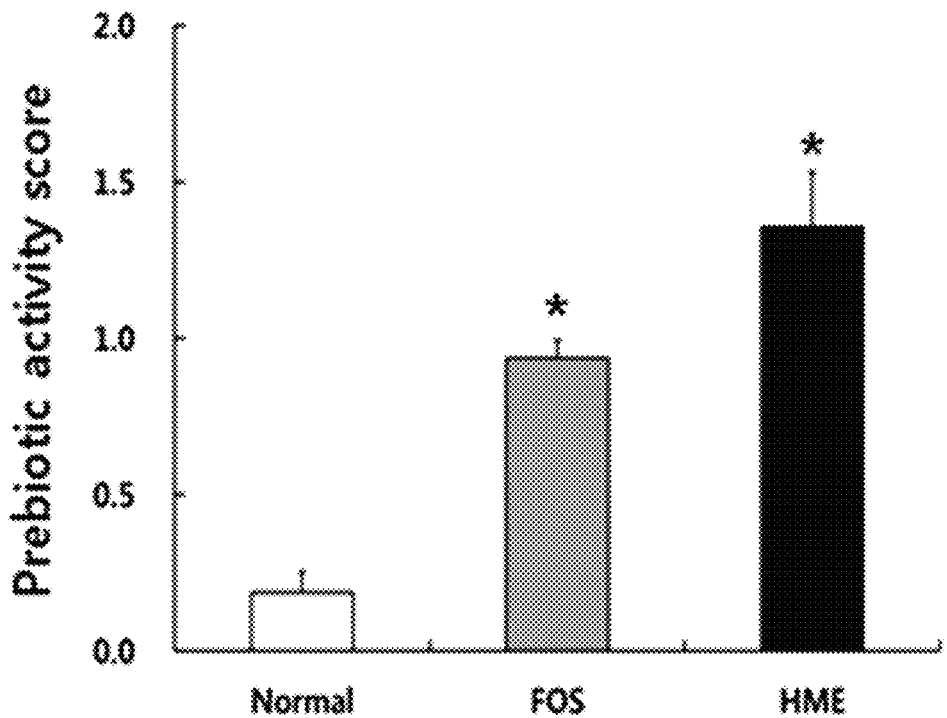
FIGS. 2A to 2C are graphs showing analyses of beneficial bacteria activity (prebiotic activity score) in the intestine when various bacteria were treated with the Molokhia polymer fraction of Example 2 and a FOS (fructo-oligosaccharide).
Figure 2B:
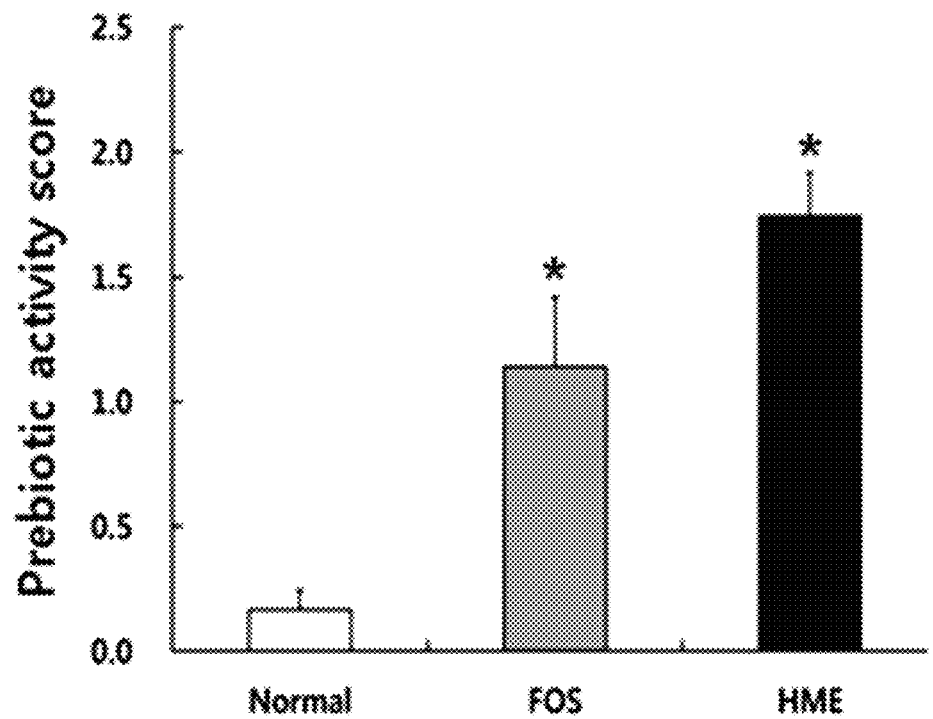
Figure 2C:
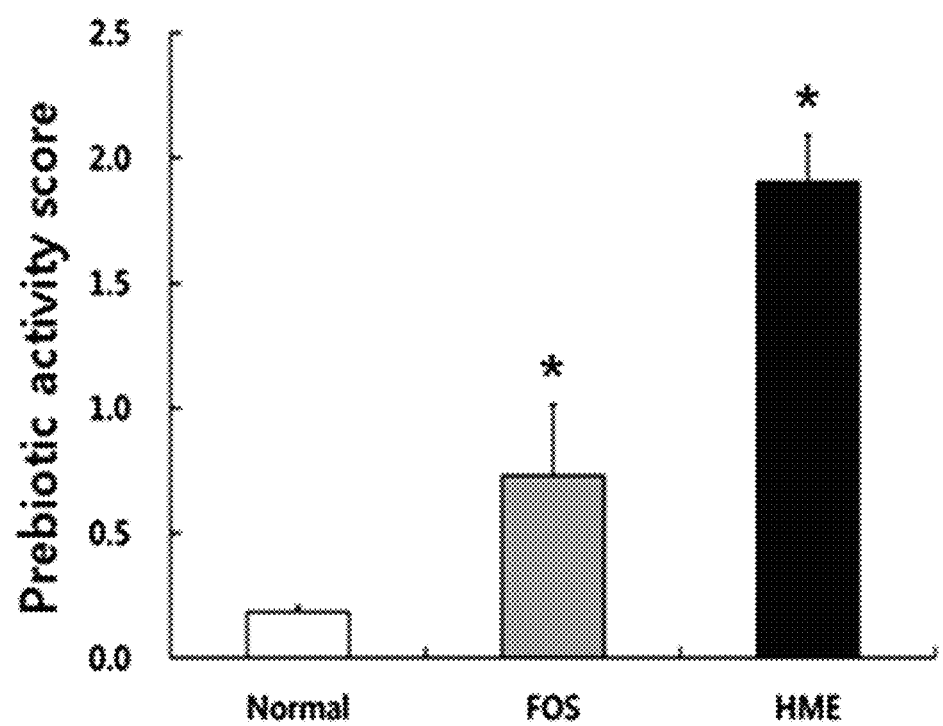

It has been known that promoting proliferation of *Lactobacillus* in the prebiotics is mainly caused by a monosaccharide. However, despite removal of the low molecular weight substances (glycosides) having a molecular weight of 10 kDa or less, the Molokhia polymer fraction of the present invention was not only confirmed to have a proliferation enhancing efficacy or activity for the majority of beneficial bacteria in the intestine, but also have a prebiotic activity score of about 0.4 to 1.6 which is higher than those of the fructo-oligosaccharide (FOS) and the hot water extract of Molokhia for *Lactococcus lactis* NCD0604(T) (*Lactococcus lactis* subsp. *lactis*), *Lactobacillus paracasei* ATCC 25302 (T) (*Lactobacillus paracasei* subsp. *tolerans*), and *Lactobacillus plantarum* (FIGS. 2A to 2C).

The Molokhia polymer fraction of the present invention broadly refers to including a Molokhia polymer fraction, a Molokhia polysaccharide fraction, and a Molokhia polymer processed product such as a Molokhia polymer powder that were formulated such that the Molokhia can be administered to an animal. Although the experiment was conducted with the Molokhia polymer fraction in the present invention, it will be expected by those skilled in the art that the desired effect can be achieved even in the same form as the Molokhia polymer processed product.

Meanwhile, the term "comprising as an active ingredient" in the specification means comprising an amount sufficient to achieve an efficacy or activity of the Molokhia polymer fraction. For example, the Molokhia polymer fraction is used at a concentration of 10 to 1500 μg/ml, preferably 100 to 1000 μg/ml. Since the Molokhia polymer fraction is a natural product and does not have a side effect on the human body even if it is administered in an excessive amount, an upper limit of the amount of the Molokhia polymer fraction contained in the composition of the present invention can be selected and carried out within an appropriate range by a person skilled in the art.

As another aspect, the present invention relates to a composition for enhancing intestinal health or intestinal function, characterized by comprising a Molokhia extract or a Molokhia polymer fraction as an active ingredient.

In the present invention, the Molokhia extract or the Molokhia polymer fraction has an effect of enhancing intestinal health or intestinal function by promoting proliferation of beneficial bacteria in the intestine.

It was confirmed by the present invention that proliferation of beneficial bacteria in the intestine was promoted, and on the contrary, the proliferation of *Escherichia coli* was inhibited, thereby enhancing intestinal health and intestinal function. The beneficial bacteria in the intestine include any one or more selected from the group consisting of *Lactobacillus paracasei* ATCC 25302(T) (*Lactobacillus paracasei* subsp. *tolerans*), *Lactobacillus plantarum*, *Lactococcus lactis* NCDO604(T) (*Lactococcus lactis* subsp. *lactis*), *Bifidobacterium longum*, *Bifidobacterium bifidum*, *Bifidobacterium breve*, *Bacteroides uniformis*, and *Bacteroides ovatus*.

In particular, in the case of using the Molokhia extract as the active ingredient, it was confirmed that it significantly proliferated *Lactobacillus plantarum* and/or *Bifidobacterium longum* than a conventional fructo-oligosaccharide. In the case of using the Molokhia polymer fractions as the active ingredient, it was confirmed that it had a remarkably higher activity of *Lactococcus lactis* NCDO604(T) (*Lactococcus lactis* subsp. *lactis*), *Lactobacillus paracasei* ATCC 25302(T) (*Lactobacillus paracasei* subsp. *tolerans*) and *Lactobacillus plantarum plantarum*) than the conventional fructo-oligosaccharide.

That is, when the Molokhia extract or the Molokhia polymer fraction of the present invention is treated together with various beneficial bacteria in the intestine known to have an effect of enhancing intestinal health or intestinal function, the proliferation of the beneficial bacteria in the intestine has been promoted to be able to use it for alleviating, inhibiting or preventing inflammatory bowel disease, leaky gut syndrome, obesity and metabolic disease.

The composition of the present invention as a pharmaceutical composition may be prepared using pharmaceutically suitable and physiologically acceptable adjuvants in addition to the Molokhia extract or the Molokhia polymer fraction as the active ingredient, and the adjuvants may include an excipient, a disintegrant, a sweetening agent, a binder, a coating agent, an expanding agent, a lubricant, a slip modifier, or a flavoring agent.

For administration, the pharmaceutical composition may be preferably formulated using one or more pharmaceutically acceptable carriers together with the above-described active ingredient.

The formulation of the pharmaceutical composition may be in the form of a granule, a powder, a tablet, a coated tablet, a capsule, a suppository, a solution, a syrup, a juice, a suspension, an emulsion, a drip agent, or an injectable solution. For example, for formulating in the form of the tablet or the capsule, the active ingredient may be combined with an oral, non-toxic pharmaceutically acceptable inert carrier such as ethanol, glycerol, water and the like. In addition, if desired or necessary, a suitable binder, lubricant, disintegrant and coloring agent may also be mixed with the pharmaceutical composition. The suitable binder includes, without limitation, starch, gelatin, natural sugar such as glucose or beta-lactose, corn syrup, natural and synthetic gums such as acacia, tragacanth or sodium oleate, sodium stearate, magnesium stearate, sodium benzoate, sodium acetate, sodium chloride, and the like. The disintegrant includes, but is not limited to, starch, methyl cellulose, agar, bentonite, xanthan gum, and the like.

The pharmaceutically acceptable carrier for the composition formulated into a liquid solution may be used in combination with saline, sterile water, Ringer's solution, buffered saline, an albumin injection solution, a dextrose solution, a maltodextrin solution, glycerol, ethanol, and one or more of those components, which are sterile and biocompatible, and may further contain other conventional additives such as an antioxidant, a buffer, and a bacteriostatic agent, if necessary. In addition, a diluent, a dispersant, a surfactant, a binder, and a lubricant may be additionally added to prepare the injectable formulation such as an aqueous solution, a suspension, an emulsion, etc., a pill, a capsule, a granule, or a tablet.

Furthermore, it can be preferably formulated according to each disease or ingredient using a method disclosed in Remington's Pharmaceutical Science, Mack Publishing Company, Easton PA, as an appropriate method in the relevant field.

The pharmaceutical composition of the present invention may be administered orally or parenterally. In the case of parenteral administration, it may be administered by intravenous injection, subcutaneous injection, intramuscular injection, intraperitoneal injection, transdermal administration, etc., but oral administration is preferred.

A suitable dosage of the pharmaceutical composition of the present invention varies depending on factors such as formulation method, a type of administration, age, weight, sex, pathological condition, diet, administration time, route of administration, an excretion rate and a response sensitivity of a patient. Usually, the skilled practitioner can readily determine and prescribe the dosage effective for the desired treatment or prophylaxis. According to a preferred embodiment of the present invention, a daily dosage of the pharmaceutical composition of the present invention is 0.001 to 10 g/kg.

The pharmaceutical composition of the present invention may be prepared in a unit dosage form by formulating the same with a pharmaceutically acceptable carrier and/or an excipient, or may be prepared by embedding into a multi-dose container. In this case, the formulation may be in the form of a solution, a suspension or emulsion in an oil or an aqueous medium, or may be in the form of an extract, a powder, a granule, a tablet or a capsule, and may additionally contain a dispersant or a stabilizer.

In another example, the Molokhia extract or the Molokhia polymer fraction as described above may be variously used as a food composition for alleviating, inhibiting or preventing inflammatory bowel disease, leaky gut syndrome, obesity and metabolic disease.

The food composition comprising the Molokhia extract or the Molokhia polymer fraction of the present invention as an active ingredient may be used in the form of various foods, such as a beverage, a gum, a tea, a vitamin complex, a powder, a granule, a tablet, a capsule, and the like.

The food composition according to the present invention may be formulated in the same manner as the pharmaceutical composition, and may be used as a functional food or added to various foods. Foods to which the composition of the present invention can be added include, for example, a beverage, an alcoholic beverage, confectionery, a diet bar, a dairy product, meat, chocolate, pizza, ramen, other noodles, gum, ice cream, a vitamin complex, a health supplement, etc.

The food composition of the present invention may include, as an active ingredient, a Molokhia extract or a Molokhia polymer fraction, as well as ingredients commonly added during food production, for example, a protein, a carbohydrate, a fat, a nutrient, a seasoning agent, and a flavoring agent. Examples of the aforementioned a carbohydrate include a monosaccharide such as glucose, fructose, and the like; a disaccharide such as maltose, sucrose, oligosaccharide, and the like; and a polysaccharide, for example, a common sugar such as dextrin and cyclodextrin, and a sugar alcohol such as xylitol, sorbitol and erythritol. The flavoring agent may include a natural flavoring agent [thaumatin, stevia extract (e.g., rebaudioside A, glycyrrhizin, etc.)], and a synthetic flavoring agent (saccharin, aspartame, etc.). For example, in case the food composition of the present invention is made into a drink and a beverage, citric acid, liquid fructose, a sugar, glucose, acetic acid, malic acid, a fruit juice, various plant extracts, and the like may be added in addition to the Molokhia extract or the Molokhia polymer fraction of the present invention.

The present invention provides a health functional food that comprises a food composition for enhancing intestinal health or intestinal function, comprising the Molokhia extract or the Molokhia polymer fraction as an active ingredient. The health functional food is a food prepared as a capsule, a powder, a suspension, etc., by adding the Molokhia extract or the Molokhia polymer fraction to a food such as a beverage, a tea, a spice, a gum, confectionery, etc., and means that the intake of such a food has a specific effect on health, which has an advantage of not having a side effect that may occur when taking a drug for a long time by using the food as a raw material, unlike a general drug. The health functional food of the present invention obtained in this way is very useful because it can be consumed on a daily basis. An amount of the Molokhia extract or the Molokhia polymer fraction added into such a health functional food cannot be uniformly regulated depending on a type of the health functional food to be targeted, but may be added within a range that does not damage an original taste of the food. The above amount is usually in the range of 0.01 to 50% by weight, preferably 0.1 to 20% by weight, based on the target food. In addition, the health functional food in the form of a pill, a granule, a tablet or a capsule may be usually added in the range of 0.1 to 100% by weight, preferably 0.5 to 80% by weight. In an embodiment, the health functional food of the present invention may be in the form of the pill, the tablet, the capsule or the beverage.

Further, the present invention provides a use of a Molokhia extract or a Molokhia polymer fraction for preparing a medicine or a food that enhances intestinal health or intestinal function. As described above, the Molokhia extract or the Molokhia polymer fraction may has a use for enhancing intestinal health or intestinal function.

Further, the present invention provides a method for improving intestinal health or intestinal function, comprising administering an effective amount of a Molokhia extract or a Molokhia polymer fraction to a mammal.

Further, the present invention provides a method for enhancing intestinal health or intestinal function by improving intestinal flora, comprising administering an effective amount of a Molokhia extract to a patient whose growth of harmful bacteria in the intestine is relatively higher than that of beneficial bacteria in the intestine.

The term "mammal" as used herein refers to a mammal subjected to treatment, observation or experiment, preferably a human.

The term "effective amount" as used herein refers to an amount of an active ingredient or a pharmaceutical composition that induces a biological or medical response to a tissue system, an animal or a human that is considered by a researcher, a veterinarian, a doctor or other clinician, and includes an amount that induces relief of relevant symptoms. The effective amount and the number of administrations for the active ingredient of the present invention may vary depending on the desired effect. Therefore, an optimal dosage to be administered can be easily determined by those skilled in the art, and be adjusted according to a variety of factors including a degree of intestinal health or intestinal function, a content of the active ingredients and other ingredients contained in the composition, a type of the formulation, and age, weight, general health condition, sex and diet of the patient, administration time, administration route and secretion rate of the composition, treatment period, and concomitant drugs. In the prevention, treatment or improvement method of the present invention, In the case of an adult, the Molokhia extract or the Molokhia polymer fraction is preferably administered at a dose of 0.001 g/kg to 10 g/kg once to several times a day.

In the treatment method of the present invention, the composition comprising the Molokhia extract or the Molokhia polymer fraction as an active ingredient may be administered in a conventional manner through an oral route, a rectal route, an intravenous route, an intraarterial route, an intraperitoneal route, an intramuscular route, an intrasternal route, a transdermal route, a topical route, an intraocular route or an intradermal route.

The present invention relates to a composition for alleviating, preventing or treating inflammatory bowel disease or leaky gut syndrome, comprising a Molokhia extract as an active ingredient.

Molokhia (Molokhia-*Corchorus olitorius* L.) is a green-yellow vegetable in the early 1st year of the family Phimaceae, and is rich in various nutrients so that it is called "king's vegetable". Molokhia is recognized as an effective vegetable that has a high nutritional value and prevents adult disease in the Middle East and Africa. In Japan, Molokhia began to be cultivated in the 1980s, and in Korea, it has been cultivated on a small scale in some farms since around 1995. Molokhia is known to be rich in minerals such as dietary fiber, vitamins and calcium, as well as polyphenols, carotenoids, and the like.

In the present invention, 'leaky gut syndrome' or 'leaky gut syndrome; LGS' refers to a phenomenon that an intestinal mucosal cell maintains a certain gap between cells, and then a polymer material can reciprocate through the gap between the cells by applying any stimulus or damage during the process of digestion and absorption to increase an intestinal mucosa permeability. 'Leaky gut syndrome' collectively means a symptom caused by a phenomenon in which a polymer material in the blood leaks into the intestinal lumen due to a failure to function in the intestine properly or the polymer material in the lumen enters the blood directly (leaky gut). The above symptom appears in various clinical conditions such as aging, allergy, multiple trauma, rheumatoid arthritis, inflammatory large bowel disease, chronic fatigue syndrome, and irritable bowel syndrome. In addition, a pathogen, an antigen, a decay substance, or the like is introduced into the intestinal mucosa due to increased permeability of the intestinal mucosa or damage to the intestinal mucosa, causing various inflammatory reactions, and an endotoxin is introduced into a bloodstream, causing bacterial translocation and intestinal endotoxemia, which results in various inflammatory and immune responses.

Such leaky gut syndrome complains of various, extensive and ambiguous symptoms without any specific symptom. Concretely, the leaky gut syndrome has a peculiarity in that it has a symptom that complain in various diseases in common.

The exact cause of leaky gut syndrome has not been found, but leaky gut syndrome may be led by the use of nonsteroidal anti-inflammatory drugs (NSAIDs) as a pain reliever for a long time, the use of an antibiotic and a steroid, In the case of receiving radiation therapy or anticancer chemotherapy as anticancer therapy, in case a change in a composition of the Normal intestinal flora occurs in an intestinal track, In the case of breeding of fungi in the intestinal track, ingestion of excessive foods, ingestion of spoiled foods or ingestion of heavy metals or toxic substances, In the case of ingestion of excessively irritating foods or hypersensitivity to certain foods, excessive drinking of alcohol, multiple trauma, exposure to acute/chronic mental stress, chronic infection of bacteria, parasites and yeast in the intestinal track, and the like.

Specifically, the composition for alleviating, preventing or treating leaky gut syndrome may also be referred to as a composition having an effect of improving, preventing, alleviating, inhibiting and treating that the permeability of the intestinal track is increased due to the above various causes. The composition has the effect of alleviating, preventing, and treating leaky gut syndrome which causes various diseases as the intestinal permeability increases so that the polymeric substance in the blood leaks into the intestinal lumen or the polymeric substance in the lumen enters the branched blood. Prevention or treatment of the leaky gut syndrome may mean suppressing a phenomenon in which a gap between the intestinal mucosal cells is loosened, thus increasing the permeability of the intestinal mucosa through which the polymer substance can reciprocate.

Inflammatory bowel disease may be a disease selected from the group consisting of Crohn's disease, ulcerative colitis, chronic Behcet's disease, infectious enteritis, ischemic bowel disease, and radiation enteritis.

According to the experimental results of the present invention, it can be seen that, when a high-fat diet is administered for a long time, an inflammatory factor such as cytokine IL-6 are increased and activation of the inflammatory cell is increased. This induces inflammation in the intestine over time and immediately causes enteritis.

In this case, it can be confirmed that, if the Molokhia extract is co-administered, the immune activity is increased, the inflammatory response is suppressed, and activation of inflammatory cells is reduced. Therefore, it can be seen that the composition comprising the Molokhia extract according to the present invention as an active ingredient has the effect of alleviating, preventing or treating inflammatory bowel disease.

The Molokhia extract is more specifically characterized by proliferating expression of IgA and inhibiting or reducing expression of IL-6 and LTB4.

In the present invention, the 'extract' includes not only a crude extract obtained by treating an extraction raw material with an extraction solvent, but also the processed product of the crude extract. For example, the Molokhia extract may be prepared in the form of a powder by an additional process such as distillation under reduced pressure and freeze-drying or spray-drying.

Further, the 'extract' in the present invention also includes a fraction obtained by further fractionating the crude extract. That is, the Molokhia extracts include not only those obtained by using the extraction solvent, but also those obtained by additionally applying a purification process thereto. For example, they may be purified through a variety of additional methods such as a polymer fraction obtained by passage through an ultrafiltration membrane having a certain molecular weight cut-off value, separation by various types of chromatography (separation according to size, charge, hydrophobicity or affinity), etc.

The polymer fraction may preferably be obtained by separating only a polymer material having a molecular weight of 10 kDa or more after obtaining the Molokhia extracts using the extraction solvent.

Further, the 'Molokhia extract' in the present invention is obtained by extracting Molokhia leaves with water, an alcohol having 1 to 4 carbon atoms, or a mixed solvent thereof, and the extraction method does not need to be particularly limited. Preferably, the Molokhia extract may be a hot water extract of Molokhia or an ethanol aqueous solution of Molokhia, for example, an alcohol extract of Molokhia. The Molokhia extract may be most preferably the hot water extract of Molokhia Further, the Molokhia extract may be the one obtained by processing the Molokhia extract, and then repeatedly extracting the same one or more times with water, an alcohol having 1 to 4 carbon atoms or a mixed solvent thereof.

The Molokhia may be used as is or by cutting a Molokhia leaf into a certain size, drying the cut leaf under a shade or with a dryer, and then crushing the same. The drying period is not particularly limited as long as a moisture content in the Molokhia is less than 20%.

In the present invention, the term "as an active ingredient" or "comprising as an active ingredient" means comprising an amount of the Molokhia extract of the present invention sufficient to alleviate, prevent or treat inflammatory bowel disease or leaky gut syndrome. Since the Molokhia extract is a natural product and does not have a side effect on the human body even if it is administered in an excessive amount, upper and lower limits of the quantity of the Molokhia extract contained in the composition of the present invention can be selected and carried out within an appropriate range by a person skilled in the art.

It was confirmed by the present invention that when a high-fat diet treated with the composition comprising the Molokhia extract as an active ingredient was administered for a long period of time, the expression of IgA was proliferated and the expression of IL-6 and LTB4 was inhibited or reduced, so that there were effects of alleviating, preventing or treating the inflammatory bowel disease, and inhibiting and reducing the intestinal permeability.

The composition of the present invention as a food composition may be used in the form of various foods comprising the Molokhia extract of the present invention as an active ingredient, for example, a beverage, a gum, a tea, a vitamin complex, a powder, a granule, a tablet, a capsule, and the like.

The food composition according to the present invention may be formulated in the same manner as a pharmaceutical composition to be described later, and may be used as a functional food or added to various foods. The foods to which the composition of the present invention can be added include, for example, a beverage, an alcoholic beverage, confectionery, a diet bar, a dairy product, meat, chocolate, pizza, ramen, other noodles, gum, ice cream, a vitamin complex, a health supplement, etc.

The food composition of the present invention may include, as an active ingredient, a Molokhia extract as well as ingredients commonly added during food production, for example, protein, carbohydrates, fat, a nutrient, a seasoning agent, and a flavoring agent. Examples of the aforementioned a carbohydrate include a monosaccharide such as glucose, fructose, and the like; a disaccharide such as maltose, sucrose, oligosaccharide, and the like; and a polysaccharide, for example, a common sugar such as dextrin and cyclodextrin, and a sugar alcohol such as xylitol, sorbitol and erythritol. The flavoring agent may include a natural flavoring agent [thaumatin, stevia extract (e.g., rebaudioside A, glycyrrhizin, etc.)], and a synthetic flavoring agent (saccharin, aspartame, etc.). For example, if the food composition of the present invention is made of a drink and a beverage, citric acid, liquid fructose, a sugar, glucose, acetic acid, malic acid, a fruit juice, various plant extracts, and the like may be added in addition to the Molokhia extract of the present invention.

The present invention provides a health functional food that comprises a food composition for alleviating, inhibiting or preventing inflammatory bowel disease or leaky gut syndrome, comprising the Molokhia extract as an active ingredient. The health functional food is a food prepared as a capsule, a powder, a suspension, etc., by adding the Molokhia extract to a food material such as a beverage, a tea, a spice, a gum, confectionery, etc., and means that the intake of such a food has a specific effect on health, which has an advantage of not having a side effect that may occur when taking a drug for a long time by using the food as a raw material, unlike a general drug. The health functional food of the present invention obtained in this way is very useful because it can be consumed on a daily basis. An amount of the Molokhia extract added to such a health functional food cannot be uniformly regulated depending on a type of the health functional food to be targeted, but may be added within the range that does not alter an original taste of the food. The above amount is usually in the range of 0.01 to 50% by weight, preferably 0.1 to 20% by weight, based on the target food. In addition, the health functional food in the form of a pill, a granule, a tablet or a capsule may be usually added in the range of 0.1 to 100% by weight, preferably 0.5 to 80% by weight. In an embodiment, the health functional food of the present invention may be in the form of the pill, the tablet, the capsule or the beverage.

In another example, the composition of the present invention may be used as a pharmaceutical composition for preventing or treating inflammatory bowel disease or leaky gut syndrome, comprising the Molokhia extract as described above as an active ingredient. In addition to the Molokhia extract as the active ingredient, it may be prepared using a pharmaceutically suitable and physiologically acceptable adjuvant, and the adjuvant may include an excipient, a disintegrant, a sweetening agent, a binder, a coating agent, an expanding agent, a lubricant, a slip modifier, or a flavoring agent.

For administration, the pharmaceutical composition may be preferably formulated using one or more pharmaceutically acceptable carriers together with the above-described active ingredient.

The formulation of the pharmaceutical composition may be in the form of a granule, a powder, a tablet, a coated tablet, a capsule, a suppository, a solution, a syrup, a juice, a suspension, an emulsion, a drip agent, or an injectable solution. For example, for formulating in the form of the tablet or the capsule, the active ingredient may be combined with an oral, non-toxic pharmaceutically acceptable inert carrier such as ethanol, glycerol, water and the like. In addition, if desired or necessary, a suitable binder, lubricant, disintegrant and coloring agent may also be mixed with the pharmaceutical composition. The suitable binder includes, without limitation, starch, gelatin, a natural sugar such as glucose or beta-lactose, corn syrup, a natural and synthetic gum such as acacia, tragacanth or sodium oleate, sodium stearate, magnesium stearate, sodium benzoate, sodium acetate, sodium chloride, and the like. The disintegrant includes, but are not limited to, starch, methyl cellulose, agar, bentonite, xanthan gum, and the like.

The pharmaceutically acceptable carrier for the composition formulated into a liquid solution may be used in combination with saline, sterile water, Ringer's solution, buffered saline, an albumin injection solution, a dextrose solution, a maltodextrin solution, glycerol, ethanol, and one or more of these components, which are sterile and biocompatible, and may further contain another conventional additive such as an antioxidant, a buffer, and a bacteriostatic agent, if necessary. In addition, a diluent, a dispersant, a surfactant, a binder, and a lubricant may be additionally added to prepare the injectable formulation such as an aqueous solution, a suspension, an emulsion, etc., a pill, a capsule, granules, or a tablet.

Furthermore, it can be preferably formulated according to each disease or ingredient using a method disclosed in Remington's Pharmaceutical Science, Mack Publishing Company, Easton PA, as an appropriate method in the relevant field.

The pharmaceutical composition of the present invention may be administered orally or parenterally. In the case of parenteral administration, it may be administered by intravenous injection, subcutaneous injection, intramuscular injection, intraperitoneal injection, transdermal administration, etc., but oral administration is preferred.

A suitable dosage of the pharmaceutical composition of the present invention varies depending on factors such as formulation method, type of administration, age, weight, sex, pathological condition, diet, administration time, route of administration, an excretion rate and response sensitivity of a patient. Usually, the skilled practitioner can readily determine and prescribe the dosage effective for the desired treatment or prophylaxis. According to a preferred embodiment of the present invention, a daily dosage of the pharmaceutical composition of the present invention is 0.001 to 10 g/kg.

The pharmaceutical composition of the present invention may be prepared in an unit dosage form by formulating the same with a pharmaceutically acceptable carrier and/or an excipient, or may be prepared by embedding in a multi-dose container. In this case, the formulation may be in the form of a solution, a suspension or an emulsion in an oil or an aqueous medium, or may be in the form of an extract, a powder, a granule, a tablet or a capsule, and may additionally contain a dispersant or a stabilizer.

Further, the present invention provides a use of a Molokhia extract for preparing a medicine that treats the inflammatory bowel disease or the leaky gut syndrome. As described above, the Molokhia extract or the Molokhia polymer fraction may has a use for alleviating, preventing or treating inflammatory bowel disease or leaky gut syndrome.

Further, the present invention provides a method for alleviating, preventing or treating inflammatory bowel disease or leaky gut syndrome, comprising administering an effective amount of a Molokhia extract to a mammal.

Further, the present invention provides a method for treating inflammatory bowel disease or leaky gut syndrome, comprising administering an effective amount of a Molokhia extract to a patient having inflammatory bowel disease or leaky gut syndrome.

The term "mammal" as used herein refers to a mammal subjected to treatment, observation or experiment, preferably a human.

The term "effective amount" as used herein refers to an amount of an active ingredient or a pharmaceutical composition that induces a biological or medical response to a tissue system, an animal or a human that is considered by a researcher, a veterinarian, a doctor or other clinician, and includes an amount that induces relief of the relevant symptom. The effective amount and the number of administrations for the active ingredient of the present invention may vary depending on the desired effect. Therefore, an optimal dosage to be administered can be easily determined by those skilled in the art, and be adjusted according to a variety of factors including a degree of symptom of the inflammatory bowel disease, a degree of intestinal permeability to the leaky gut syndrome, a content of the active ingredients and other ingredients contained in the composition, a type of the formulation, and an age, a weight, a general health condition, a sex and a diet of the patient, administration time, administration route and secretion rate of the composition, treatment period, and concomitant drugs. In the treatment or improvement method of the present invention, In the case of an adult, the Molokhia extract is preferably administered at a dose of 0.001 g/kg to 10 g/kg once to several times a day.

In the treatment method of the present invention, the composition comprising the Molokhia extract as an active ingredient may be administered in a conventional manner through an oral route, a rectal route, an intravenous route, an intraarterial route, an intraperitoneal route, an intramuscular route, an intrasternal route, a transdermal route, a topical route, an intraocular route or an intradermal route.

The present invention relates to a composition for alleviating, preventing or treating obesity or metabolic disease, comprising a Molokhia extract as an active ingredient.

Molokhia (Molokhia-*Corchorus olitorius* L.) is a green-yellow vegetable in the early 1st year of the family Phimaceae, and is rich in various nutrients so that it is called "king's vegetable". Molokhia is recognized as an effective vegetable that has a high nutritional value and prevents adult disease in the Middle East and Africa. In Japan, Molokhia began to be cultivated in the 1980s, and in Korea, it has been cultivated on a small scale in some farms since around 1995. Molokhia is known to be rich in minerals such as dietary fiber, vitamins and calcium, as well as polyphenols, carotenoids, and the like. However, a research on Molokhia leaf is currently insufficient.

In the present invention, the term 'obesity' refers to a symptom in which body fat is accumulated excessively, rather than simply gaining a lot of weight. It means that, even though the appearance looks like a Normal weight, if the percentage of the body fat is high, it can be called obesity. Normally, a method of determining the obesity is to use a body mass index (BMI). A BMI of 23 to 24.9 is judged as overweight, a BMI of 25 to 29.9 is judged as mild obesity, the BMI of 30 to 34.9 is judged as moderate obesity, and a BMI of 35 or more is judged as high obesity. Obesity is caused by a combination of multiple causes rather than a single cause, including a westernized eating habit, an incorrect eating habit, a decreased activity level, an emotional factor, and a genetic factor. The resulting obesity eventually increases a risk of developing a chronic disease such as hyperlipidemia, diabetes, and high blood pressure.

In the present invention, the term 'metabolic disease' means a condition or disease that is closely related to or is caused by obesity, and may specifically be one or more selected from the group consisting of fatty liver, type 2 diabetes, hyperlipidemia, cardiovascular disease, and arteriosclerosis.

In the present invention, fatty liver refers to a condition or disease in which fat is accumulated in an excessive amount in a liver cell due to a metabolism disorder of the fat in the liver.

In the present invention, hyperlipidemia refers to a condition or disease in which a concentration of fat components, especially cholesterol and neutral fat (triglyceride), in the blood is higher than the Normal level, and broadly includes all conditions that require lowering of the lipid concentration in the blood.

In the specification, arteriosclerosis refers to a condition or disease in which blood circulation to organs and tissues in the body decreases due to thickening of arterial walls and decreasing of elasticity, and includes "arteriosclerosis". Arteriosclerosis means a condition or disease in which blood circulation decreases due to narrowing of the lumen by depositing other substances such as fat and cholesterol on an inner wall of the artery to form plaques. Arteriosclerosis may occur in any site of the body. If it occurs in a blood vessel in the heart, coronary artery disease such as angina pectoris and myocardial infarction may be developed, and if it occurs in the brain, cerebral infarction may be developed, and if it occurs in a kidney, renal failure, and the like may be triggered.

Concretely, the composition for alleviating, preventing or treating obesity or metabolic disease may be referred to as a composition for improving, preventing, alleviating, suppressing and treating an increase in body weight or body fat due to the above various causes. More preferably, it has an effect of alleviating, preventing and treating obesity or metabolic disease triggered by a high-fat diet.

According to the experimental results of the present invention, it can be seen that, when the high-fat diet is administered for a long time, body weight and body fat are increased. This induces fat cell differentiation and fat accumulation over time, increases the body weight and a content of the body fat, and increases a concentration of endotoxins, neutral fat and total cholesterol in the serum as well as expression of hormones related to fat differentiation, thereby inducing obesity and metabolic disease.

In this case, it can be confirmed that co-administration of a Molokhia extract inhibits total fat cell differentiation and fat accumulation, reduces the increase in body weight and body fat, lowers the concentration of endotoxin, neutral fat and total cholesterol in the serum, and inhibits the expression of hormones related to fat differentiation in the serum. Therefore, it can be seen that the composition comprising the Molokhia extract according to the present invention as an active ingredient has an effect of alleviating, preventing or treating obesity or metabolic disease.

In the present invention, the 'extract' includes not only a crude extract obtained by treating an extraction raw material with an extraction solvent, but also a processed product of the crude extract. For example, the Molokhia extract may be prepared in the form of a powder by an additional process such as distillation under reduced pressure and freeze-drying or spray-drying.

Further, the 'extract' in the present invention also includes a fraction obtained by further fractionating the crude extract. That is, the Molokhia extracts include not only those obtained by using the extraction solvent, but also those obtained by additionally applying a purification process thereto. For example, they may be purified through a variety of additional methods such as a polymer fraction obtained by passage through an ultrafiltration membrane having a certain molecular weight cut-off value, separation by various types of chromatography (separation according to size, charge, hydrophobicity or affinity), etc.

The polymer fraction may preferably be obtained by separating only a polymer material having a molecular weight of 10 kDa or more after obtaining the Molokhia extracts using the extraction solvent.

Further, the 'Molokhia extract' in the present invention is obtained by extracting Molokhia leaves with water, an alcohol having 1 to 4 carbon atoms, or a mixed solvent thereof, and the extraction method does not need to be particularly limited. Preferably, the Molokhia extract may be a hot water extract of Molokhia or an ethanol aqueous solution of Molokhia, for example, an alcohol extract of Molokhia. The Molokhia extract may be most preferably the hot water extract of Molokhia Further, the Molokhia extract may be obtained by processing the Molokhia extract, and then repeatedly extracting it one or more times with water, an alcohol having 1 to 4 carbon atoms or a mixed solvent thereof.

Molokhia may be used as is or by cutting the Molokhia leaf into a certain size, drying the cut leaf under a shade or with a dryer, and then crushing the same. The drying period is not particularly limited as long as a moisture content in the Molokhia is less than 20%.

Using the Molokhia leaf is 1.5 to 2.5 times better compared to using other parts of the Molokhia in inhibiting total fat cell differentiation and fat accumulation, reducing gain of body weight and body fat, lowering a concentration of endotoxin, neutral fat and total cholesterol in the serum, and suppressing expression of hormones related to the fat differentiation in the serum, when a high-fat diet is administered for a long time. Therefore, an extract of the Molokhia leaf is significantly superior to other parts of the Molokhia in preventing, alleviating or treating obesity or metabolic disease.

In the present invention, the term "as an active ingredient" or "comprising as an active ingredient" means comprising an amount of the Molokhia extract of the present invention sufficient to alleviate, prevent or treat obesity or metabolic disease. Since the Molokhia extract is a natural product and does not have side effects on the human body even if it is administered in an excessive amount, upper and lower limits of the quantity of the Molokhia extract contained in the composition of the present invention can be selected and carried out within an appropriate range by a person skilled in the art.

The composition of the present invention may be variously used as a food composition for improving and preventing obesity or metabolic disease, comprising the Molokhia extract of the present invention as an active ingredient. The food composition comprising the Molokhia extract of the present invention as an active ingredient may be formulated in the same manner as a pharmaceutical composition to be described later, and may be used as a functional food or added to various foods. Foods to which the composition of the present invention can be added include, for example, a beverage, an alcoholic beverage, confectionery, a diet bar, a dairy product, meat, chocolate, pizza, ramen, other noodles, gum, ice cream, a vitamin complex, a health supplement, etc.

The food composition of the present invention may include, as an active ingredient, a Molokhia extract as well as ingredients commonly added during food production, for example, protein, carbohydrates, fat, a nutrient, a seasoning agent, and a flavoring agent. Examples of the aforementioned a carbohydrate include a monosaccharide such as glucose, fructose, and the like; a disaccharide such as maltose, sucrose, oligosaccharide, and the like; and a polysaccharide, for example, a common sugar such as dextrin and cyclodextrin, and a sugar alcohol such as xylitol, sorbitol and erythritol. The flavoring agent may include a natural flavoring agent [thaumatin, stevia extract (e.g., rebaudioside A, glycyrrhizin, etc.)], and a synthetic flavoring agent (saccharin, aspartame, etc.). For example, if the food composition of the present invention is made of a drink and a beverage, citric acid, liquid fructose, a sugar, glucose, acetic acid, malic acid, a fruit juice, various plant extracts, and the like may be added in addition to the Molokhia extract of the present invention.

The present invention provides a health functional food that comprises a food composition for alleviating, inhibiting or preventing obesity and metabolic disease, comprising the Molokhia extract as an active ingredient. The health functional food is a food prepared as a capsule, a powder, a suspension, etc., by adding the Molokhia extract to a food material such as a beverage, a tea, a spice, a gum, confectionery, etc., and means that the intake of such a food has a specific effect on health, which has an advantage of not having a side effect that may occur when taking a drug for a long time by using the food as a raw material, unlike a general drug. The health functional food of the present invention obtained in this way is very useful because it can be consumed on a daily basis. An amount of the Molokhia extract added to such a health functional food cannot be uniformly regulated depending on a type of the health functional food to be targeted, but may be added within the range that does not alter an original taste of the food. The above amount is usually in the range of 0.01 to 50% by weight, preferably 0.1 to 20% by weight, based on the target food. In addition, the health functional food in the form of a pill, a granule, a tablet or a capsule may be usually added in the range of 0.1 to 100% by weight, preferably 0.5 to 80% by weight. In an embodiment, the health functional food of the present invention may be in the form of the pill, the tablet, the capsule or the beverage.

In another example, as described above, the composition of the present invention may be used as a pharmaceutical composition for preventing or treating obesity or metabolic disease, comprising the Molokhia extract as an active ingredient. The pharmaceutical composition may be prepared using pharmaceutically suitable and physiologically acceptable adjuvants in addition to the Molokhia extract as the active ingredient, and the adjuvants may include an excipient, a disintegrant, a sweetening agent, a binder, a coating agent, an expanding agent, a lubricant, a slip modifier, or a flavoring agent.

For administration, the pharmaceutical composition may be preferably formulated using one or more pharmaceutically acceptable carriers together with the above-described active ingredient.

The formulation of the pharmaceutical composition may be in the form of a granule, a powder, a tablet, a coated tablet, a capsule, a suppository, a solution, a syrup, a juice, a suspension, an emulsion, a drip agent, or an injectable solution. For example, for formulating in the form of the tablet or the capsule, the active ingredient may be combined with an oral, non-toxic, pharmaceutically acceptable inert carrier such as ethanol, glycerol, water and the like. In addition, if desired or necessary, a suitable binder, lubricant, disintegrant and coloring agent may also be mixed with the pharmaceutical composition. The suitable binder includes, without limitation, starch, gelatin, a natural sugar such as glucose or beta-lactose, corn syrup, a natural and synthetic gum such as acacia, tragacanth or sodium oleate, sodium stearate, magnesium stearate, sodium benzoate, sodium acetate, sodium chloride, and the like. The disintegrant includes, but is not limited to, starch, methyl cellulose, agar, bentonite, xanthan gum, and the like.

The pharmaceutically acceptable carrier for the composition formulated into a liquid solution may be used in combination with saline, sterile water, Ringer's solution, buffered saline, an albumin injection solution, a dextrose solution, a maltodextrin solution, glycerol, ethanol, and one or more of these components, which are sterile and biocompatible, and may further contain another conventional additive such as an antioxidant, a buffer, and a bacteriostatic agent, if necessary. In addition, a diluent, a dispersant, a surfactant, a binder, and a lubricant may be additionally added to prepare the injectable formulation such as an aqueous solution, a suspension, an emulsion, etc., a pill, a capsule, granules, or a tablet.

Furthermore, it can be preferably formulated according to each disease or ingredient using a method disclosed in Remington's Pharmaceutical Science, Mack Publishing Company, Easton PA, as an appropriate method in the relevant field.

The pharmaceutical composition of the present invention may be administered orally or parenterally. In the case of parenteral administration, it may be administered by intravenous injection, subcutaneous injection, intramuscular injection, intraperitoneal injection, transdermal administration, etc., but the oral administration is preferred.

A suitable dosage of the pharmaceutical composition of the present invention varies depending on factors such as formulation method, type of administration, age, weight, sex, pathological condition, diet, administration time, route of administration, excretion rate and response sensitivity of a patient. Usually, the skilled practitioner can readily determine and prescribe the dosage effective for the desired treatment or prophylaxis. According to a preferred embodiment of the present invention, a daily dosage of the pharmaceutical composition of the present invention is 0.001 to 10 g/kg.

The pharmaceutical composition of the present invention may be prepared in a unit dosage form by formulating the same with a pharmaceutically acceptable carrier and/or an excipient, or may be prepared by embedding into a multi-dose container. In this case, the formulation may be in the form of a solution, a suspension or emulsion in an oil or an aqueous medium, or may be in the form of an extract, a powder, a granule, a tablet or a capsule, and may additionally contain a dispersant or a stabilizer.

Further, the present invention provides a novel use of a Molokhia extract for preparing a medicine for treating obesity or metabolic disease.

Further, the present invention provides a method for alleviating, preventing or treating obesity or metabolic disease, comprising administering an effective amount of the Molokhia extract to a mammal. In addition, the present invention provides a method for treating obesity or metabolic disease, comprising administering an effective amount of the Molokhia extract to a patient suffering from obesity or metabolic disease.

The term "mammal" as used herein refers to a mammal subjected to treatment, observation or experiment, preferably a human.

The term "effective amount" as used herein refers to an amount of an active ingredient or a pharmaceutical composition that induces a biological or medical response to a tissue system, an animal or a human that is considered by a researcher, a veterinarian, a doctor or other clinician, and includes an amount that induces relief of the relevant symptom. The effective amount and the number of administrations for the active ingredient of the present invention may vary depending on the desired effect. Therefore, an optimal dosage to be administered can be easily determined by those skilled in the art, and be adjusted according to a variety of factors including body weight, body fat, neutral fat and cholesterol or obesity level in the serum, contents of an active ingredient and other ingredients contained in the composition, a type of the formulation, and an age, a weight, a general health condition, a sex and a diet of a patient, administration time, a route of administration, secretion rate of the composition, treatment period, and concomitant drugs. In the prevention, treatment or improvement method of the present invention, In the case of an adult, the Molokhia extract is preferably administered at a dose of 0.001 g/kg to 10 g/kg, more preferably 0.1 g/kg to 10 g/kg, once to several times a day.

In the treatment method of the present invention, the composition comprising the Molokhia extract as an active ingredient may be administered in a conventional manner through an oral route, a rectal route, an intravenous route, an intraarterial route, an intraperitoneal route, an intramuscular route, an intrasternal route, a transdermal route, a topical route, an intraocular route or an intradermal route. The composition may be preferably administered in the oral route or the intraperitoneal route.

MODE FOR INVENTION

Hereinafter, preferred Examples are described to aid in understanding of the present invention, but the following Examples are only illustrative of the present invention. It is obvious to those skilled in the art that various changes and modifications can be carried out within the scope of the present invention and the technical idea. Further, it also is natural that such changes and modifications fall within the appended claims.

Example 1. Hot Water Extract of Molokhia

Domestic Molokhia leaf grown in Hongcheon, Gangwon-do was purchased and used. The Molokhia leaf was dried in a drying oven at 50° C. and then pulverized to a size of 1.0 mm or less with a grinder to prepare a powder of the Molokhia leaf.

Distilled water corresponding to 20 times a volume of 5 g of the Molokhia leaf powder was added, followed by reflux extraction at 80° C. for 3 hours to obtain a hot water extract. After filtering the hot water extract, it was concentrated under reduced pressure using a vacuum rotary evaporator, and freeze-dried for 72 hours. The hot water extract of Molokhia obtained by the above method was named WME (Water-soluble molokhia extract) or WEML (Water-soluble extract from molokhia leaves).

Example 2. Molokhia Polymer Fraction

Domestic Molokhia leaf grown in Hongcheon, Gangwon-do was purchased and used. The Molokhia leaf was dried in a drying oven at 50° C. and then pulverized to a size of 1.0 mm or less with a grinder to prepare a powder of the Molokhia leaf.

Distilled water corresponding to 20 times a volume of 100 g of the Molokhia leaf powder was added, followed by reflux extraction at a temperature of 80° C. for 3 hours to obtain a hot water extract. After filtering the hot water extract, it was concentrated under reduced pressure to be 1/10 of the extract using a vacuum rotary evaporator, and 80% ethanol (alcohol) of 4 times the volume (v/v) of the concentrated hot water extract was added and precipitated by centrifugation (6000 rpm, 635×g, 30 minutes) for 24 hours to obtain a precipitate. A small amount of distilled water was added to redissolve the precipitate, followed by performing dialysis with a dialysis membrane (MW cut off 12,000, Sigma-Aldrich Co., St. Louis, MO, USA) for 2 to 3 days to remove a low molecular weight material from the precipitate, and freeze-drying for 72 hours to obtain a Molokhia polymer fraction. The Molokhia polymer fraction obtained by the above method was named HME (High-molecular fraction of molokhia extract) or HFML (High-molecular fraction of molokhia leaves).

Comparative Example 1. Mixed Extract of Molokhia

A mixed extract of Molokhia was prepared in the same manner as in Example 1, except that a mixed powder of Molokhia leaf and stem (1:1 weight ratio) was used instead of the powder of Molokhia leaf.

Comparative Example 2. Extract of Molokhia Stem

A extract of Molokhia stem was prepared in the same manner as in Example 1, except that a powder of Molokhia stem was used instead of the powder of Molokhia leaf.

Comparative Example 3. Garcinia Cambogia Extract

A Garcinia cambogia extract from Unicon Natural Products PVT, India was purchased and used. In this case, the Garcinia cambogia extract contained HCA of 600 mg/g or more.

EXPERIMENTAL EXAMPLE

Experimental Example 1. Analysis of a Compositive Sugar for the Hot Water Extract of Example 1 and the Polymer Fraction of Example 2

A compositive sugar was hydrolyzed by partially modifying a method of Albersheim et al. to derivatize each compositive sugar with alditol acetate and aldonolactone, and then analyzed using a GC (Gas Chromatography ACME-6100, Young-Lin Co. Ltd., Anyang, Korea). The samples of Example 1 and Example 2 were hydrolyzed by reacting them in 2 M TFA (trifluoroacetic acid) at 121° C. for 1.5 hours, and then dissolved in 1 ml of 1 M $NH_4OH$ (ammonia solution) and reduced in 10 mg of $NaBH_4$ for 4 hours. An appropriate amount of acetic acid was added to remove residual $NaBH_4$, followed by repeatedly drying with methanol to remove excess acetic acid, which was converted into alditol corresponding to each compositive sugar.

To determine a composition of a neutral sugar, 1 ml of acetic anhydride was added to each alditol and reacted at 121° C. for 30 min to convert the same to alditol acetate, which was then separated and extracted with a solvent system of chloroform/$H_2O$ 2-phases. The extract was dried, and then dissolved in a small amount of acetone for use as a sample for GC analysis.

A quantity of protein was measured according to the Bradford method, and BSA (Bovine Serum Albumin, Sigma Aldrich) was used as a standard and diluted at a constant multiple with 1 mg/ml as the highest concentration. After adding 20 μl of each standard and sample to 980 μl of a Bradford reagent, an absorbance was measured at 595 nm using a microplate reader. The quantity of protein was converted into an amount for the BSA.

A total sugar was measured according to a phenol-sulfuric acid method. After adding an equal amount of 5% phenol solution to 0.5 mL of the sample solution and stirring, 2.5 mL of concentrated sulfuric acid (98%, v/v) was added and reacted at a room temperature for 20 minutes to measure an absorbance at 470 nm using a microplate reader. A quantity of the total sugar was converted into an amount for a glucose standard (Sigma Aldrich) by preparing a calibration curve with the glucose standard.

As a result, physicochemical characteristics analyzing main ingredients and contents of the hot water extract and the alcohol extract from the Molokhia leaf are shown in Table 1 below.

TABLE 1

| Classification | Example 1(WME) | Example 2(HME) |
|---|---|---|
| Extraction yield (%) | 49.35 | 1.89 |
| Chemical composition (%) | | |
| Neutral sugar | 39.43 ± 0.50 | 61.40 ± 4.61 |
| Protein | 0.55 ± 0.35 | 1.47 ± 0.22 |
| Total dietary fiber (wt. %) | 0.1 | 0.05 |
| Inert dietary fiber (wt. %) | 0.01 | — |

The content ratios (%) of the chemical composition represents ratios in a dry sample.

As shown in Table 1, it was confirmed that the hot water extract of Molokhia prepared from Example 1 had a high yield of 49.35%, a protein content of 0.55% by weight, and a neutral sugar content of 39.43% by weight. On the other hand, it was confirmed that the Molokhia polymer fraction prepared from Example 2 had a low yield of 1.89% and a neutral sugar content of 61.40% by weight. In conclusion, it was analyzed that most of the Molokhia polymer fraction (HME) of Example 2 was occupied by a sugar.

In the case of dietary fiber of Molokhia, which is widely known to have an effect of enhancing intestinal health or intestinal function, it was confirmed that it was hardly observed in the hot water extract of Molokhia of Example 1 and the Molokhia polymer fraction of Example 2.

Experimental Example 2. Analysis of Proliferation Activity of Beneficial Bacteria in the Intestine for the Hot Water Extract of Example 1 and the Polymer Fraction of Example 2

Isolation and Identification of Strains for Measuring Activity of Beneficial Bacteria in the Intestine In order to analyze a prebiotic activity score of the hot water extract of Molokhia of Example 1 and the Molokhia polymer fraction of Example 2, strains known as beneficial bacteria in the intestine were selected and secured. The strains were isolated from fermented human intestines and traditional foods (soybean paste, kimchi, etc.) or sold and used at the Biological Resource Center.

Lactobacillus paracasei ATCC 25302(T) (Lactobacillus paracasei subsp. tolerans), Lactobacillus plantarum, Lactococcus lactis NCDO604(T) (Lactococcus lactis subsp. lactis), Bifidobacterium long gum, Bifidobacterium bifidum, Bifidobacterium breve, Bacteroides uniformis, Bacteroides ovatus, and Escherichia coli were secured.

The Lactobacillus and Lactococcus strains were cultured using a MRS medium, the Bifidobacterium strains were cultured using a BL medium, and the Bacteroides strains were cultured using a BHI medium. The cultivation was performed by standing the strains in a pH of 6.5±0.2 at a temperature of 37° C. for 48 hours, and the oxygen demand was anaerobic. The strains were preserved through a freeze-drying or a cell suspension freezing.

Isolation and Identification of Strains for Measuring an Activity of E. coli

In order to analyze a prebiotic activity score of the hot water extract of Molokhia of Example 1 and the Molokhia polymer fraction of Example 2, E. coli was sold and used at the Biological Resource Center.

Strain Cultivation for Measuring Activity of Beneficial Bacteria and E. coli in Intestine For cultivation of the isolated and identified strains, Lactobacilli MRS agar and Lactobacilli MRS broth were used as a lactic acid bacteria, and BL agar and BL broth were used as Bifidobacterium strains. BHI agar and BHI broth were used as Bacteroides strains, and tryptic soy agar and tryptic soy broth were used as E. coli. The medium was purchased from Difco.

Colonies of the strains were plated on agar medium corresponding to each strain, firstly cultured at 37° C. for 24 hours, and then inoculated into 10 ml of a liquid medium, followed by being secondly cultured at 37° C. for 24 hours. When an absorbance at 600 nm reached 2.0, 1% (v/v) was inoculated into this culture medium. In this cultivation, M9 minimal medium (MB cell) was used, wherein the M9 medium was prepared by adding 2 g/L of glucose, 0.015 g/L of $CaCl_2$), and 0.5 g/L of $MgSO_4$.

Experimental Example 2-1. Analysis of Activity (Prebiotic Activity Score) of Beneficial Bacteria in the Intestine for a Hot Water Extract of Molokhia The obtained strains were added 1% (v/v) to M9 medium containing glucose of 10 mg/ml, respectively, to prepare a control group.

Further, the obtained strains were added 1% (v/v) to M9 medium containing fructo-oligosaccharides (FOS) of 10 mg/ml, respectively, and *Bacteroides* strains were added 1% (v/v) to M9 medium containing 10 mg/ml of inulin to prepare a positive control group. The obtained strains were added 1% (v/v) to M9 medium containing a hot water extract of 10 mg/ml of Molokhia, respectively, to prepare an experimental group.

Each group was measured for an absorbance at 600 nm using a microplate reader immediately after inoculation (0 hourss) of the strains and 24 hours after the inoculation, and these values were substituted into Equation 1 below to determine activity values (prebiotic activity score) of the beneficial bacteria in the intestine.

$$\text{Prebiotic activity score} = \left[ \frac{\text{probiotic log O.D. on the probiotic at 24 h} - \text{probiotic log O.D. on the probiotic at 0 h}}{\text{probiotic log O.D. on glucose at 24 h} - \text{probiotic log O.D. on glucose at 0 h}} \right] - \left[ \frac{\text{enterie log O.D. on the probiotic at 24 h} - \text{enterie log O.D. on the probiotic at 0 h}}{\text{enterie log O.D. on glucose at 24 h} - \text{enterie log O.D. on glucose at 0 h}} \right] \quad [\text{Equation 1}]$$

In the above equation,

The "probiotic log OD on the prebiotic at 24 h" is an absorbance measured at 600 nm using a microplate reader 24 hours after inoculation of *Lactobacillus, Bifidobacterium* and *Bacteroides* strains in the positive control group or the experimental group.

The "probiotic log O.D. on the prebiotic at 0 h" is an absorbance measured at 600 nm using a microplate reader 24 hours after inoculation of *Lactobacillus, Bifidobacterium* and *Bacteroides* strains in the positive control group or the experimental group.

The "probiotic log O.D. on glucose at 24 h" is an absorbance measured at 600 nm using a microplate reader 24 hours after inoculation of *Lactobacillus, Bifidobacterium*, and *Bacteroides* strains in a glucose control group.

The "probiotic log O.D. on glucose at 0 h" is an absorbance measured at 600 nm using a microplate reader 0 hours after inoculation of *Lactobacillus, Bifidobacterium*, and *Bacteroides* strains in the glucose control group.

The "enteric log O.D. on the prebiotic at 24 h" is an absorbance measured at 600 nm using a microplate reader 24 hours after inoculation of *E. coli* in the positive control group or the experimental group.

The "enteric log O.D. on the prebiotic at 0 h" is an absorbance measured at 600 nm after inoculating *E. coli* in the positive control group or the experimental group, using a microplate reader.

The "enteric log O.D. on glucose at 24 h" is an absorbance measured at 600 nm using a microplate reader 24 hours after inoculation of *E. coli* in the glucose control group.

The "enteric log O.D. on glucose at 0 h" is an absorbance measured at 600 nm after inoculating *E. coli* in the glucose control group, using a microplate reader.

Figure 1B:
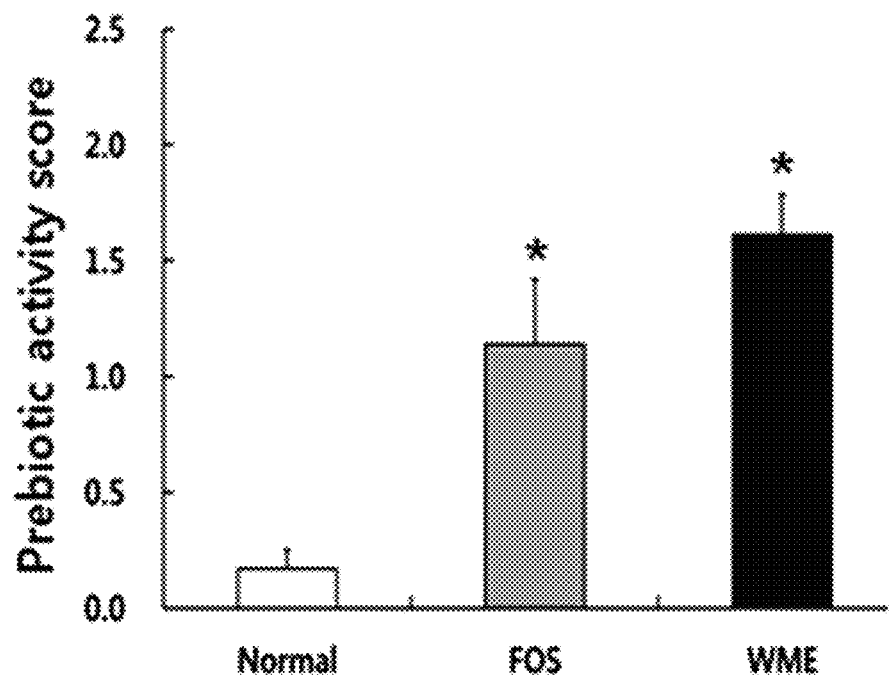
Figure 1C:
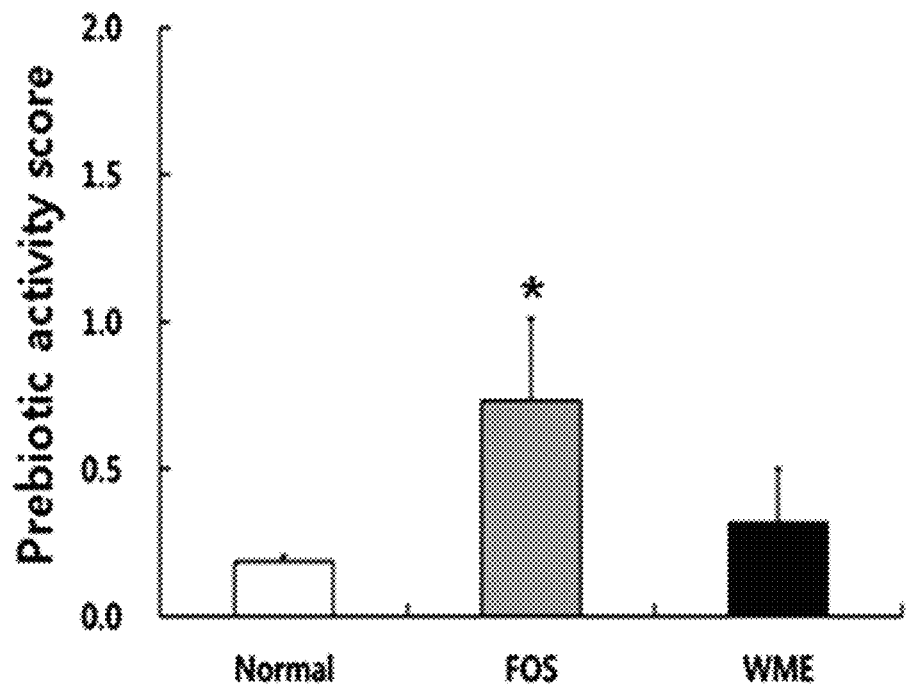
Figure 1D:
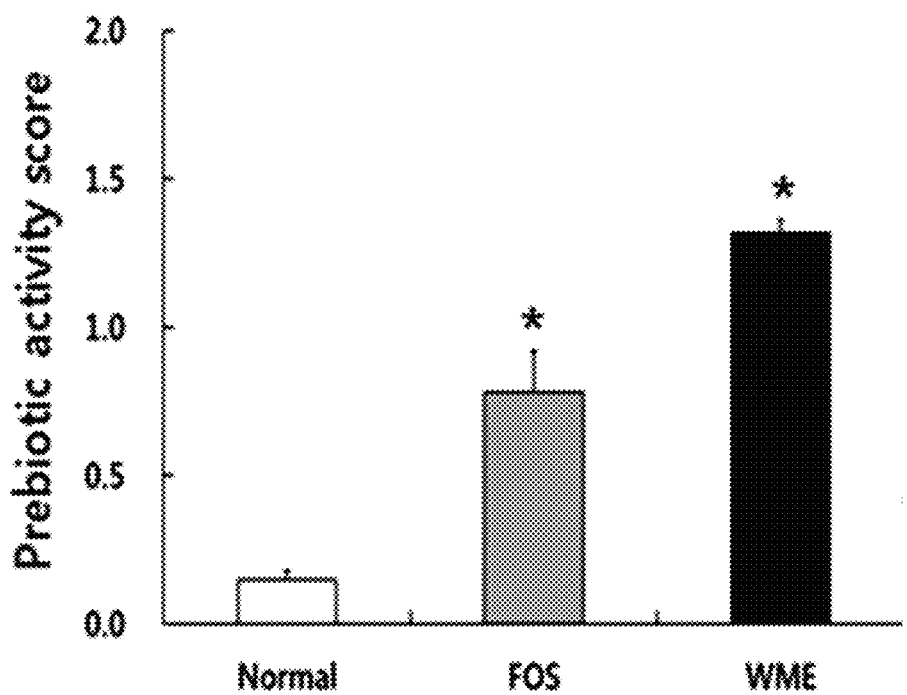
Figure 1E:
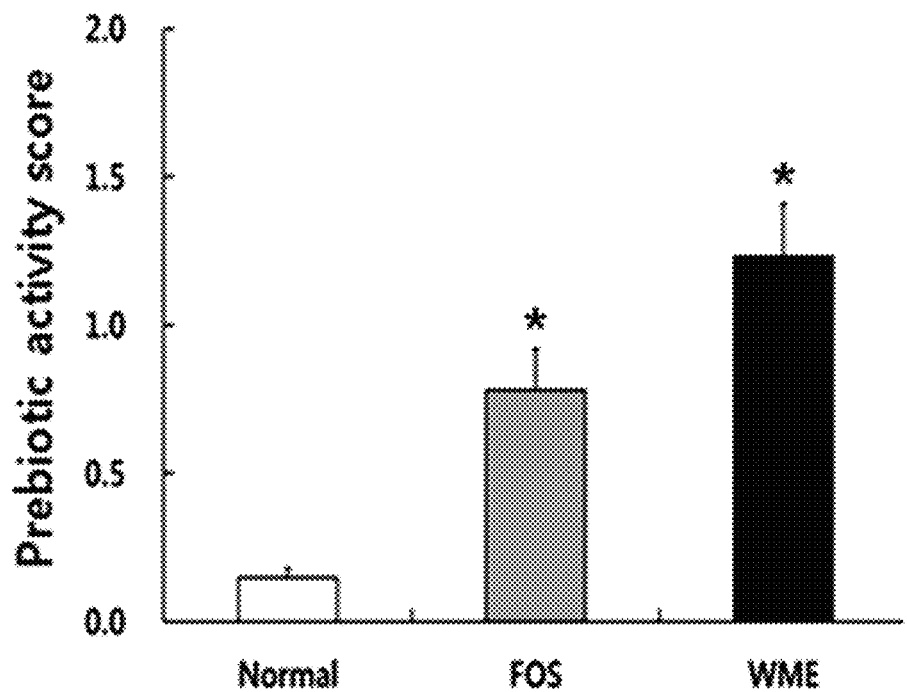
Figure 1F:
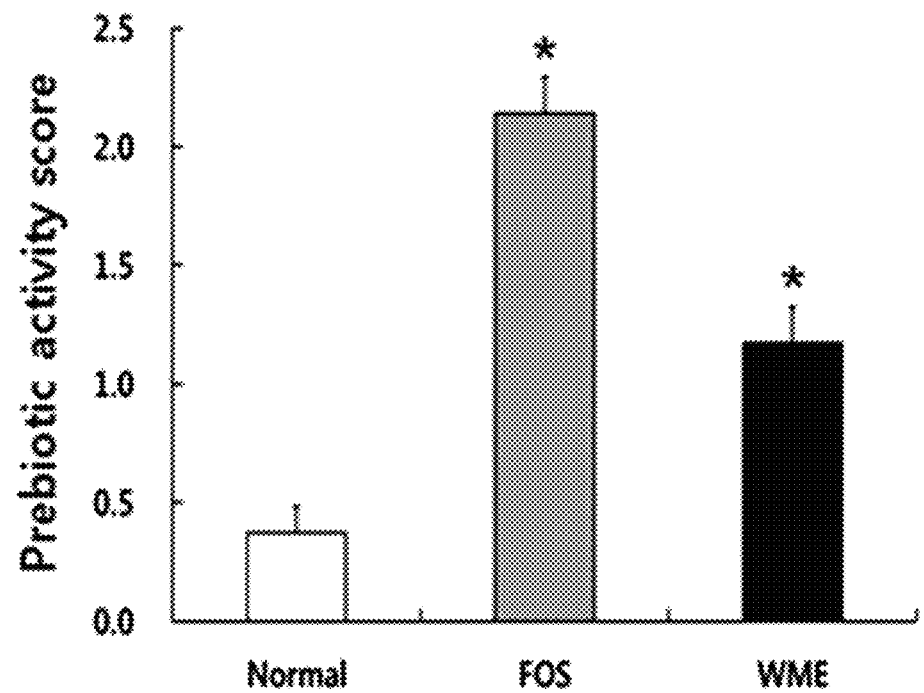

FIGS. 1A to 1F are graphs showing analyses of beneficial bacteria activity (prebiotic activity score) in the intestine when various bacteria were treated with the hot water extract of Molokhia of Example 1 and FOS (fructo-oligosaccharide). FIG. 1A is for *Lactobacillus paracasei* ATCC 25302 (T) (*Lactobacillus paracasei* subsp. *tolerans*), FIG. 1B is for *Lactobacillus plantarum*, FIG. 1C is for *Lactococcus lactis* NCDO604(T) (*Lactococcus lactis* subsp. *lactis*), FIG. 1D is for *Bifidobacterium longum*, FIG. 1E is for *Bifidobacterium bifidum*, and FIG. 1F is for *Bifidobacterium breve*.

Figure 3A:
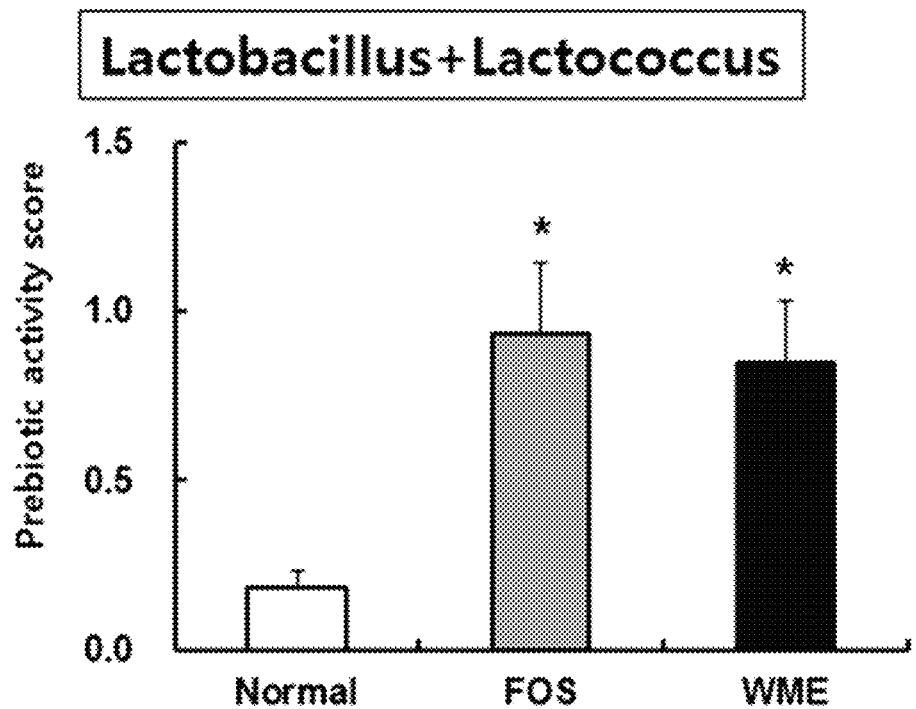
FIG. 3A is a graph showing analysis of an activity (prebiotic activity score) for *Lactobacillus* and *Lactococcus* among beneficial bacteria in the intestine when total bacteria were treated with the hot water extract of Molokhia of Example 1 and a FOS (fructo-oligosaccharide)
Figure 4A:
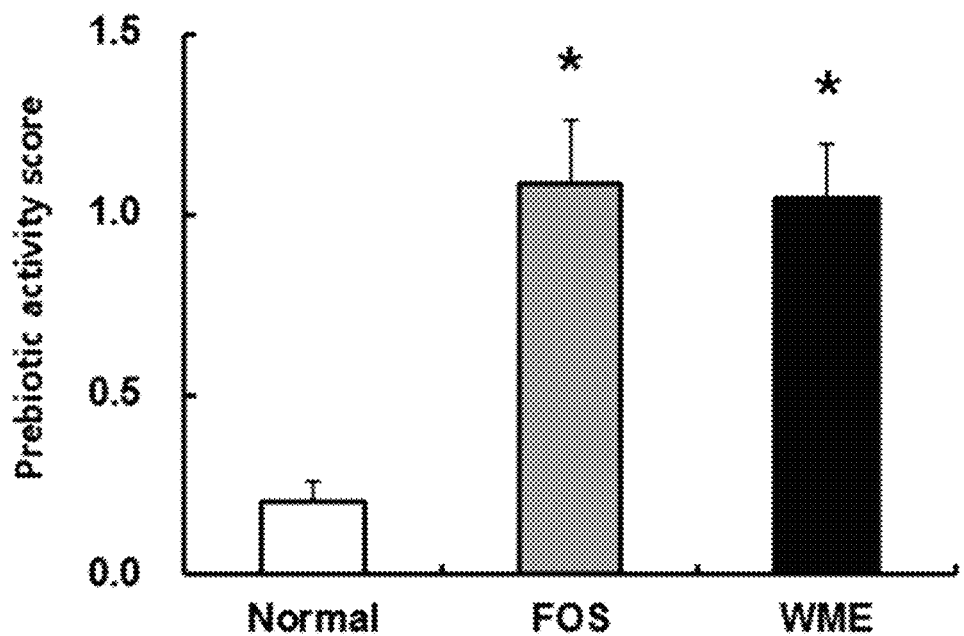
FIG. 4A is a graphs showing analysis of beneficial bacteria activity (prebiotic activity score) in the intestine when total bacteria were treated with the hot water extract of Molokhia of Example 1 and a FOS (fructo-oligosaccharide)

FIG. 3A shows an average of the activity (prebiotic activity score) for *Lactobacillus* and *Lactococcus* among beneficial bacteria in the intestine for the total strains of a hot water extract, and FIG. 4A shows an average of the activity (prebiotic activity score) of beneficial bacteria in the intestine for the total strains of the hot water extract of Molokhia of Example 1.

Figure 5A:
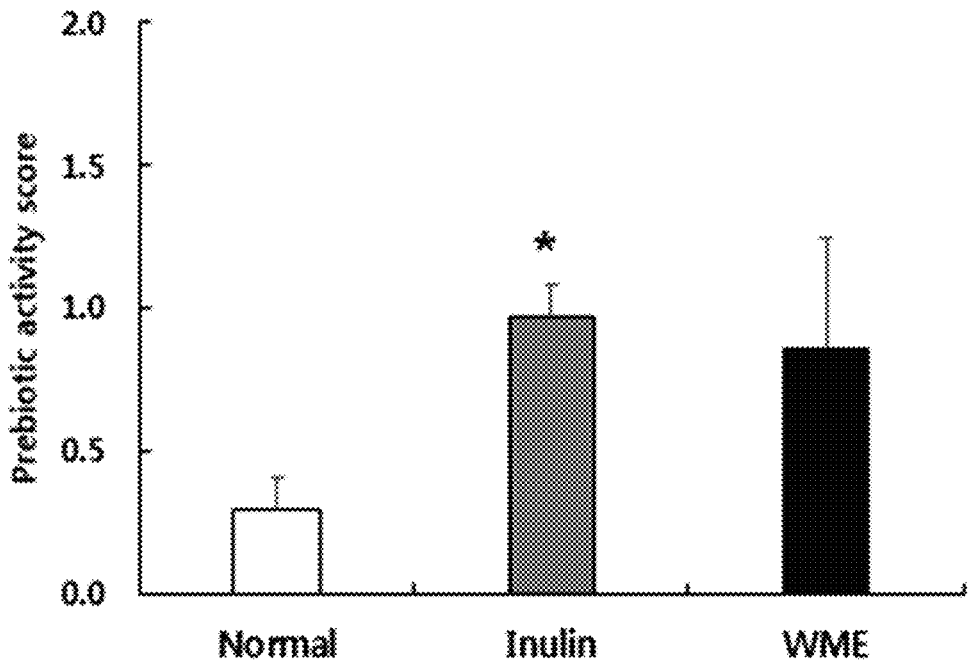
FIGS. 5A to 5D are graphs showing analyses of beneficial bacteria activity (prebiotic activity score) in the intestine by treating *Bacteroides* strains with the hot water extract of Molokhia prepared from Example 1, the Molokhia polymer fraction prepared from Example 2, and inulin.
Figure 5B:
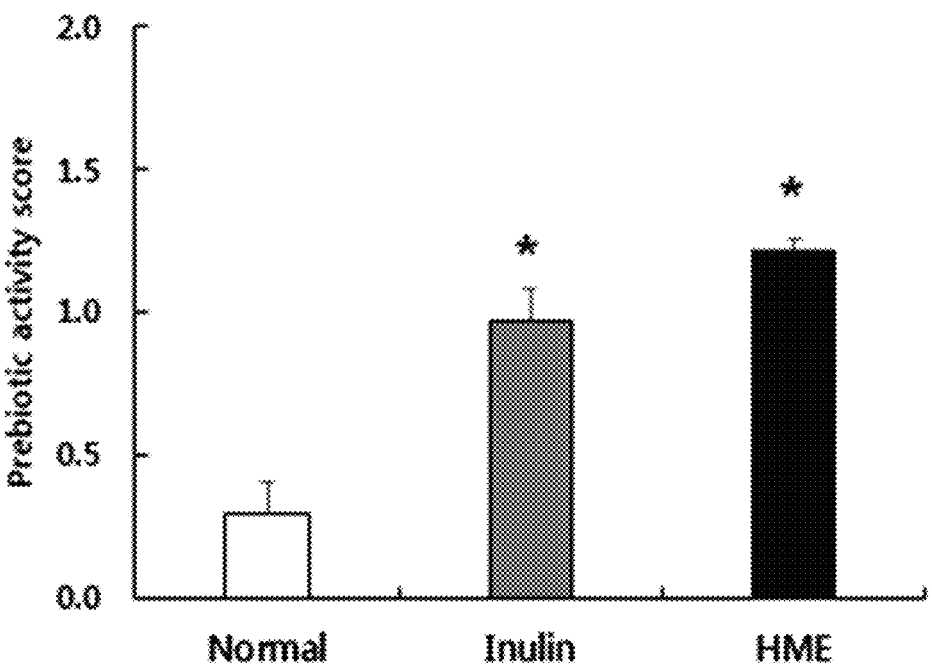
Figure 5C:
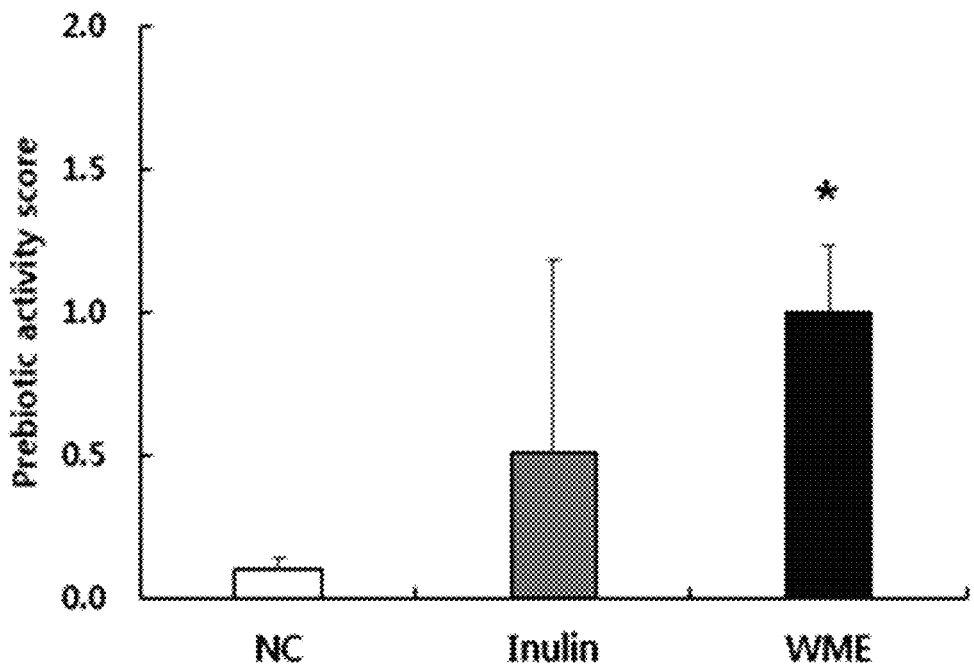

FIGS. 5A and 5C are graphs showing analyses of the activity (prebiotic activity score) of beneficial bacteria in the intestine when *Bacteroides* strains were treated with a hot water extract of Molokhia and inulin. FIG. 5A is for *Bacteroides uniformis*, and FIG. 5C is for *Bacteroides ovatus*.

Each strain was administered with the conventional prebiotic fructo-oligosaccharide or inulin and the hot water extract of Molokhia of Example 1 to confirm the prebiotic activity score. Referring to FIGS. 1A to 1F, it was confirmed that the Molokhia hot water extract of Example 1 according to the present invention exhibited the same or higher activity as compared to the conventional prebiotic fructo-oligosaccharide relative to the majority of beneficial bacteria in the intestine, and suppressed the activity for *E. coli*. It was found that the activity of all beneficial bacteria was higher than most of the control group (up to 3 to 6 times).

The Molokhia hot water extract of the present invention was found to exhibit the highest prebiotic activity score (1.610, 1.316, respectively) for *Lactobacillus plantarum* and *Bifidobacterium longum*. Concretely, it was confirmed to have higher activity (0.5 times increase in a maximum) than the fructo-oligosaccharides (1.139, 0.781, respectively) well known as the conventional prebiotics. The Molokhia hot water extract of the present invention was found to have similar or higher activity to the positive control FOS and all have high activity compared to the control group. Thereamong, it was confirmed that the Molokhia hot water extract of the present invention has a higher prebiotic activity than the conventional prebiotic (fructo-oligosaccharide) for *Lactobacillus plantarum* and *Bifidobacterium longum*.

As shown in FIG. 3A, a comparison of the activities for *Lactobacillus* and *Lactococcus*, except for the anaerobic strain *Bifidobacterium*, indicated that the Molokhia hot water extract of the present invention exhibited similar levels of activity to the FOS. In addition, comparison of the prebiotic activities for the overall beneficial bacteria in the intestine confirmed that the Molokhia hot water extract was 1.046, which was slightly lower than the FOS group (0.039), but increased by about 5 times compared to the case that nothing was treated.

As shown in FIGS. 5A and 5C, the prebiotic activity scores for *Bacteroides uniformis* and *Bacteroides ovatus* indicated 0.86 and 1.00, respectively, which are similar to or higher than inulin. In particular, it was confirmed that the prebiotic activity score for *Bacteroides ovatus* strain showed an increase about 10 times compared to the case where nothing was treated.

Experimental Example 2-2. Analysis of Activity (Prebiotic Activity Score) of Beneficial Bacteria in the Intestine for a Molokhia Polymer Fraction The obtained strains were added 1% (v/v) to M9 medium containing 10 mg/ml of glucose, respectively, to prepare a control group.

Further, *Lactobacillus, Lactococcus* and *Bifidobacterium* strains among the obtained strains were added 1% (v/v) to M9 medium containing 10 mg/ml of fructo-oligosaccharides (FOS), respectively, and *Bacteroides* strains were added 1% (v/v) to M9 medium containing 10 mg/ml of inulin to prepare a positive control group.

The obtained strains were added 1% (v/v) to M9 medium containing 10 mg/ml of the Molokhia polymer fraction (Example 2), respectively, to prepare an experimental group.

Absorbance at 600 nm of each group was measured a microplate reader immediately after inoculation (0 hours) of the strains and 24 hours after inoculation, and these values were substituted into Equation 1 below to determine activity values (prebiotic activity score) of the beneficial bacteria in the intestine.

$$\text{Prebiotic activity score} = \frac{\begin{bmatrix}(\text{probiotic log O.D. on the probiotic at 24 h} - \\ \text{probiotic log O.D. on the probiotic at 0 h})\end{bmatrix}}{(\text{probiotic log O.D. on glucose at 24 h} - \text{probiotic log O.D. on glucose at 0 h})} - \frac{\begin{bmatrix}(\text{enterie log O.D. on the probiotic at 24 h} - \\ \text{enterie log O.D. on the probiotic at 0 h})\end{bmatrix}}{(\text{enterie log O.D. on glucose at 24 h} - \text{enterie log O.D. on glucose at 0 h})} \quad [\text{Equation 1}]$$

In the above equation,

The "probiotic log GD on the prebiotic at 24 h" is an absorbance measured at 600 nm using a microplate reader 24 hours after inoculation of *Lactobacillus, Bifidobacterium* and *Bacteroides* strains in the positive control group or the experimental group.

The "probiotic log O.D. on the prebiotic at 0 h" is an absorbance measured at 600 nm after inoculation of *Lactobacillus, Bifidobacterium* and *Bacteroides* strains in the positive control group or the experimental group, using a microplate reader.

The "probiotic log O.D. on glucose at 24 h" is an absorbance measured at 600 nm using a microplate reader 24 hours after inoculation of *Lactobacillus, Bifidobacterium*, and *Bacteroides* strains in a glucose control group.

The "probiotic log O.D. on glucose at 0 h" is an absorbance measured at 600 nm after inoculation of *Lactobacillus, Bifidobacterium*, and *Bacteroides* strains in the glucose control group, using a microplate reader.

The "enteric log O.D. on the prebiotic at 24 h" is an absorbance measured at 600 nm using a microplate reader 24 hours after inoculation of *E. coli* in the positive control group or the experimental group.

The "enteric log O.D. on the prebiotic at 0 h" is an absorbance measured at 600 nm after inoculating *E. coli* in the positive control group or the experimental group, using a microplate reader.

The "enteric log O.D. on glucose at 24 h" is an absorbance measured at 600 nm using a microplate reader 24 hours after inoculation of *E. coli* in the glucose control group.

The "enteric log O.D. on glucose at 0 h" is an absorbance measured at 600 nm after inoculating *E. coli* in the glucose control group, using a microplate reader.

FIGS. 2A to 2C are graphs showing analyses of beneficial bacteria activity (prebiotic activity score) in the intestine when various bacteria were treated with the Molokhia polymer fraction of Example 2 and a FOS (fructo-oligosaccharide). FIG. 2A is for *Lactobacillus paracasei* ATCC 25302(T) (*Lactobacillus paracasei* subsp. *tolerans*), FIG. 2B is for *Lactobacillus plantarum*, FIG. 2C is for *Lactococcus lactis* NCDO604(T) (*Lactococcus lactis* subsp. *lactis*), FIG. 2D is for *Bifidobacterium longum*, FIG. 2E is for *Bifidobacterium bifidum*, and FIG. 2F is for *Bifidobacterium breve*.

Figure 3B:
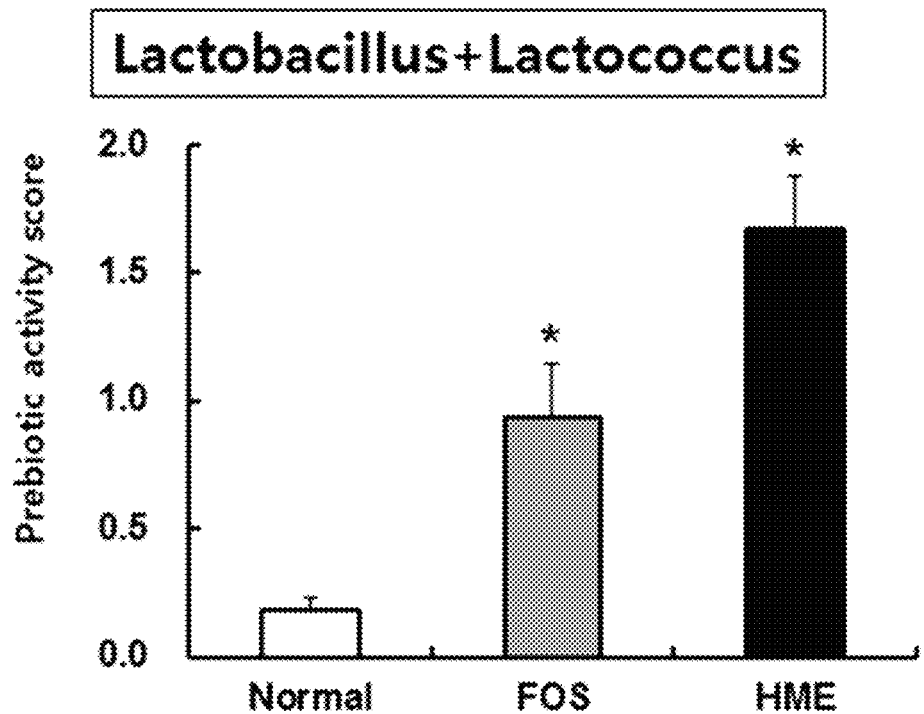
FIG. 3B is a graph showing analysis of an activity (prebiotic activity score) for *Lactobacillus* and *Lactococcus* among beneficial bacteria in the intestine when total bacteria were treated with the Molokhia polymer fraction of Example 2 and a FOS (fructo-oligosaccharide).
Figure 4B:
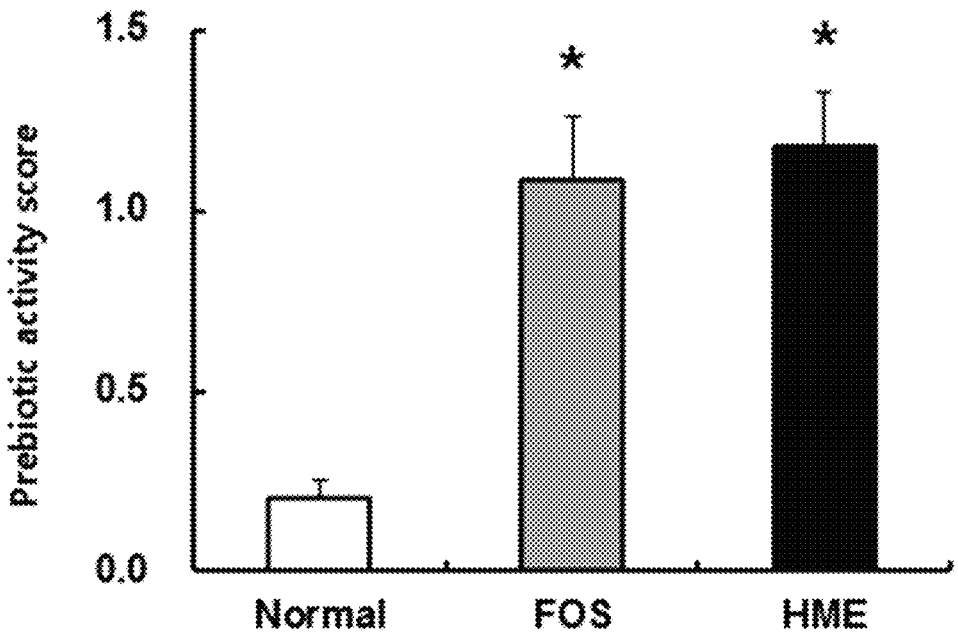
FIG. 4B is a graph showing analysis of beneficial bacteria activity (prebiotic activity score) in the intestine when total bacteria were treated with the Molokhia polymer fraction of Example 2 and a FOS (fructo-oligosaccharide).

FIG. 3B shows an average of the activity (prebiotic activity score) of beneficial bacteria in the intestine for the total strains of a polymer fraction, and FIG. 4B shows an average of the activity (prebiotic activity score) of beneficial bacteria in the intestine for the total strains of the Molokhia polymer fraction of Example 2.

Figure 5D:
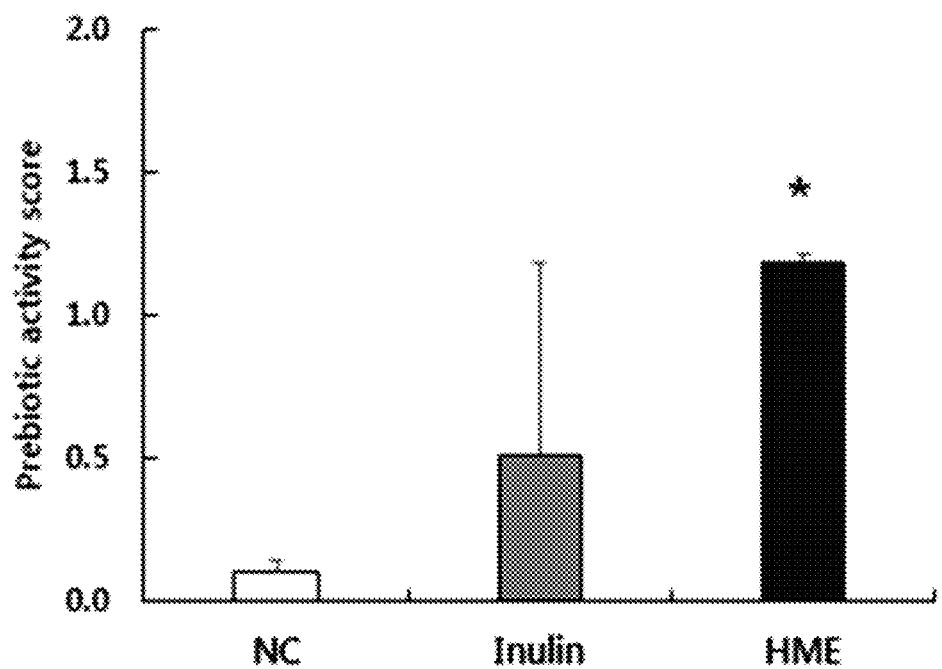

FIGS. 5A and 5C are graphs showing analyses of the activity (prebiotic activity score) of beneficial bacteria in the intestine when *Bacteroides* strains were treated with a Molokhia polymer fraction and inulin. FIG. 5B is for *Bacteroides uniformis*, and FIG. 5D is for *Bacteroides ovatus*.

Each strain was administered with the conventional prebiotic fructo-oligosaccharide or inulin and the Molokhia polymer fraction of Example 2 to confirm the prebiotic activity score. Referring to FIGS. 2A to 2C, it was confirmed that the Molokhia polymer fraction of Example 2 according to the present invention exhibited the same or higher activity as compared to the conventional prebiotic fructo-oligosaccharide relative to the majority of beneficial bacteria in the intestine, and suppressed activity of *E. coli*. It was found that the activity of all beneficial bacteria was higher than most of the control group (up to 3 to 6 times).

It was found that the Molokhia polymer fraction of the present invention was shown to maintain activity of a similar level for the majority of beneficial bacteria when compared to the case the Molokhia hot water extract was treated, but the above activity was 1.094 for *Lactococcus lactis* NCDO604(T) (*Lactococcus lactis* subsp. *lactis*), which was about 1.17 higher than that of the FOS group and about 1.6 higher than that of the hot water extract. In addition, it was confirmed that for *Lactobacillus paracasei* ATCC 25302(T) (*Lactobacillus paracasei* subsp. *tolerans*) and *Lactobacillus plantarum*, the prebiotic activity score of the Molokhia polymer fraction of the present invention was also about 0.4 to 1.17 higher than that of the FOS group. It was confirmed that the Molokhia polymer fraction of the present invention significantly increased the prebiotic activity score for the lactic acid bacteria group compared to the Molokhia extract.

As shown in FIG. 3B, a comparison of the activities for *Lactobacillus* and *Lactococcus*, except for the anaerobic strain *Bifidobacterium*, indicated that the Molokhia polymer fraction of the present invention had a prebiotic activity score which was increased 1.5 times or more than that of the FOS.

Furthermore, a comparison of the prebiotic activities for the overall beneficial bacteria in the intestine confirmed that the prebiotic activity of the Molokhia polymer fraction was 1.046, which was slightly lower than that (0.039) of the FOS group, but was remarkably increased compared to the case where nothing was treated.

Taking the above results together, it can be confirmed that In the case of the Molokhia polymer fraction, an ability to increase the prebiotic activity for beneficial bacteria such as *Lactobacillus* and *Lactococcus*, which are anaerobic strains, is remarkably superior to the FOS by 1.5 times or more. In addition, it can be seen that the Molokhia hot water extract contains parts other than the polymer fraction and thus only shows a level of the prebiotic activity moderate to that of the FOS for the beneficial bacteria such as *Lactobacillus* and *Lactococcus*, which are anaerobic strains, but overall exhibits an effect similar to that of the FOS (positive control group) for the total beneficial bacteria in the intestine including Bifidobacteria. In other words, it is believed that in case other components are mixed in the polymer fraction, the proliferation and promotion effect of the beneficial bacteria such as *Lactobacillus*, *Lactococcus*, etc., which are anaerobic strains, is deteriorated due to complex action therebetween. Therefore, in order to obtain a desired purpose or effect, it may be appropriately selected and used from the hot water extract and the polymer fraction.

As shown in FIGS. 5B and 5D, the prebiotic activity scores for *Bacteroides uniformis* and *Bacteroides ovatus* indicated 1.22 and 1.18, respectively, which were about 1.25 and 2.31 times higher than that of the inulin group.

Experimental Example 3. Analysis of Harmful Enzyme Activity for the Hot Water Extract of Example 1

Experimental Example 3-1. An Experimental Animal

First, 45 6-week-old male C57BL/6J mice were purchased from Central Experimental Animal Co., Ltd. The experimental animals were divided into five groups as follows. Nine experimental animals were used for each group, and after 8 weeks of diet, an inhibitory effect of harmful enzyme activity was evaluated.

Normal feed group (NC): An experimental group that was fed a Normal feed (AIN-93G) and administered only a vehicle orally;

High-fat diet group (HF): an experimental group that was fed a high fat (a fat of 60% kcal) feed and administered only a vehicle orally;

Garcinia-administered group (GG): an experimental group that was fed a high-fat feed and administered 50 mg/kg of garcinia extract orally;

Administration group (WME50) of Molokhia extract of 50 mg/kg: an experimental group that was fed a high-fat feed and administered 50 mg/kg of Molokhia hot water extract orally;

Administration group (WME100) of Molokhia extract of 100 mg/kg: an experimental group that was fed a high-fat feed and administered 100 mg/kg of Molokhia hot water extract orally.

Experimental Example 3-2. Analysis of Harmful Enzyme Activity

After the 8-week diet period was over, fresh feces from the mice were obtained for each group. 1 g of the obtained feces was suspended in a cold physiological saline to obtain a precipitate, which was suspended in 0.1 M potassium phosphate buffer and used as an enzyme solution. For analysis of β-glucuronidase activity, 100 μL of the enzyme solution, 380 μL of 0.1M potassium phosphate buffer, and 20 μL of p-nitrophenyl-β-glucuronide as a substrate were reacted at 37° C. for 60 minutes, and then 500 μL of 0.5 N NaOH was added thereto and a centrifugation was performed at 3,000×g for 10 minutes. Thereafter, a supernatant was taken to measure an absorbance at 405 nm using p-nitrophenol as a standard curve. For an analysis of β-glucosidase activity, 50 μL of the enzyme solution, 350 μL of 0.1M potassium phosphate buffer, and 100 μL of p-nitrophenyl-β-glucopyranoside as a substrate, were reacted at 37° C. for 60 minutes, and then 400 μL of 0.5 N NaOH was added thereto and a centrifugation was performed at 3,000×g for 10 minutes. Thereafter, a supernatant was collected to measure an absorbance at 405 nm using p-nitrophenol as a standard curve. For analysis of tryptophanase activity, a complete reaction mixture (4% pyridoxal 5-phosphate, 20% bovine serum albumin in 0.1M bicine, pH 8.0), 0.2 mL of 0.02M tryptophan, and 0.1 mL of the enzyme solution were reacted at 37° C. for 60 minutes, and then 2 mL of a color reagent (14.7 g of ρ-dimethyl aminobenzaldehyde, 948 mL of 95% ethanol, 52 mL of $CH_2SO_4$) were added thereto to terminate the reaction. Thereafter, a supernatant was collected by centrifugating the reactants at 3,000×g for 10 minutes to measure an absorbance at 550 nm using indole as a standard curve.

Figure 6A:
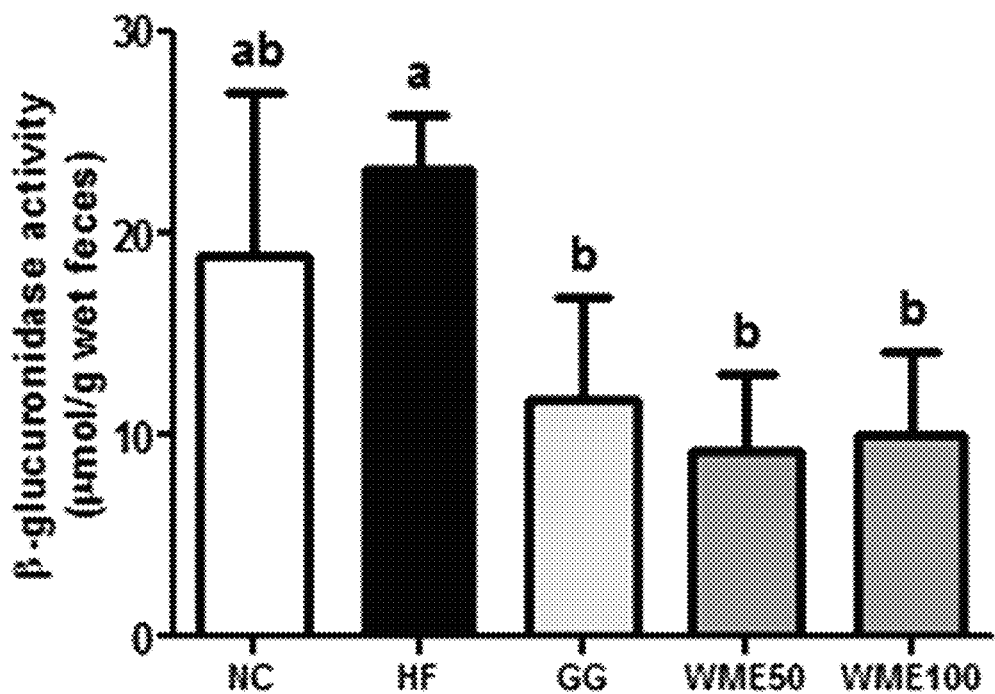
FIGS. 6A to 6C are graphs showing analyses of harmful enzyme activity of the intestinal microflora when the hot water extract of Molokhia of Example 1 and Garcinia Gummi-gutta extract (GG) as a positive control group were administered to mice subjected to a high-fat diet.
Figure 6B:
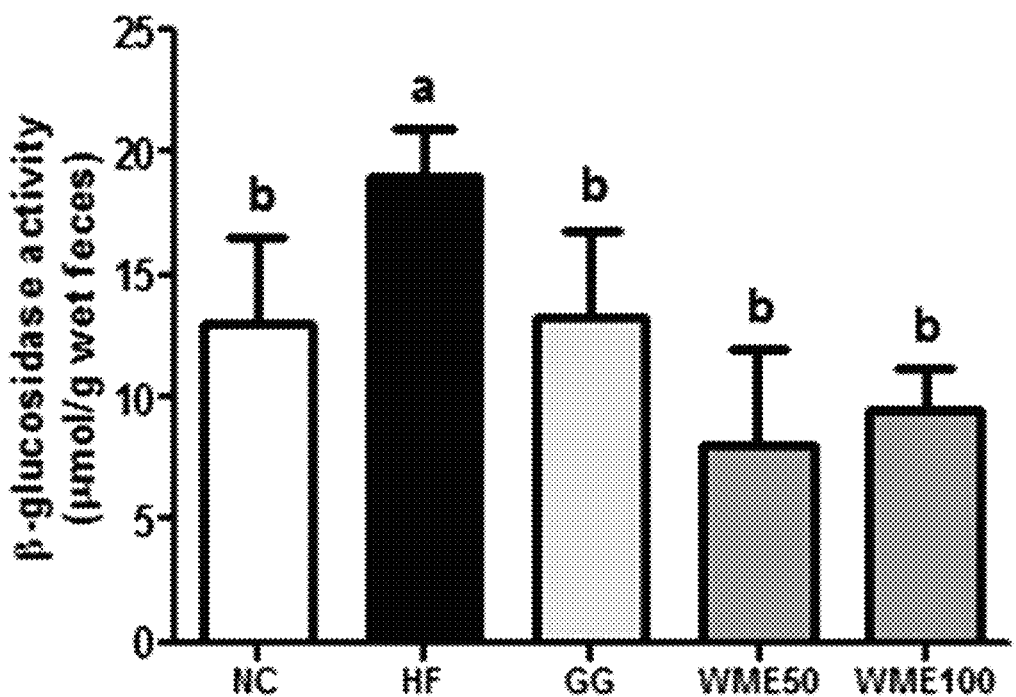
Figure 6C:
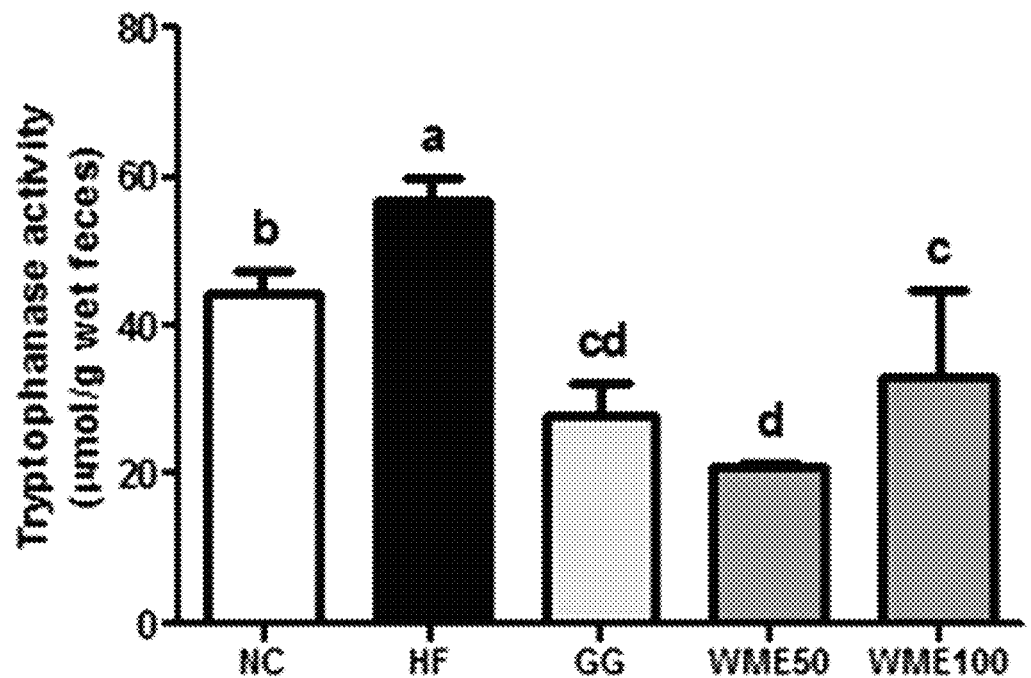

FIGS. 6A to 6C are graphs showing analyses of harmful enzyme activity of the intestinal microflora when the hot water extract of Molokhia of Example 1 and Garcinia Gummi-gutta extract (GG) as a positive control group were administered to mice subjected to a high-fat diet. FIG. 6A shows a result of β-glucuronidase activity, FIG. 6B shows a result of β-glucosidase activity, and FIG. 6C shows a result of tryptophanase activity. It is important to suppress harmful enzymes produced by harmful intestinal microflora because they help toxins to penetrate into the gastrointestinal tract. β-glucuronidase activity was found to be reduced by about 60% and 56% compared to the high-fat diet group when the Molokhia hot water extracts were administered in concentrations of 50 mg/kg and 100 mg/kg, which were decreased by about 21% and 14% compared to the activity of the positive control group. It was confirmed that β-glucosidase activity was inhibited by about 58% and 51% compared to the high-fat diet group when the Molokhia hot water extracts were administered in concentrations of 50 mg/kg and 100 mg/kg, which were suppressed by about 40% and 29% compared to the activity of the positive control group. It was confirmed that tryptophanase activity was inhibited by about 63% and 41% compared to the high-fat diet group when the Molokhia hot water extracts were administered in concentrations of 50 mg/kg and 100 mg/kg, which had a similar efficacy to the positive control group.

Taking the above results together, it was confirmed that the Molokhia hot water extract had an effect of inhibiting harmful enzymes compared to the group that proceeded with only a high-fat diet, which showed the inhibitory efficacy similar to or higher than the garcinia (positive control group).

Experimental Example 4. Efficacy of Inhibiting Inflammation for Each Part of Molokhia Extract In order to investigate inhibitory activity on NO production for each part of Molokhia extracts (Example 1, Comparative Examples 1 and 2), RAW 264.7 cells (1×10⁶/mL) were first cultured in DMEM and were stimulated for 24 hours by adding 5 μg/ml or 10 μg/ml of the Molokhia extracts for each part together with LPS (1 μg/mL). A concentration of NO was investigated by measuring an amount of nitrite in the cell culture supernatant according to the manufacturer's instructions using a Griess reagent (Sigma, USA). The cultured RAW 264.7 cells were mixed with 150 μL of the cell culture supernatant and 150 μL of the Griess reagent, centrifuged at 1,000×g for 10 minutes, and then incubated at a room temperature for 10 minutes. Absorbance was measured at 540 nm using a microplate reader, and compared on the basis of a calibration curve formed through sodium nitrite. In this case, the control group was treated with PBS buffer only.

Figure 7:
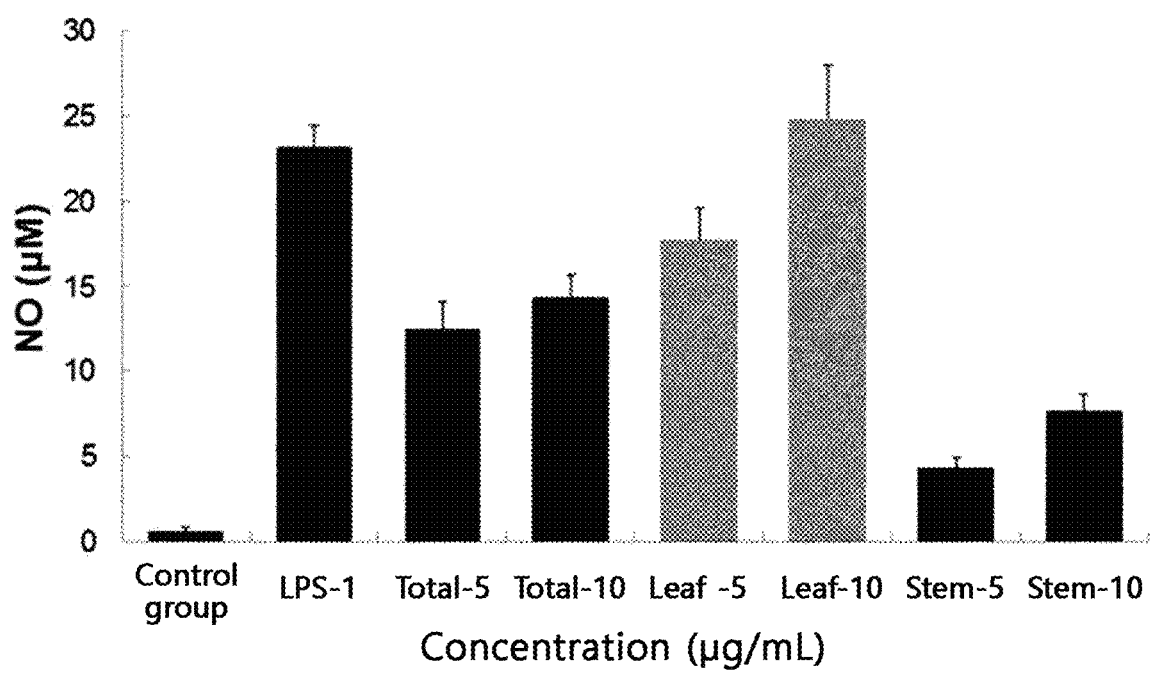
FIG. 7 is a graph showing measurement of a concentration of a NO in RAW 264.7 cells treated with extracts (Example 1, and Comparative Examples 1 and 2) for each part of Molokhia.

FIG. 7 is a graph showing measurement of a concentration of NO in RAW 264.7 cells treated with the extracts (Example 1, and Comparative Examples 1 and 2) for each part of Molokhia.

As shown in FIG. 7, NO production activity for each part of the Molokhia extracts was highest in the Molokhia leaf extract. Nitric oxide (NO) plays a very important role in regulating blood pressure in the human body, neurotransmitting, and maintaining homeostasis of the immune process. In particular, NO is known as an essential endogenous substance for the human body's defense mechanism against microbial infection (Bogdan, 2001). Therefore, when treated with an inflammatory mediator such as LPS, the Molokhia hot water extract of Example 1 among the overall Molakhia sites greatly increased NO production in a macrophage, and thus, it can be seen that the Molokhia hot water extract is most effective in enhancing immune activity.

Experimental Example 5. Analysis of Yield of the Molokhia Hot Water Extract of Example 1 and the Molokhia Polymer Fraction of Example 2, and Contents of Sugar and Protein Neutral sugar was hydrolyzed by partially modifying a method of Albersheim et al. to derivatize each compositive sugar with alditol acetate and aldonolactone, and then analyzed using a GC (Gas Chromatography ACME-6100, Young-Lin Co. Ltd., Anyang, Korea). The samples of Example 1 and Example 2 were hydrolyzed by reacting them in 2 M TFA (trifluoroacetic acid) at 121° C. for 1.5 hours, and then dissolved in 1 ml of 1 M NH₄OH (ammonia solution) and reduced in 10 mg of NaBH₄ for 4 hours. An appropriate amount of acetic acid was added to remove the residual NaBH₄, followed by repeatedly drying with methanol to remove excess acetic acid, which was converted into alditol. 1 ml of acetic anhydride was added to the alditol and reacted at 121° C. for 30 min to convert the same into alditol acetate, which was separated and extracted with a solvent system of chloroform/H₂O 2-phases. The extract was dried, and then dissolved in a small amount of acetone for use as a sample for GC analysis.

A quantity of protein was measured according to the Bradford method, and BSA (Bovine Serum Albumin, Sigma Aldrich) was used as a standard and diluted at a constant multiple with 1 mg/ml as the highest concentration. After adding 20 μl of each standard and sample to 980 μl of a Bradford reagent, Absorbance was measured at 595 nm using a microplate reader. The quantity of protein was converted into an amount for the BSA.

Total sugar was measured according to a phenol-sulfuric acid method. After adding to 0.5 mL of the sample solution the equal amount of 5% phenol solution and stirring, 2.5 mL of concentrated sulfuric acid (98%, v/v) was added and reacted at a room temperature for 20 minutes to measure Absorbance at 470 nm using a microplate reader. A quantity of the total sugar was converted into an amount for a glucose standard (Sigma Aldrich) by preparing a calibration curve with the glucose standard.

A content of the total polyphenol was analyzed according to a Folin Denis method using a gallic acid (Sigma Aldrich).

In the case of the compositive sugar, sugar chains of the sample were hydrolyzed to monosaccharide, and then analyzed using HPAEC-PAD (high-performance anion-exchange chromatography-pulsed amperometric detector). The resulting data were analyzed using Chromelon 6.80 software (Dionex). The monosaccharide (fucose, rhamnose, arabinose, galactose, glucose, xylose) was used as a standard solution.

As a result, physicochemical characteristics analyzing main ingredients and contents of the Molokhia hot water extract and the Molokhia polymer fraction are shown in Table 2 below.

The results that analyzed the physicochemical characteristics such as contents of main ingredients of the hot water extract of Molokhia prepared from Example 1 and the Molokhia polymer fraction prepared from Example 2 are shown in Table 2 below.

TABLE 2

| Classification | Example 1(WEML) | Example 2(HEML) |
|---|---|---|
| Extraction yield(%) | 29.98 | 1.90 |
| Chemical composition(%) | | |
| Protein | 2.8 ± 0.1 | 3.2 ± 0.7 |
| Neutral sugar | 67.6 ± 2.0 | 47.1 ± 1.3 |
| Uronic acid | 18.8 ± 0.8 | 44.7 ± 1.3 |
| KDO-liked material | 0.5 ± 0.3 | 1.4 ± 1.0 |
| Polyphenol | 12.2 ± 0.2 | 3.6 ± 0.8 |
| Compositive sugar(PMP)(Mole %) | | |
| Rhamnose | 10.1 ± 0.1 | 22.4 ± 0.5 |
| Fucose | — | 0.3 ± 0.1 |
| Arabinose | 4.0 ± 0.0 | 5.3 ± 0.0 |
| Xylose | 1.2 ± 0.1 | 1.2 ± 0.0 |
| Mannose | 2.2 ± 0.0 | 0.3 ± 0.0 |
| Galactose | 8.5 ± 0.0 | 11.5 ± 0.2 |
| Glucose | 40.9 ± 0.2 | 2.1 ± 0.0 |
| Glucuronic acid | 9.0 ± 0.1 | 20.1 ± 0.1 |
| Galacturonic acid | 10.9 ± 0.0 | 28.5 ± 0.7 |

The content ratios (%) of the chemical composition represents % by weight in a dry sample.

As shown in Table 2, it was confirmed that the hot water extract of Molokhia prepared from Example 1 had a yield of 29.98%, a protein content of 2.8% by weight, and a neutral sugar content of 67.6% by weight. That is, most of the hot water extracts of Molokhia of Example 1 were analyzed to be occupied by a sugar.

As a result of analyzing the compositive sugars of the Molokhia hot water extract prepared from Example 1, the main compositive sugar was glucose (40.9%), and galacturonic acid, rhamnose, glucuronic acid and galactose were found to be present in 10.9 Mole %, 10.1 Mole %, 9.0 Mole % and 8.5 Mole %, respectively. In addition, arabinose, mannose and xylose were present in trace amounts of 4.0 Mole %, 2.2 Mole % and 1.2 Mole %, respectively.

It was confirmed that an extraction yield of the Molokhia polymer fraction was 1.9%, the protein content was 3.2%, the neutral sugar content was 47.1%, and the highest uronic acid content was 44.7%. As the main compositive sugars, galacturonic acid, rhamnose and glucuronic acid were detected to be 28.5%, 22.4% and 20.1%, respectively, and galactose, arabinose, glucose, xylose, fucose and mannose were detected to be 11.5%, 5.3%, 2.1%, 1.2%, 0.3% and 0.3%, respectively.

Experimental Example 6. Analysis of Inflammation-Related Factors of the Molokhia Hot Water Extract of Example 1

1) Experimental Animals

First, 45 6-week-old male C57BL/6J mice were purchased through Central Experimental Animal Co., Ltd. The experimental animals were divided into five groups as follows. Nine experimental animals were used for each group, and after 8 weeks of diet, intestinal immune regulation efficacy was evaluated.

Normal feed group (NC): An experimental group that was fed a normal feed (AIN-93G) and administered only a vehicle orally;

High-fat diet group (HFD): an experimental group that was fed a high fat (a fat of 60% kcal) feed and administered only a vehicle orally;

Positive control group (GC): an experimental group that was fed a high-fat feed and administered 50 mg/kg of Garcinia cambogia extract orally;

First experimental group (WEML50): an experimental group that was fed a high-fat feed and administered 50 mg/kg of the Molokhia hot water extract prepared from Example 1 orally;

Second experimental group (WEML100): an experimental group that was fed a high-fat feed and administered 100 mg/kg of the Molokhia hot water extract prepared from Example 1 orally.

In this case, the high fat data used a modified AIN 76A purified rodent diet (60 cal % fat) that increased a caloric value by 60 cal % by adding lard.

2) Analysis

After the 8-week diet period was over, the experimental animals of each group were fasted for 6 hours before analysis. Next, the experimental animals were anesthetized and their abdomens were opened. After collecting blood from the inferior vena cava using a sterile syringe, it was stored in a sterile tube treated with heparin. The obtained blood was centrifuged (12,000×g, 10 minutes, 4° C.) and a supernatant was taken and used for analysis. Concentrations of immunoglobulin A, IL-6, and leukotriene B4 in blood were quantified using Mouse IgA ELISA kit (Abcam, ab157717), Mouse IL-6 Quantikine ELISA kit (R&D systems, M6000B), and LTB4 Parameter Assay Kit (R&D systems, KGE006B), respectively.

3) Analysis Result

Figure 8:
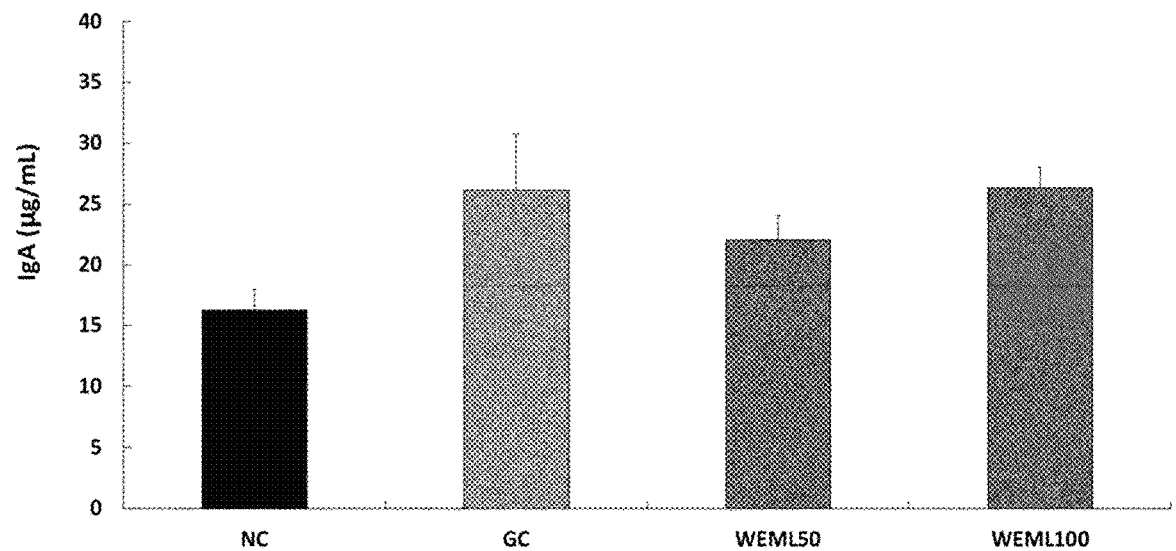
FIG. 8 is a graph showing measurement of a concentration of IgA in serum for a normal feed group (NC), a positive control group (GC), a first experimental group (WEML50), and a second experimental group (WEML100).
Figure 9:
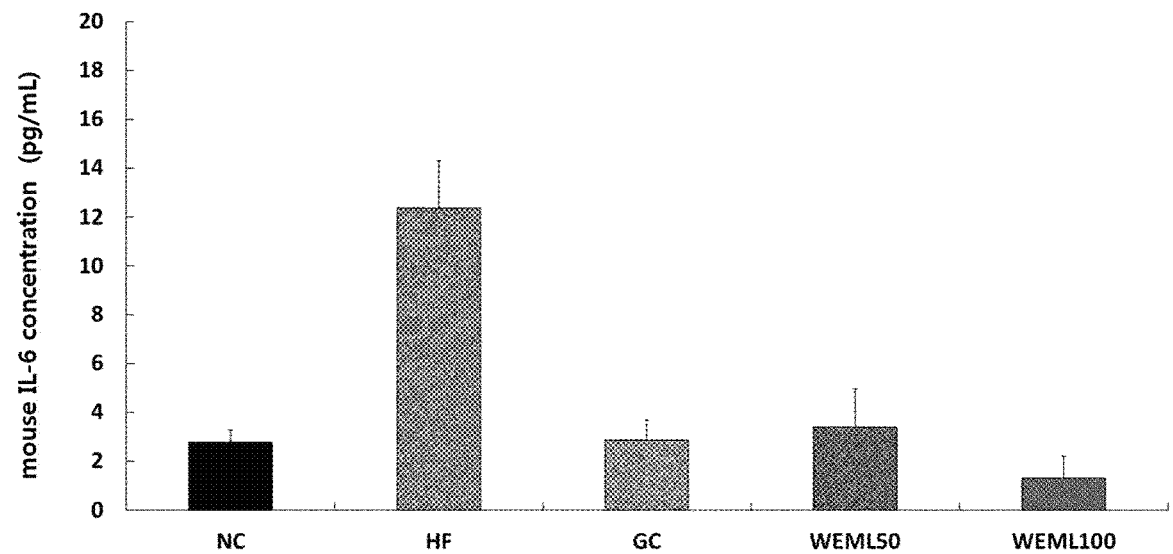
FIG. 9 is a graph showing measurement of expression levels of cytokine IL-6 in serum for a normal feed group (NC), a high-fat diet group (HF), a positive control group (GC), a first experimental group (WEML50), and a second experimental group (WEML100).
Figure 10:
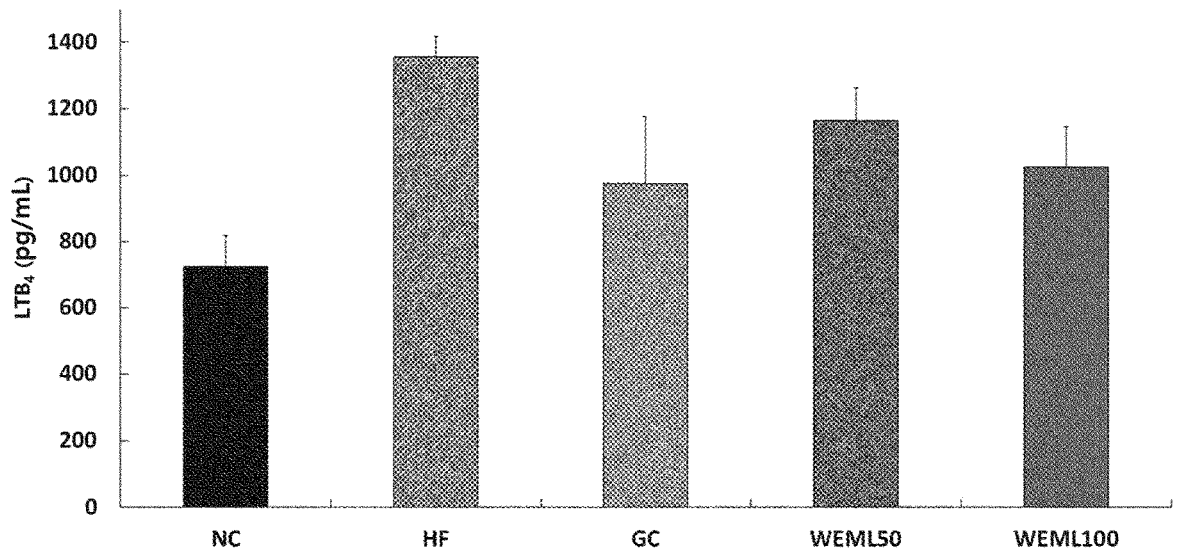
FIG. 10 is a graph showing measurement of expression levels of cytokine leukotriene B4 (LTB4) in serum for a normal feed group (NC), a high-fat diet group (HF), a positive control group (GC), a first experimental group (WEML50), and a second experimental group (WEML100).

Intestinal inflammation-related indicators for the Molokhia hot water extract prepared from Example 1 were confirmed, and the results are shown in FIGS. 8 to 10.

FIG. 8 is a graph showing measurement of a concentration of IgA in a serum for a normal feed group (NC), a positive control group (GC), a first experimental group (WEML50), and a second experimental group (WEML100). As shown in FIG. 8, the IgA concentration in blood was 16.25 μg/ml for normal feed group (NC), but was 26.17 μg/ml for the positive control group (GC), which indicated that intestinal immunity activity was increased. It was confirmed that the IgA concentration in blood was 22.09 μg/ml for the first experimental group in which the Molokhia hot water extract prepared from Example 1 was orally administered in a concentration of 50 mg/kg. In addition, 26.33 μg/ml of IgA was detected for the second experimental group in which the Molokhia hot water extract prepared from Example 1 was orally administered in a concentration of 100 mg/kg.

In summary, it can be seen that the Molokhia hot water extract of Example 1 also enhances the intestinal immune activity like the positive control group (GC). In particular, since it was confirmed that the intestinal immunity activity was also increased as the administration concentration of the Molokhia hot water extract (Example 1) was increased, it can be seen that the Molokhia hot water extract according to the present invention has an effect of reducing inflammation by enhancing the immune activity in the intestine.

FIG. 9 is a graph showing measurement of expression levels of cytokine IL-6 in a serum for a normal feed group (NC), a high-fat diet group (HF), a positive control group (GC), a first experimental group (WEML50), and a second experimental group (WEML100).

IL-6 is a representative cytokine known to be increased in inflammatory bowel disease. The present invention tried to investigate an effect of preventing or treating inflammatory bowel disease by mixing and administering the Molokhia hot water extract of Example 1 while inducing inflammatory bowel disease through a long-term high-fat diet for 8 weeks. As shown in FIG. 9, it can be seen that a concentration of the IL-6 was significantly increased to 12.37 μg/ml in the high-fat diet group (HF) in which the inflammatory bowel disease was induced through a high-fat diet for 8 weeks. In the first and second experimental groups in which the high-fat diet and the Molokhia hot water extract of Example 1 were co-administered at various concentrations, 3.41 μg/ml and 1.32 μg/ml of IL-6 were detected, respectively. These are the numerical values that are lower than a concentration of IL-6 (2.89 μg/ml) in the positive control group (GC) which was co-administered Garcinia cambogia extract known to have a therapeutic effect on inflammatory bowel disease, and are lower than a concentration of normal feed group (NC) (2.78 μg/ml). That is, it can be seen that the Molokhia hot water extract prepared from Example 1 inhibits production of IL-6 significantly more than normal feed group or the Garcinia cambogia extract. From this, it can be seen that the Molokhia hot water extract according to the present invention has an effect of alleviating, preventing or treating inflammatory bowel disease by suppressing inflammatory reaction in the intestine. The Garcinia cambogia is known to have various side effects such as xerostomia, dizziness, headache or diarrhea when ingested, but the Molokhia hot water extract according to the present invention has a great advantage in that it is a food that can be consumed on a daily basis and has no side effects, and is a stable substance in which toxicity is not detected at all in a cytotoxicity experiment.

FIG. 10 is a graph showing measurement of expression levels of cytokine leukotriene B4 (LTB4) in a serum for a normal feed group (NC), a high-fat diet group (HF), a positive control group (GC), a first experimental group (WEML50), and a second experimental group (WEML100).

Leukotriene B4 (LTB4) is known to be involved in activity of inflammatory cells by inducing an inflammatory response in immune cells. Therefore, a level of inflammation was analyzed by measuring a concentration of the LTB4 from experimental animals in which inflammatory bowel disease was developed by a long-term high-fat diet. As shown in FIG. 10, when the inflammatory bowel disease was developed through the high-fat diet, it can be seen that a concentration of LTB4 was significantly increased to 1357 μg/ml compared to normal feed group (NC). Contrary to this, the concentration of LTB4 was found to be decreased to 976 µg/ml in the positive control group (GC) in which Garcinia cambogia extract was administered concurrently with the high-fat diet.

It was also confirmed that the concentrations of LTB4 were decreased to 1165 µg/ml and 1025 µg/ml, respectively, in the first and second experimental groups in which the Molokhia hot water extract prepared from Example 1 was co-administered the high-fat diet.

Further, the Molokhia hot water extract according to the present invention showed LTB4 concentration reduction having a level similar to the positive control group and normal feed group. From this, it can be seen that the Molokhia hot water extract has an effect of inhibiting LTB4 production of a level equivalent to that of the Garcinia cambogia extract.

Although the first and second experimental groups to which the Molokhia hot water extract was administered had the LTB4 concentration of a decrease level smaller than the positive control group, the Garcinia cambogia extract had a problem that various side effects could be caused, whereas it can be seen that the Molokhia hot water extract of the present invention has a remarkably excellent effect in that it is a very stable substance, and exhibits remarkable anti-inflammatory activity without any cytotoxicity.

The Molokhia hot water extract according to the present invention was found to exhibit an effect of alleviating, preventing or treating inflammatory bowel disease by inhibiting activity of inflammatory cells. Furthermore, in order to obtain a remarkable activity of inhibiting the LTB4 production to a level of normal feed group, the Molokhia hot water extract is preferably administered in a concentration of 100 mg/ml.

Experimental Example 7. Effect of Molokhia Hot Water Extract for Alleviating, Preventing or Treating Leaky Gut Syndrome 1) Experimental animals First, 45 6-week-old male C57BL/6J mice were purchased from Central Experimental Animal Co., Ltd. The experimental animals were divided into five groups as follows. Nine experimental animals were used for each group, and after 8 weeks of diet, alleviation, prevention and treatment efficacy for leaky gut syndrome was evaluated.

Normal feed group (NC): An experimental group that was fed a normal feed (AIN-93G) and administered only a vehicle orally;

High-fat diet group (HFD): an experimental group that was fed a high-fat (a fat of 60% kcal) feed and administered only a vehicle orally;

Positive control group (GC): an experimental group that was fed a high-fat feed and administered 50 mg/kg of Garcinia cambogia extract orally;

First experimental group (WEML50): an experimental group that was fed a high-fat feed and administered 50 mg/kg of the Molokhia hot water extract prepared from Example 1 orally;

Second experimental group (WEML100): an experimental group that was fed a high-fat feed and administered 100 mg/kg of the Molokhia hot water extract prepared from Example 1 orally.

2) Analysis

After the 8-week diet period was over, the experimental animals of each group were fasted from 6 hours before analysis. In order to investigate an intestinal permeability from each experimental animal, FITC-dextran 400 mg/kg body weight dissolved in sterile saline was administered orally, followed by collecting blood of a caudal vein 0, 2 and 4 hours later. 100 µL of the obtained blood was centrifuged (12,000×g, 10 min, 4° C.) to collect a supernatant, and Absorbance of the supernatant was measured by setting an excitation wavelength to 485 nm and an emission wavelength to 535 nm, using a microplate reader. The concentration was calculated using a standard curve of FITC-dextran, and the concentration of FITC-dextran for each time period was expressed as an area under the curve (AUC).

3) Analysis Result

Figure 11:
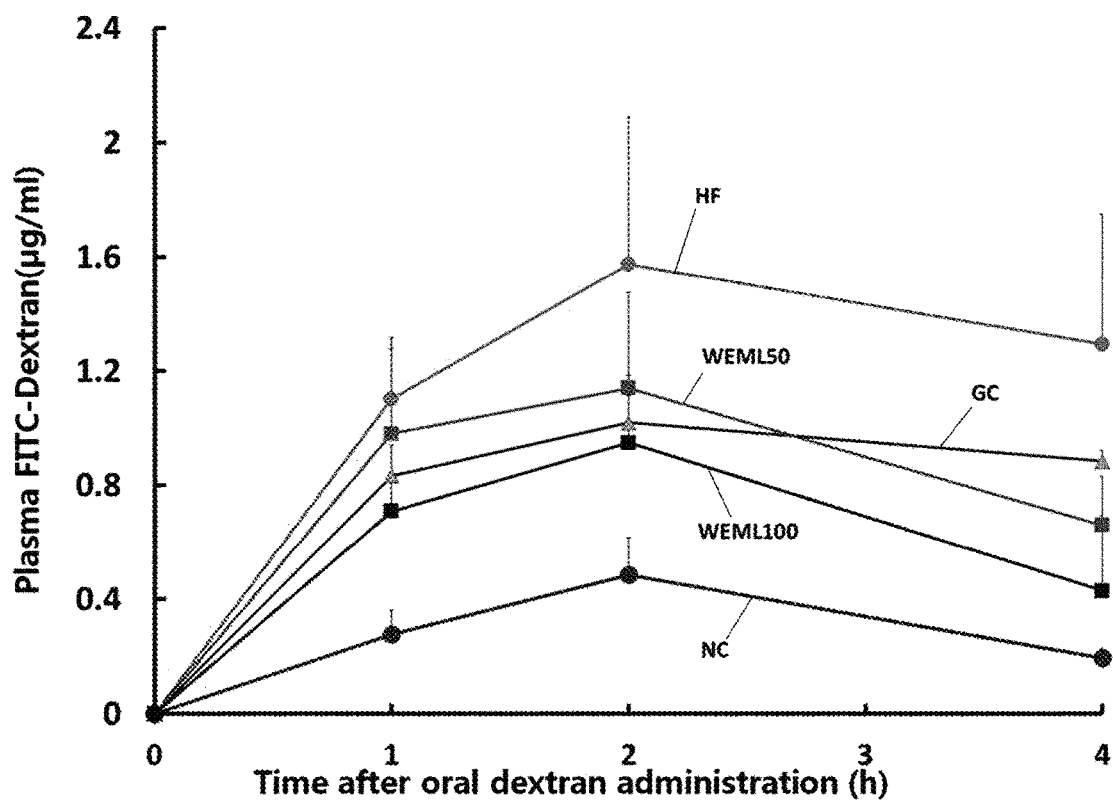
FIG. 11 is a graph showing measurement of a detected concentration of FITC-dextran over time in a normal feed group (NC), a high-fat diet group (HFD), a positive control group (GC), a first experimental group (WEML50), and a second experimental group (WEML100).
Figure 12:
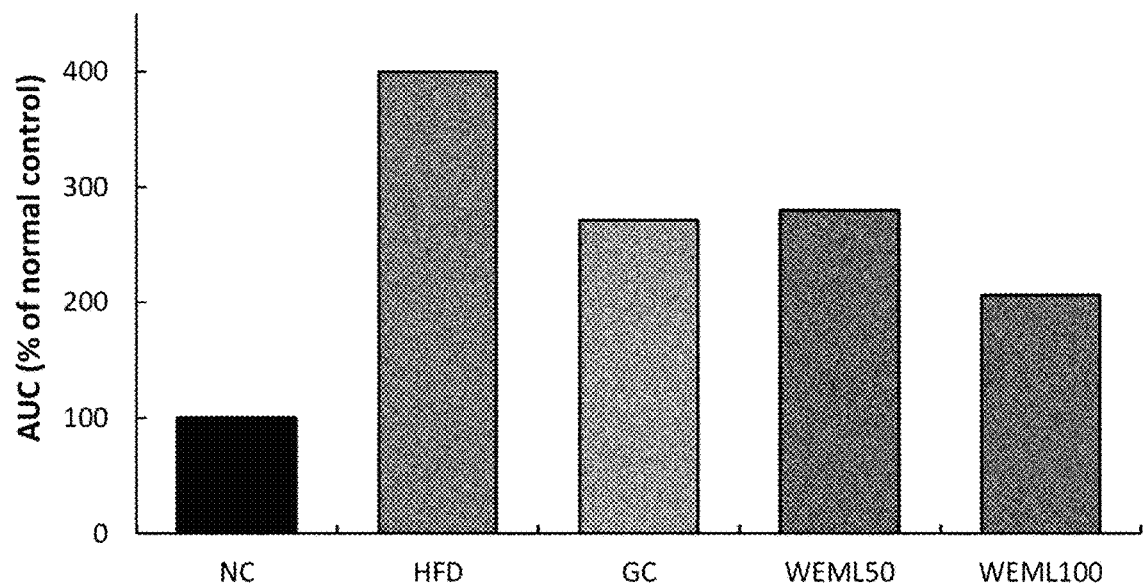
FIG. 12 is a graph showing an area under the curve calculated from the result measured by FIG. 11.

FIG. 11 is a graph showing measurement of a detected concentration of FITC-dextran over time for a normal feed group (NC), a high-fat diet group (HFD), a positive control group (GC), a first experimental group (WEML50), and a second experimental group (WEML100). FIG. 12 is a graph showing an area under the curve calculated from the result measured by FIG. 11.

As shown in FIGS. 11 and 12, when normal feed group (NC) (Normal control group) was set to 100%, the high-fat diet group (HFD) suffering from the leaky gut syndrome by the high-fat diet was detected as 399.61%, and the positive control group (GC) was detected as 271.71%. That is, it can be seen that even if the high-fat diet was provided, intestinal permeability was suppressed when Garcinia cambogia extract was co-administered.

However, the first and second experimental groups to which the Molokhia hot water extract prepared from Example 1 was co-administered was measured as 280.18% and 206.06%, respectively, which demonstrates that the intestinal permeability was suppressed and decreased to the numeral value that was quite similar to that of normal feed group. In particular, it was confirmed that the Molokhia hot water extract prepared from Example 1 was administered to 100 mg/kg or more to exhibit the best effect.

The intestinal permeability was reduced by 2 times in the first and second experimental groups, respectively, compared to the high-fat diet group (HFD). Therefore, it can be seen that the Molokhia hot water extract according to the present invention has an effect for alleviating, preventing, or treating the leaky gut syndrome.

Experimental Example 8. Analysis of Efficacy of Inhibiting Total Fat Cell Differentiation and Fat Accumulation It was attempted to confirm whether the Molokia hot water extract of Example 1 and the Molokia polymer fraction of Example 2 had an effect of inhibiting obesity.

(1) Cell Cultivation

For the experiment, 3T3-L1 total fat cells were sold from the American Type Culture Collection (ATCC), and were cultured under conditions of 37° C. and 5% $CO_2$ using DMEM (Dulbecco's Modified EaDCRT Media (Gibco BRL)) containing 10% fetal bovine serum (FBS) and 1% penicillin/streptomycin (Gibco BRL, Grand Island, NY, USA). In order to solve an over-density phenomenon caused by proliferation of the number of cells, the growth media were exchanged every 48 hours to maintain an appropriate number of cells.

(2) Differentiation Induction

3T3-L1 cells were dispensed into a 6-well plate at a density of $0.8×10^5$ cells/well, and subcultured with 0.05% Trypsin-EDTA every 48 hours. To induce differentiation into fat cells, they were cultured for 48 hours in the DMEM differentiation media to which MDI (0.5 mM 3-isobutyl-1-methylxanthin (IBMX), 1 µM dexamethasone, 10 µg/mL insulin) and 10 vol % fetal bovine serum (FBS) were added. Thereafter, the cultivation was continuously performed until the differentiation was completed while exchanging every 2 days with the media (DMEM) containing only 10 µg/mL of insulin. In order to confirm an influence of the Molokhia hot water extract and the Molokhia polymer fraction on the process of adipogenesis, 50 µg/ml (WEML-50) and 100 µg/ml (WEML-100) of the Molokhia hot water extracts of Example 1, 50 µg/ml (HFML-50) and 100 µg/ml (HFML-100) of the Molokhia polymer fractions of Example 2, and 50 µg/ml (GC-50) and 100 µg/ml (GC-100) of the Garcinia cambogia extracts of Comparative Example 3 were treated together every time the media were exchanged.

When the media were exchanged, the control group (C) was treated together with MDI (0.5 mM 3-isobutyl-1-methylxanthine (IBMX), 1 µM dexamethasone, 10 µg/mL insulin) that is a lipid accumulation-inducing factor rather than an extract, and Normal group (NC) was treated with only media (DMEM) containing only 10 µg/mL insulin without any treatment.

(3) Oil Red O Staining and Quantification

On the 8th day when fat cell differentiation was completed, each cell was recovered, and an inhibitory activity of the adipogenesis was evaluated therefrom as follows. In order to quantitatively analyze an amount of the fat accumulation of 3T3-L1 cells differentiated into each fat cell through an Oil Red O staining, the 3T3-L1 cells were washed with PBS, fixed with 3.7% formalin for 10 minutes, and washed with 60% isopropanol. Thereafter, each well was completely dried. The Oil red O Stainer was treated at a room temperature for 20 minutes, and washed 4 times with a distilled water. Then, the number and size of lipid droplets of the 3T3-L1 fat cells differentiated from each group were observed through a microscope (Eclipse ti, Nikon). For quantitative analysis, the fats were extracted using 100% isopropanol, and transferred to a 96-well plate by 200 µl each to measure Absorbance at 500 nm using an ELISA reader, which was expressed as a percentage for the absorbance value of the control group.

(4) Influence of Molokhia Extract on Production of Lipid Droplets in 3T3-L1 Preadipocyte Cells It was investigated whether production of lipid droplets created in the differentiation process of 3T3-L1 preadipocyte cells into fat cells was inhibited by treatment with the Molokhia hot water extract or the Molokhia polymer fraction.

Figure 13:
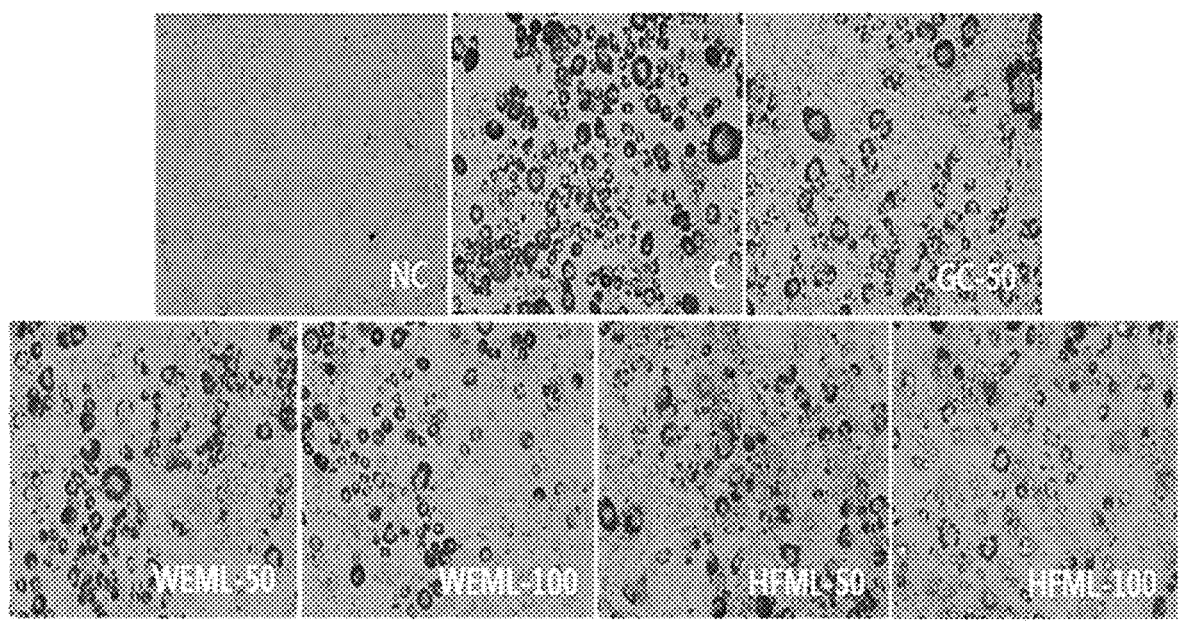
FIG. 13 is an Oil red O staining result for confirming a change in lipid content in 3T3-L1 cells by treatment with the hot water extract of Molokhia prepared from Example 1 and the Molokhia polymer fraction prepared from Example 2.
Figure 14:
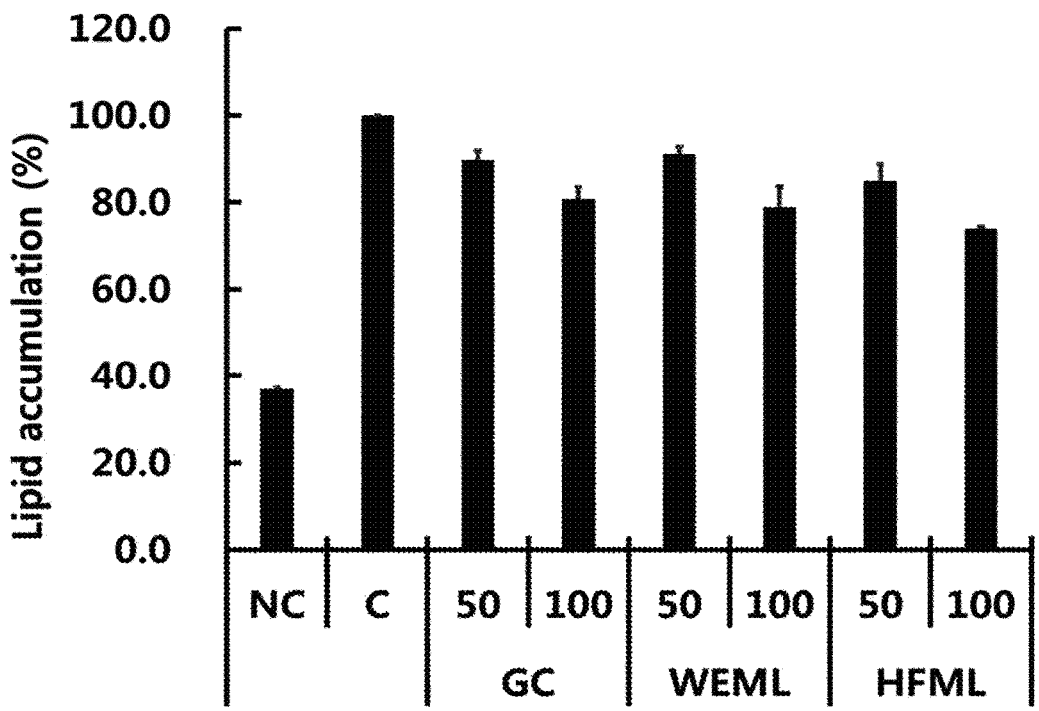
FIG. 14 is a result of experimenting an effect of inhibiting fat cell differentiation of the hot water extract of Molokhia prepared from Example 1 and the Molokhia polymer fraction prepared from Example 2.

FIG. 13 is an Oil red O staining result for confirming a change in lipid content in 3T3-L1 cells by treatment with the hot water extract of Molokhia prepared from Example 1 and the Molokhia polymer fraction prepared from Example 2. FIG. 14 is a result of experimenting an effect of inhibiting fat cell differentiation of the hot water extract of Molokhia prepared from Example 1 and the Molokhia polymer fraction prepared from Example 2.

As shown in FIGS. 13 and 14, it can be seen that fat synthesis was further suppressed in both the WEML group and the HFML group than in the control group (C) in which lipid accumulation was induced. In particular, efficacy of inhibiting fat cell differentiation and adipogenesis was most excellent in the WEML-100 group.

According to FIG. 14, compared to the control group (C) inducing lipid accumulation, the GC-50 group treated with the Garcinia cambogia extract (Comparative Example 3) exhibited an inhibitory ability of fat accumulation of about 10.3%, and the WEML-50 group and the WEML-100 group showed the inhibitory ability of fat accumulation of 9.1% and 21.2%, respectively. In addition, the HFML-50 group and the HFML-100 group showed the inhibitory ability of the fat accumulation of 15.2% and 26.1%, respectively. In summary, the Molokhia extract as well as the Molokhia polymer fraction according to the present invention exhibited the effect of suppressing the differentiation from 3T3-L1 preadipocyte cells to fat cells and adipogenesis, which were the same level as the conventional Garcinia cambogia extract. The Garcinia cambogia extract is known to cause a side effect in the human body and thus has a limit in its practical application, but the Molokhia extract or the Molokhia polymer fraction of the present invention has the advantage that there is no limit to application thereof because of little toxicity in vivo.

Experimental Example 9. Analysis of Inflammation-Related Factors of the Molokhia Hot Water Extract of Example 1

(1) Experimental Animals and Diet 45 6-week-old male C57BL/6J mice bred in a sterile environment were purchased from Central Experimental Animal Co., Ltd., and the breeding conditions of the mice were kept at a temperature of 22±2° C. and a humidity of 40 to 60%. Light and dark cycle was adjusted at intervals of 12 hours.

The mice were divided into 5 groups for 9 mice each, and an experimental diet was supplied and bred for 8 weeks. The experimental diet was a high-fat diet, and a modified AIN 76A purified rodent diet (fat of 60 cal %), which increased calories by 60 cal % by adding lard, was fed freely. The experiment was conducted by dividing the experimental group into a normal group (NC), a high-fat diet control group (HF), a positive control group (GC) to which 50 mg/kg of the Garcinia cambogia extract of Comparative Example 3 was administered, a group (WEML50) to which 50 mg/kg of the Molokhia extract of Example 1 was administered, and a group (WEML100) to which 100 mg/kg of the Molokhia extract of Example 1 was administered. The experimental group was allowed to freely consume water and the experimental diet. Weight gain during the experiment was measured at 10 A.M. at intervals of 1 week for 8 weeks from the start of the experiment. The Garcinia cambogia extract of Comparative Example 3 and the Molokhia extract of Example 1 were dissolved in the sterile saline, respectively, and administered orally.

(2) Collection of Blood and Organs

After the experiment was completed, the experimental animals were fasted for 12 hours and anesthetized with an iFran solution. Abdomens and thoracic cavities of the experimental animals were incised to coagulate the blood collected from the portal vein, and then the serum was separated and used to analyze concentrations of serum lipids and obesity-related hormones. White epididymal fat tissues and other organs were extracted from each experimental animal, blood and foreign substances were removed using a physiological saline, weighed, and then stored at −80° C. for analysis.

(3) Analysis of Change in Body Weight and Amount of Body Fat

Figure 15:
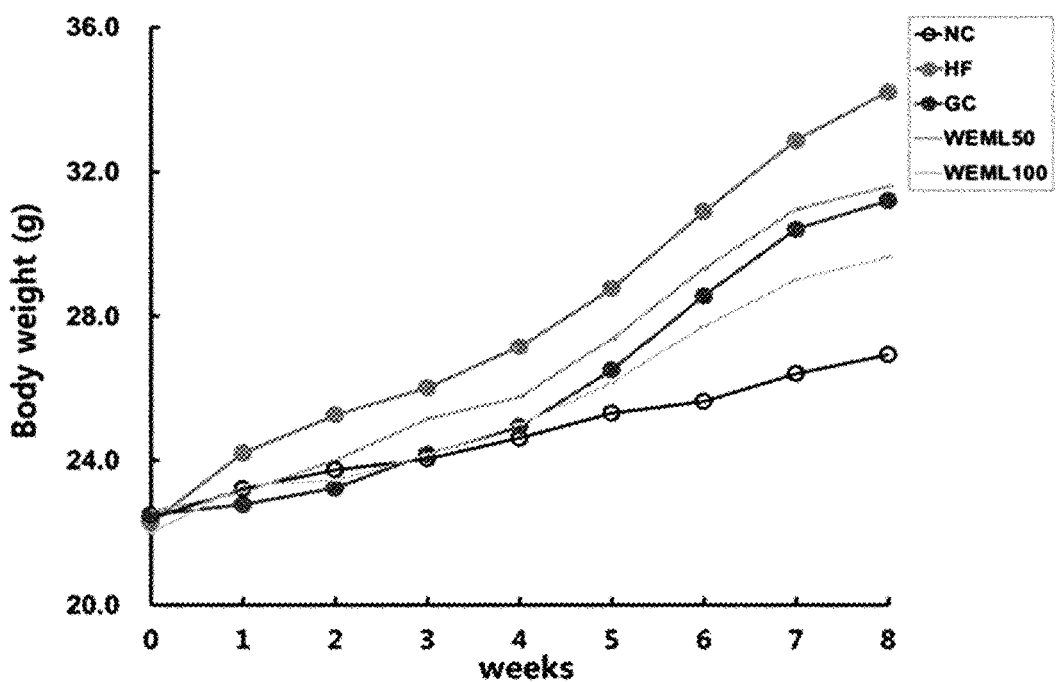
FIG. 15 is a graph showing a change in body weight over time for a Normal group (NC), a high-fat diet control group (HF), a positive control group (GC) to which 50 mg/kg of the Garcinia cambogia extract of Comparative Example 3 was administered, a group (WEML50) to which 50 mg/kg of the Molokhia extract of Example 1 was administered, and a group (WEML100) to which 100 mg/kg of the Molokhia extract of Example 1 was administered.

FIG. 15 is a graph showing a change in the body weight over time for a Normal group (NC), a high-fat diet control group (HF), a positive control group (GC) to which 50 mg/kg of the Garcinia cambogia extract of Comparative Example 3 was administered, a group (WEML50) to which 50 mg/kg of the Molokhia extract of Example 1 was administered, and a group (WEML100) to which 100 mg/kg of the Molokhia extract of Example 1 was administered.

Figure 16:
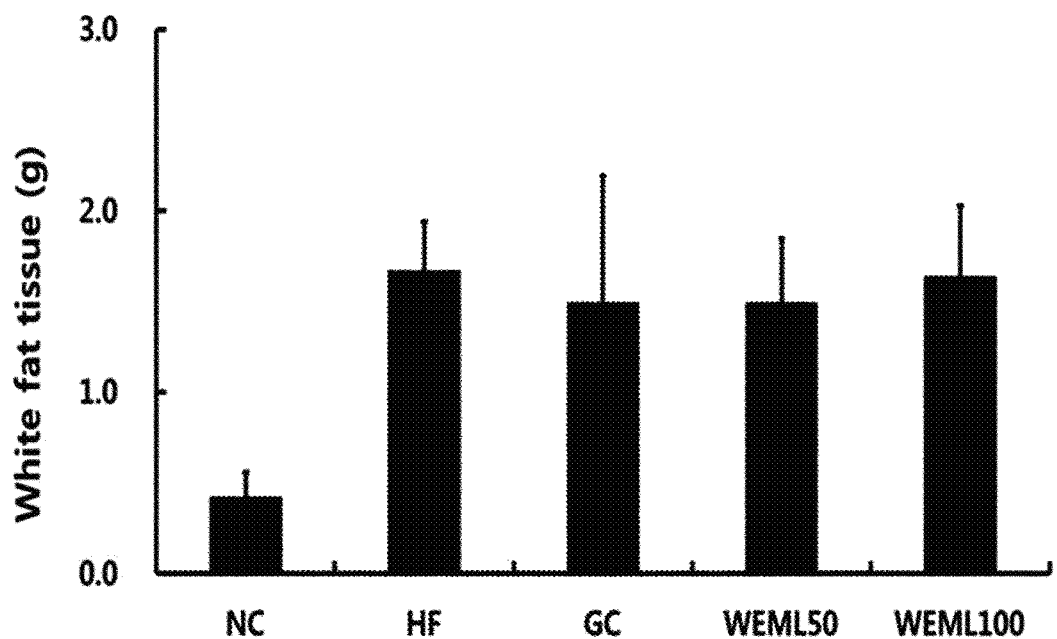
FIG. 16 is a graph showing a weight of white epididymal fat tissues extracted from a Normal group (NC), a high-fat diet control group (HF), a positive control group (GC) to which 50 mg/kg of the Garcinia cambogia extract of Comparative Example 3 was administered, a group (WEML50) to which 50 mg/kg of the Molokhia extract of Example 1 was administered, and a group (WEML100) to which 100 mg/kg of the Molokhia extract of Example 1 was administered.

FIG. 16 is a graph showing a weight of white epididymal fat tissues extracted from a Normal group (NC), a high-fat diet control group (HF), a positive control group (GC) to which 50 mg/kg of the Garcinia cambogia extract of Comparative Example 3 was administered, a group (WEML50) to which 50 mg/kg of the Molokhia extract of Example 1 was administered, and a group (WEML100) to which 100 mg/kg of the Molokhia extract of Example 1 was administered.

As shown in FIG. 15, the high-fat diet control group (HF) showed a significantly higher increase in body weight (11.9 g increase) compared to normal group (NC). Contrary to this, the groups to which the Garcinia cambogia extract of Comparative Example 3 and the Molokhia extract of Example 1 were orally administered showed a tendency to significantly lose body weight compared to the high-fat diet control group (HF). Concretely, the group (GC) that ingested the high-fat diet and was orally administered 50 mg/kg of the Garcinia cambogia extract (Comparative Example 3) lost the body weight 26.9% compared to the high-fat diet control group (HF). The group (WEML50) that was administered 50 mg/kg of the Molokhia extract and the group (WEML100) that was administered 100 mg/kg of the Molokhia extract while ingesting the high-fat diet lost body weight of 24.5% and 35.9%, respectively, compared to the high-fat diet control group (HF). In particular, the WEML100 group to which 100 mg/kg of the molokhia extract of Example 1 was administered orally had a significant decrease in body weight compared to the positive control group (GC group) ($p<0.05$).

As shown in FIG. 16, an amount of white epididymal fat extracted from each experimental group was significantly increased in the high-fat diet control group (HF) compared to Normal group (NV). It was confirmed that weights of the white epididymal fat tissues were reduced by about 10.5% and 1.8% in the WEML-50 group and the WEML-100 group to which the Molokhia extract of Example 1 was administered, compared to the high-fat diet control group (HF). Therefore, it can be seen that the Molokhia extract of the present invention has an effect of reducing a weight of the fat tissue, and not only loses the body weight but also suppresses increase in body fat.

(4) Analysis of Plasma Lipid Content

Concentrations of endotoxin, neutral fat, and total cholesterol in a serum were analyzed by an enzyme method using a blood analysis kit from Shinyang Chemical Co., Ltd. The neutral fat was analyzed by Tiglyzyme-V and the total cholesterol was analyzed by Cholestezyme-V. A Pierce™ LAL Chromogenic Endotoxin Quantitation Kit (Thermo scientific) was used to determine an amount of endotoxin in the serum of a mouse.

Figure 17:
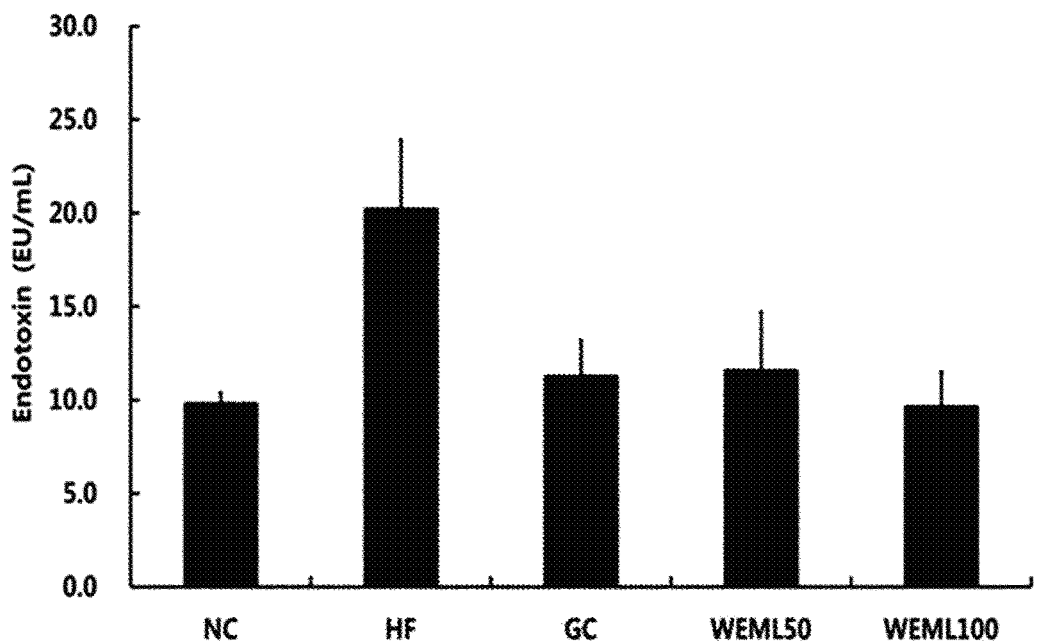
FIG. 17 is a graph showing a concentration of endotoxins in the serum extracted from a Normal group (NC), a high-fat diet control group (HF), a positive control group (GC) to which 50 mg/kg of the Garcinia cambogia extract of Comparative Example 3 was administered, a group (WEML50) to which 50 mg/kg of the Molokhia extract of Example 1 was administered, and a group (WEML100) to which 100 mg/kg of the Molokhia extract of Example 1 was administered.
Figure 18:
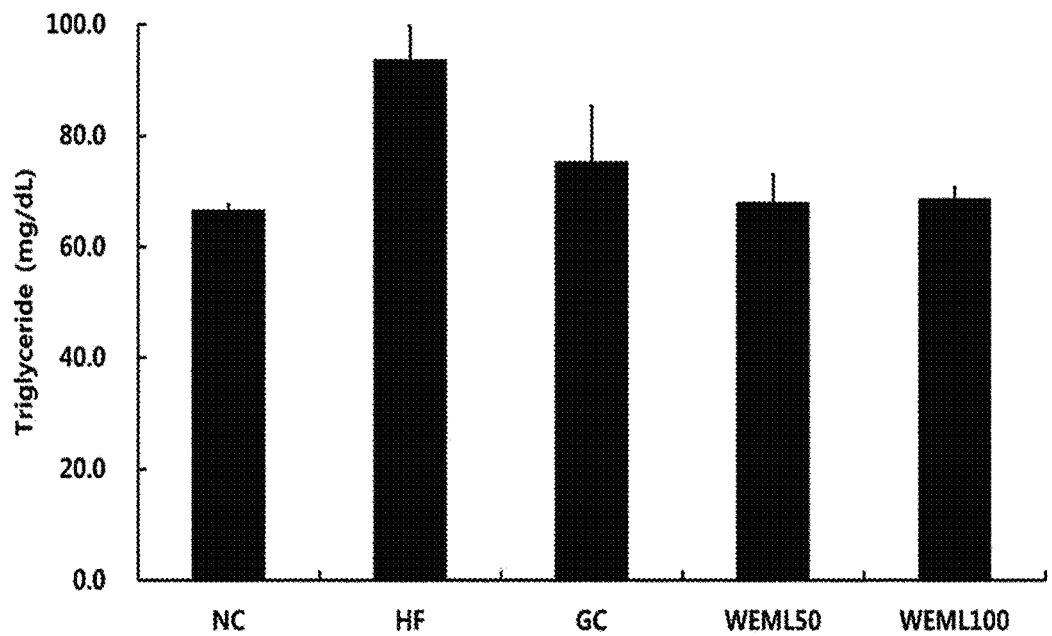
FIG. 18 is a graph showing a concentration of neutral fats in the serum extracted from a Normal group (NC), a high-fat diet control group (HF), a positive control group (GC) to which 50 mg/kg of the Garcinia cambogia extract of Comparative Example 3 was administered, a group (WEML50) to which 50 mg/kg of the Molokhia extract of Example 1 was administered, and a group (WEML100) to which 100 mg/kg of the Molokhia extract of Example 1 was administered.
Figure 19:
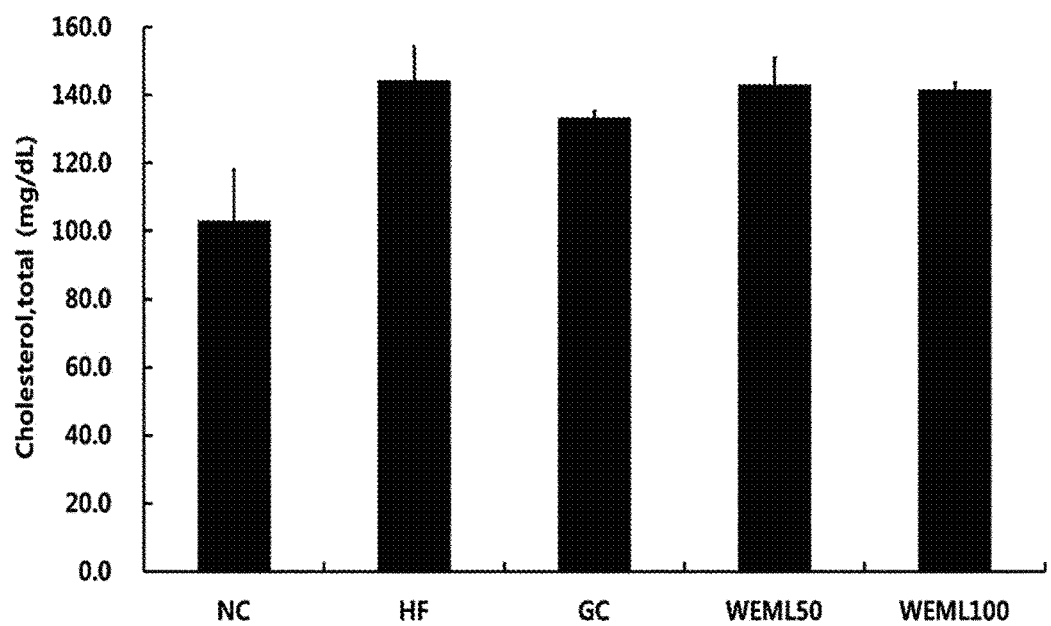
FIG. 19 is a graph showing a total cholesterol concentration in the serum extracted from a Normal group (NC), a high-fat diet control group (HF), a positive control group (GC) to which 50 mg/kg of the Garcinia cambogia extract of Comparative Example 3 was administered, a group (WEML50) to which 50 mg/kg of the Molokhia extract of Example 1 was administered, and a group (WEML100) to which 100 mg/kg of the Molokhia extract of Example 1 was administered.

FIG. 17 is a graph showing a concentration of endotoxins in a serum extracted from a Normal group (NC), a high-fat diet control group (HF), a positive control group (GC) to which 50 mg/kg of the Garcinia cambogia extract of Comparative Example 3 was administered, a group (WEML50) to which 50 mg/kg of the Molokhia extract of Example 1 was administered, and a group (WEML100) to which 100 mg/kg of the Molokhia extract of Example 1 was administered. FIG. 18 is a graph showing a concentration of a neutral fat in a serum extracted from a Normal group (NC), a high-fat diet control group (HF), a positive control group (GC) to which 50 mg/kg of the Garcinia cambogia extract of Comparative Example 3 was administered, a group (WEML50) to which 50 mg/kg of the Molokhia extract of Example 1 was administered, and a group (WEML100) to which 100 mg/kg of the Molokhia extract of Example 1 was administered. FIG. 19 is a graph showing a total cholesterol concentration in a serum extracted from a normal group (NC), a high-fat diet control group (HF), a positive control group (GC) to which 50 mg/kg of the Garcinia cambogia extract of Comparative Example 3 was administered, a group (WEML50) to which 50 mg/kg of the Molokhia extract of Example 1 was administered, and a group (WEML100) to which 100 mg/kg of the Molokhia extract of Example 1 was administered.

As shown in FIG. 17, the endotoxin was increased by 106.3% in the high-fat diet control group (HF) compared to normal group (NC), but the WEML-50 group and the WEML-100 group were reduced by 42.7% and 52.3%, respectively, compared to the high-fat diet control group (HF). Accordingly, it was confirmed that the Molokhia extract of Example 1 reduced the concentration of the endotoxin in the serum to suppress obesity and also prevent inflammation induced by obesity at the same time.

According to FIGS. 18 and 19, the neutral fat and the total cholesterol were significantly increased in the high-fat diet control group (HF) compared to Normal group (NC), but they were significantly decreased in the WEML-50 group and the WEML-100 group compared to the high-fat diet control group (HF). It can be seen that even though the Molokhia extract of Example 1 according to the present invention was co-administered the high-fat diet, it showed levels of neutral fat and total cholesterol similar to those of normal group (NC), thereby having a remarkable effect on obesity suppression.

(5) Hormone Related to Fat Differentiation in Plasma (Leptin, Insulin)

Concentrations of leptin (mouse leptin ELISA kit, R&D systems, Minneapolis, USA) and insulin (mouse insulin ELISA kit, ALPCO, New Hampshire, USA) as hormones related to fat differentiation in a serum were analyzed using an ELISA analysis method.

Figure 20:
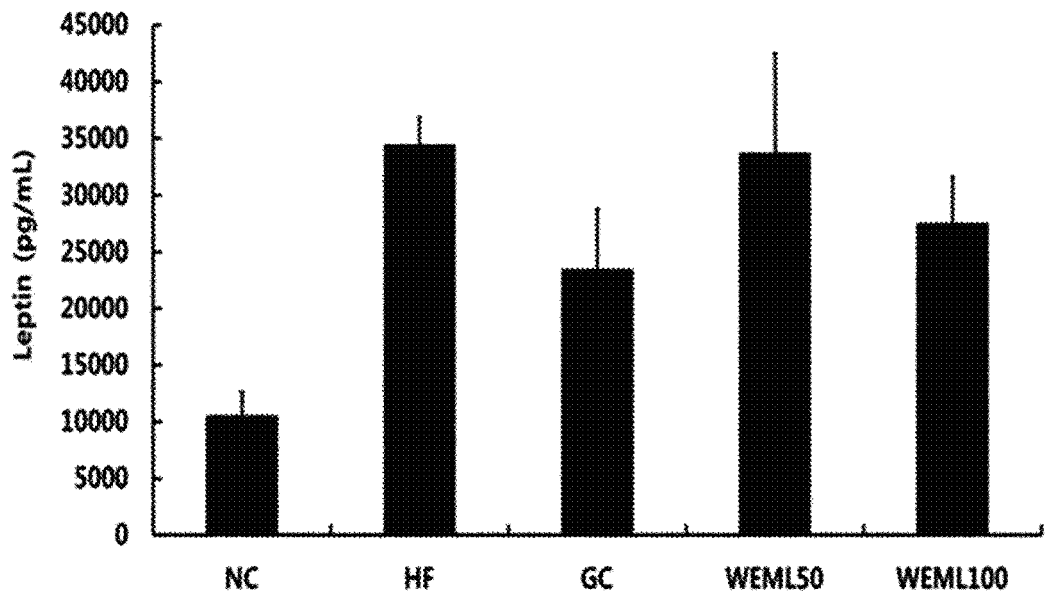
FIG. 20 is a graph showing a leptin concentration in the serum extracted from a Normal group (NC), a high-fat diet control group (HF), a positive control group (GC) to which 50 mg/kg of the Garcinia cambogia extract of Comparative Example 3 was administered, a group (WEML50) to which 50 mg/kg of the Molokhia extract of Example 1 was administered, and a group (WEML100) to which 100 mg/kg of the Molokhia extract of Example 1 was administered.
Figure 21:
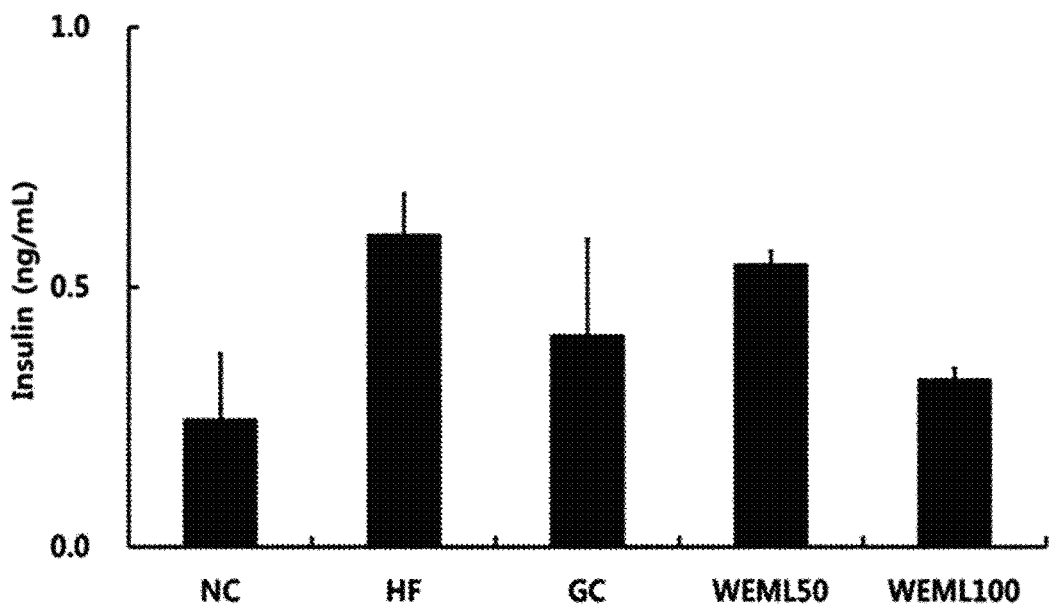
FIG. 21 is a graph showing an insulin concentration in the serum extracted from a Normal group (NC), a high-fat diet control group (HF), a positive control group (GC) to which 50 mg/kg of the Garcinia cambogia extract of Comparative Example 3 was administered, a group (WEML50) to which 50 mg/kg of the Molokhia extract of Example 1 was administered, and a group (WEML100) to which 100 mg/kg of the Molokhia extract of Example 1 was administered.

FIG. 20 is a graph showing a leptin concentration in the serum extracted from a Normal group (NC), a high-fat diet control group (HF), a positive control group (GC) to which 50 mg/kg of the Garcinia cambogia extract of Comparative Example 3 was administered, a group (WEML50) to which 50 mg/kg of the Molokhia extract of Example 1 was administered, and a group (WEML100) to which 100 mg/kg of the Molokhia extract of Example 1 was administered. FIG. 21 is a graph showing an insulin concentration in the serum extracted from a Normal group (NC), a high-fat diet control group (HF), a positive control group (GC) to which 50 mg/kg of the Garcinia cambogia extract of Comparative Example 3 was administered, a group (WEML50) to which 50 mg/kg of the Molokhia extract of Example 1 was administered, and a group (WEML100) to which 100 mg/kg of the Molokhia extract of Example 1 was administered.

As shown in FIGS. 20 and 21, leptin is a hormone produced and secreted in fat tissue, and is known to be involved in energy metabolism and body weight control by suppressing appetite and increasing energy consumption in proportion to an amount of body fat in blood. The leptin concentration was decreased by 31.8%, 2.1%, and 20.0% in the GC group, the WEML-50 group, and the WEML-100 group, respectively, compared to the high-fat diet control group (HF). In addition, measurement of the insulin concentration in the serum indicated that it was decreased by 32.3%, 9.5%, and 46.5% in the GC group, the WEML-50 group, and the WEML-100 group, respectively, compared to the high-fat diet control group (HF). Therefore, the Molokhia extract of Example 1 showed a result of significantly reducing the concentrations of leptin and insulin in the serum, which is associated with a decrease in an amount of body fat.

If all the above results were summarized, the Molokhia extract of Example 1 was confirmed to exhibit an effect of improving, preventing or treating obesity when used in a concentration of 50 mg/kg or more, but showed the best effect when used in a concentration of 100 mg/kg or more, preferably in a concentration of 100 to 10,000 mg/kg. There is no increase in the effect when used at a concentration of 10 g/kg or more.

Hereinafter, Formulation Examples of a composition comprising a powder of the present invention will be described, but the present invention is intended to explain them in detail rather than limiting them.

Formulation Example 1. Preparation of Powder

| | |
|---|---|
| Molokhia hot water extract of Example 1; or Molokhia polymer fraction of Example 2; | 500 mg |
| Lactose | 100 mg |
| Talc | 10 mg |

The above ingredients are mixed with each other and filled in an airtight cloth to prepare a powder.

Formulation Example 2. Preparation of Tablet

| | |
|---|---|
| Molokhia hot water extract of Example 1; or Molokhia polymer fraction of Example 2; | 300 mg |
| Corn starch | 100 mg |
| Lactose | 100 mg |
| Talc | 10 mg |
| Magnesium stearate | 2 mg |

After the above ingredients are mixed with each other, the mixture is tableted according to a conventional tableting method to prepare a tablet.

Formulation Example 3. Preparation of Capsule

| | |
|---|---|
| Molokhia hot water extract of Example 1; or Molokhia polymer fraction of Example 2; | 200 mg |
| Crystalline cellulose | 3 mg |
| Lactose | 14.8 mg |
| Magnesium stearate | 0.2 mg |

According to a conventional capsule preparation method, the above ingredients are mixed with each other and filled into gelatin capsule to prepare a capsule.

Formulation Example 4. Preparation of Injection

| | |
|---|---|
| Molokhia hot water extract of Example 1; or Molokhia polymer fraction of Example 2; | 600 mg |
| Mannitol | 180 mg |
| Sterile distilled water for injection | 2,974 mg |
| $Na_2HPO_4, 12H_2O$ | 26 mg |

According to a conventional method, an injection is prepared by filling an ampoule with the contents of the above ingredients.

Formulation Example 5. Preparation of Liquid Formulation

| | |
|---|---|
| Molokhia hot water extract of Example 1; or Molokhia polymer fraction of Example 2; | 4 mg |
| Isomerized sugar | 10 g |
| Mannitol | 5 g |
| Purified water | appropriate amount |

According to a conventional method, a liquid formulation is prepared by adding each of the above ingredients to a purified water to dissolve the same, adding an appropriate amount of a lemony flavor to the dissolved ingredients, mixing the above ingredients with each other, adding purified water to the mixture to adjust the total mixture to 100 g, and then filling a brown bottle for sterilization with the same.

Formulation Example 6. Preparation of Granules

| | |
|---|---|
| Molokhia hot water extract of Example 1; or Molokhia polymer fraction of Example 2; | 1,000 mg |
| Vitamin mixture | appropriate amount |
| Vitamin A acetate | 70 μg |
| vitamin E | 1.0 mg |
| Vitamin B1 | 0.13 mg |
| Vitamin B2 | 0.15 mg |
| Vitamin B6 | 0.5 mg |
| Vitamin B12 | 0.2 μg |
| Vitamin C | 10 mg |
| Biotin | 10 μg |
| Nicotinic acid amide | 1.7 mg |
| Folic acid | 50 μg |
| Calcium pantothenate | 0.5 mg |
| Inorganic mixture | appropriate amount |
| Ferrous sulfate | 1.75 mg |
| Zinc oxide | 0.82 mg |
| Magnesium carbonate | 25.3 mg |
| Potassium monophosphate | 15 mg |
| Calcium diphosphate | 55 mg |
| Potassium citrate | 90 mg |
| Calcium carbonate | 100 mg |
| Magnesium chloride | 24.8 mg |

The compositive ratio of the vitamins and the mineral materials is made by mixing the ingredients relatively suitable for granules as a preferred embodiment, but can also be modified to a certain mixing ratio arbitrarily. According to a conventional method, the above ingredients are mixed with each other to prepare the granules. These granules can be used to prepare a health functional food composition according to the conventional method.

Formulation Example 7. Preparation of Functional Beverage

| | |
|---|---|
| Molokhia hot water extract of Example 1; or Molokhia polymer fraction of Example 2; | 1,000 mg |
| Citric acid | 1,000 mg |
| Oligosaccharide | 100 g |

| | |
|---|---|
| Plum concentrate | 2 g |
| Taurine | 1 g |
| Adding purified water | total 900 mL |

According to a conventional method, the above ingredients are mixed with each other and heated at 85° C. for about 1 hour while stirring. Thereafter, the obtained solution is filtered and filled into a sterilized 2 L container, which is sealed/sterilized, and then stored in a refrigerator. In this case, the stored solution is used to prepare a functional beverage composition of the present invention.

The above compositive ratio is made by mixing the ingredients relatively suitable for a favorite beverage as a preferred embodiment, but can also be modified to a certain mixing ratio arbitrarily according to regional and ethnic preferences such as the demand class, the country of demand, and the purpose of use.

We claim:

1. A method of treating a disease in a human in need thereof comprising administering to the human in need thereof a therapeutically effective amount of a Molokhia extract to effectively treat the disease in the human in need thereof, wherein the disease is selected from the group consisting of leaky gut syndrome, Crohn's disease, ulcerative colitis, chronic Behcet's disease, infectious enteritis, ischemic bowel disease and radiation enteritis.

2. The method of claim 1, wherein the Molokhia extract is extracted with water, an alcohol having 1 to 4 carbon atoms, or a mixed solvent thereof.

3. The method of claim 1, wherein the Molokhia extract is a high molecular weight fraction.

4. The method of claim 3, wherein the molecular weight of the high molecular weight fraction is 10 kDa or more.

5. The method of claim 4, wherein the high molecular weight fraction is a Molokhia polysaccharide.

6. The method of claim 1, wherein the Molokhia extract has a prebiotic activity in the human in need thereof.

7. The method of claim 6, wherein the prebiotic activity is to promote proliferation of beneficial bacteria in the intestine of the human in need thereof.

8. The method of claim 6, wherein the beneficial bacteria in the intestine of the human in need thereof are selected from the group consisting of *Bifidobacterium, Lactobacillus, Lactococcus* and *Bacteroides*.

9. The method of claim 6, wherein the prebiotic activity is enhancing the intestinal health or intestinal function in the human in need thereof by improving intestinal flora in the human in need thereof.

10. The method of claim 1, wherein the Molokhia extract increases immune activity, suppresses inflammatory response, and reduces activation of inflammatory cells in the human in need thereof.

11. The method of claim 1, wherein the Molokhia extract enhances expression of IgA and reduces expression of IL-6 and LTB4 in the human in need thereof.

12. The method of claim 1, wherein the leaky gut syndrome is induced by a high-fat diet in the human in need thereof.

13. The method of claim 1, wherein the Molokhia extract reduces total fat cell differentiation and fat accumulation in the human in need thereof, reduces gain of body weight and body fat in the human in need thereof, lowers a concentration of endotoxins in the human in need thereof, neutral fat and total cholesterol in the serum in the human in need thereof, and reduces expression of hormones related to fat differentiation in the serum of the human in need thereof.

* * * * *